(12) United States Patent
Fruhauf et al.

(10) Patent No.: US 10,076,125 B2
(45) Date of Patent: *Sep. 18, 2018

(54) POLYPEPTIDE FOR HYDROLYTIC CLEAVAGE OF ZEARALENONE AND/OR ZEARALENONE DERIVATIVES, ISOLATED POLYNUCLEOTIDE THEREOF AS WELL AS A POLYPEPTIDE CONTAINING AN ADDITIVE, USE OF SAME AS WELL AS A PROCESS

(71) Applicant: Erber Aktiengesellschaft, Getzersdorf bei Traismauer (AT)

(72) Inventors: Sebastian Fruhauf, Neulengbach (AT); Michaela Thamhesl, Vienna (AT); Martin Pfeffer, Tulln (AT); Dieter Moll, Stockerau (AT); Gerd Schatzmayr, Tulln (AT); Eva Maria Binder, Tullin (AT)

(73) Assignee: ERBER AKTIENGESELLSCHAFT, Getzersdorf bei Traismauer (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,232

(22) Filed: Feb. 26, 2016

(65) Prior Publication Data
US 2016/0319258 A1    Nov. 3, 2016

Related U.S. Application Data

(63) Continuation of application No. PCT/AT2014/000164, filed on Aug. 27, 2014.

(30) Foreign Application Priority Data

Aug. 28, 2013 (AT) ..................... 667/2013

(51) Int. Cl.
| | | |
|---|---|---|
| *A23K 10/14* | (2016.01) | |
| *A23K 50/80* | (2016.01) | |
| *A23K 50/75* | (2016.01) | |
| *A23K 50/30* | (2016.01) | |
| *A23L 3/3571* | (2006.01) | |
| *C12N 9/18* | (2006.01) | |
| *C12N 9/14* | (2006.01) | |

(52) U.S. Cl.
CPC .............. *A23K 10/14* (2016.05); *A23K 50/30* (2016.05); *A23K 50/75* (2016.05); *A23K 50/80* (2016.05); *A23L 3/3571* (2013.01); *C12N 9/14* (2013.01); *C12N 9/18* (2013.01); *C12Y 301/01* (2013.01); *A23V 2002/00* (2013.01); *Y02A 40/818* (2018.01)

(58) Field of Classification Search
CPC ........... A23L 3/3571; C12N 9/18; C12N 9/14; A23V 2002/00; C12Y 301/01; A23K 10/14; A23K 50/75; A23K 50/30; A23K 50/80
See application file for complete search history.

(56) References Cited

U.S. PATENT DOCUMENTS 6,812,380 B2 * 11/2004 Karlovsky ............... C12N 9/18
435/320.1

FOREIGN PATENT DOCUMENTS

| EP | 0 938 575 | 9/1999 |
|---|---|---|
| WO | 02/076205 A2 | 10/2002 |
| WO | 03/053161 A1 | 7/2003 |
| WO | 2012/113827 A1 | 8/2012 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
International Search Report, dated Feb. 17, 2015 (6 pages).
"SubName: Full=Hydrolase", XP-002732829, <http://www.uniprot.org/uniprot/W5W1S2.txt?version=2<, Apr. 16, 2014 (1 page).
"SubName: Full=Alpha/beta hydrolase fold containing protein", XP-002732830, <http://www.uniprot.org/uniprot/G2P9U4.txt?version=8>, Nov. 16, 2011 (1 page).
"SubName: Full=Hydrolase", XP-002734870, <http://www.uniprot.org/uniprot/H1Q8U7.txt?version=6>, Mar. 21, 2012 (1 page).
"SubName: Full=Alpha/beta hydrolase", XP-002734871, <http://www.uniprot.org/uniprot/M2XGD3.txt?version=3>, May 1, 2013 (1 page).
"SubName: Full=Putative uncharacterized protein", XP-002734872, <http://www.uniprot.org/uniprot/C6WMV9.txt?version=16>, Sep. 22, 2009 (1 page).

(Continued)

*Primary Examiner* — Ganapathirama Raghu
(74) *Attorney, Agent, or Firm* — Jacobson Holman, PLLC

(57) ABSTRACT

The invention relates to a polypeptide for the hydrolytic cleavage of zearalenone and/or at least one zearalenone derivative, said polypeptide being a hydrolase having an amino acid sequence selected from the group consisting of SEQ ID NO: 1-15 or a functional variant thereof, wherein the sequence of the functional variant is at least 40% identical to at least one of the amino acid sequences. The invention also relates to: an additive containing the polypeptide; an isolated polynucleotide that encodes the polypeptide; and a method for the hydrolytic cleavage of zearalenone and/or of at least one zearalenone derivative using the polypeptide.

6 Claims, 7 Drawing Sheets
Specification includes a Sequence Listing.

(56) References Cited

OTHER PUBLICATIONS

Rodrigues et al., "Microorganisms and their enzymes for detoxifying mycotexms posing a risk to livestock animals", American Chemical Society, Dec. 20, 2009, vol. 1031, pp. 107-117 (11 pages).

Takahashi-Ando et al., "A novel lactotiohydrolase responsible for the detoxification of zearalenone: enzyme purification and gene cloning", Biochemical Journal, Jul. 1, 2002, vol. 365, pp. 1-6 (6 pages).

Yu et al., "Oxidaiion of zearalenone by extracellular enzymes from *Acinetobacter* sp. SM04 into smaller estrogenic products", World Journal of Microbiology and Biotechnology, Apr. 26, 2011, vol. 27, No. 11, pp. 2675-2681 (7 pages).

* cited by examiner

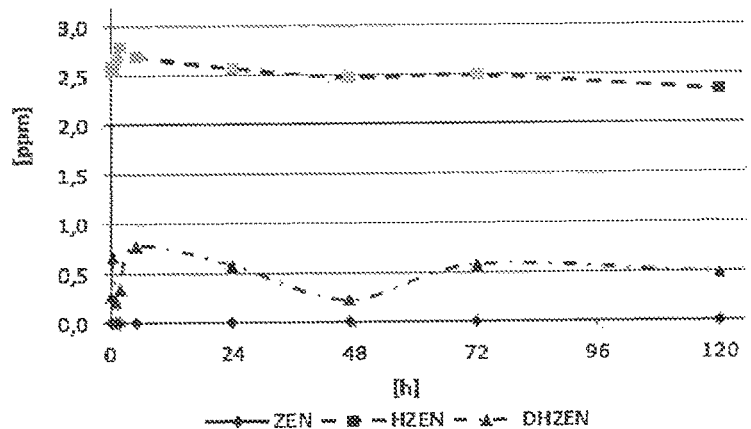
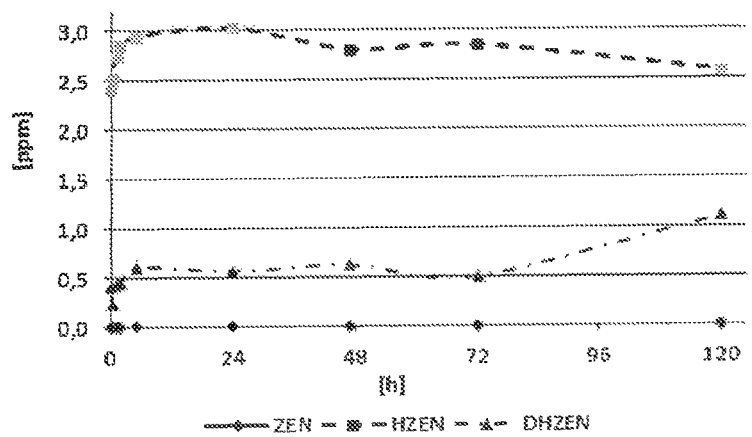
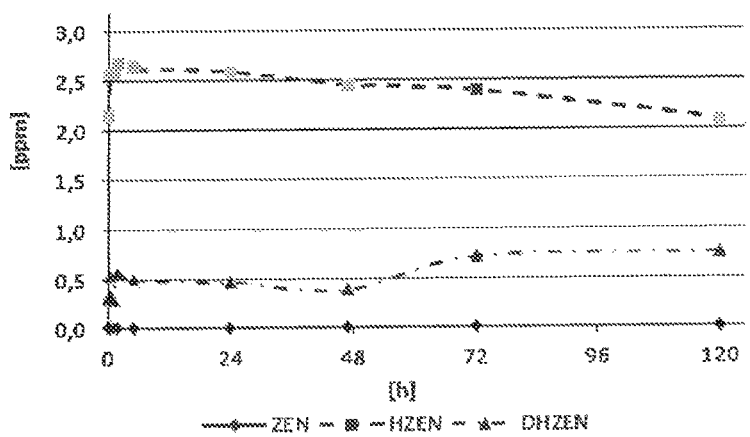

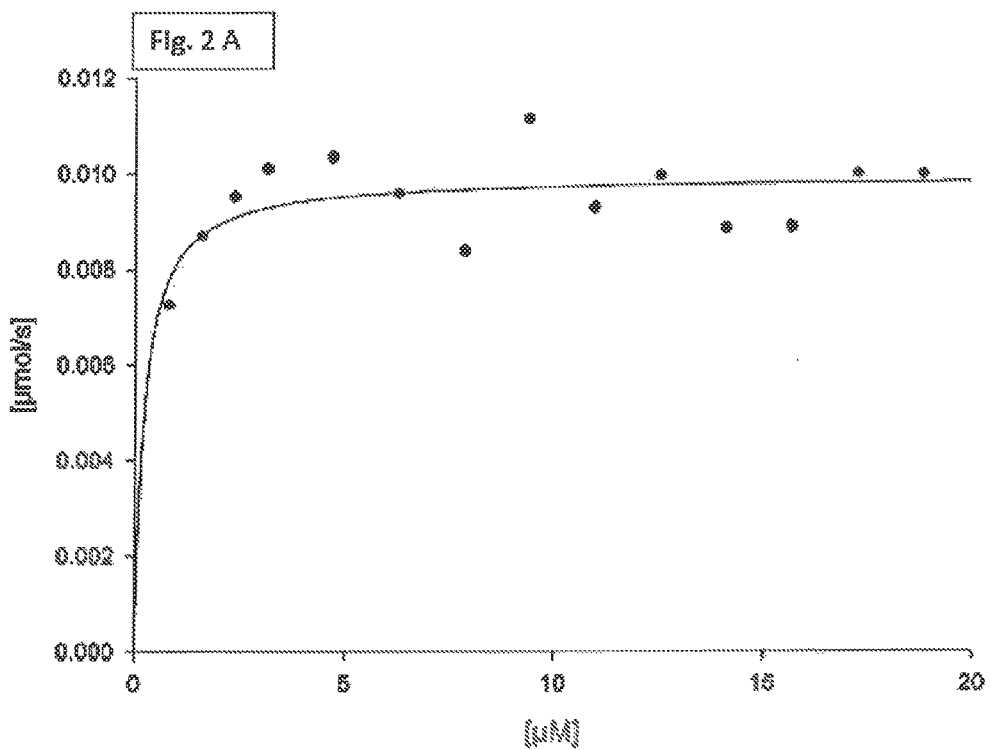
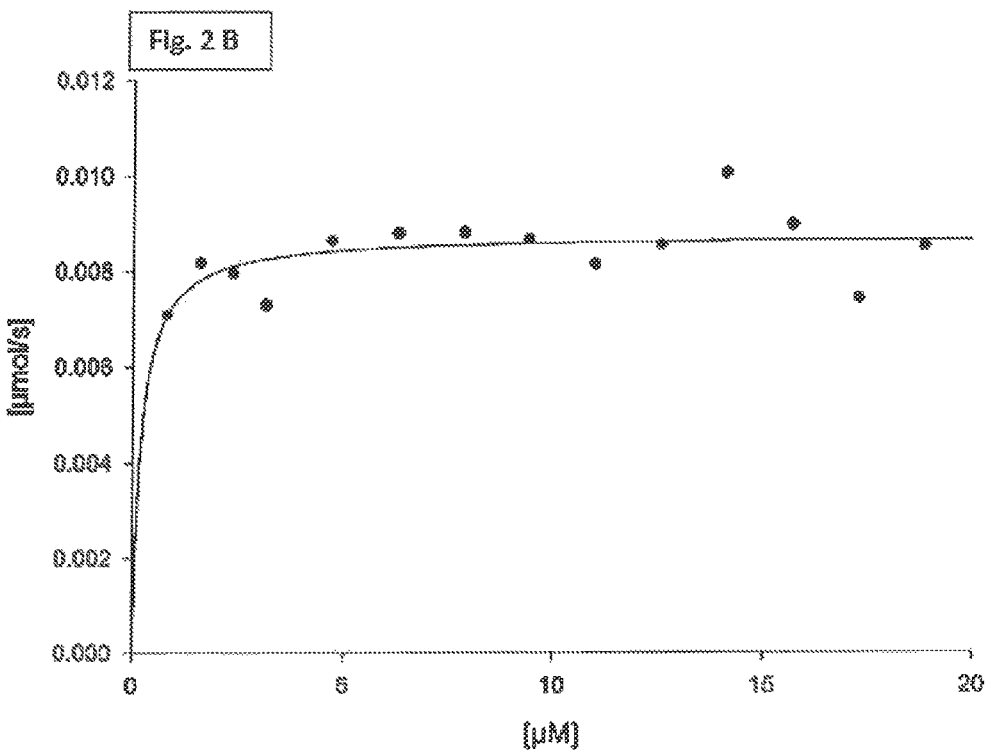

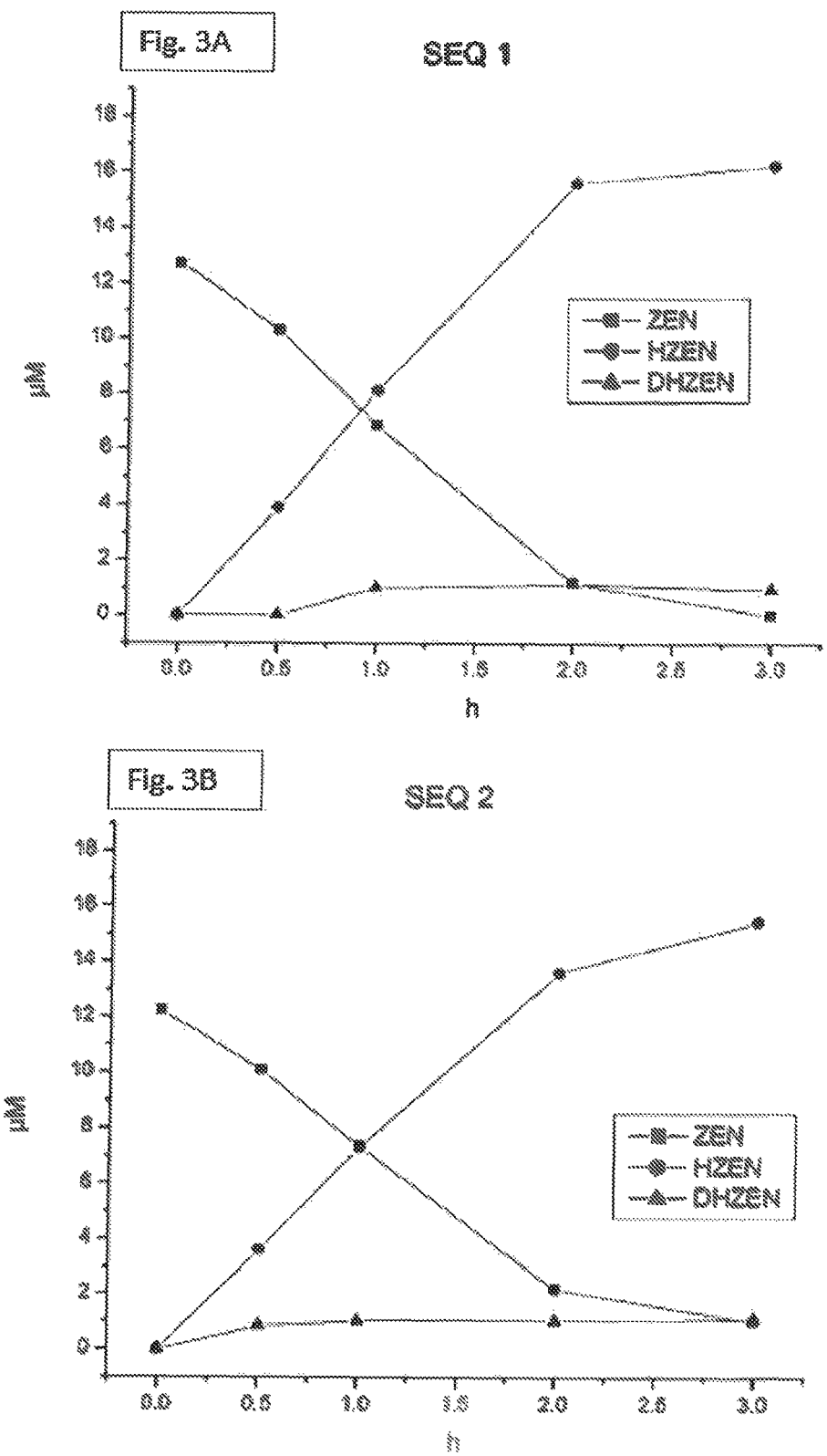

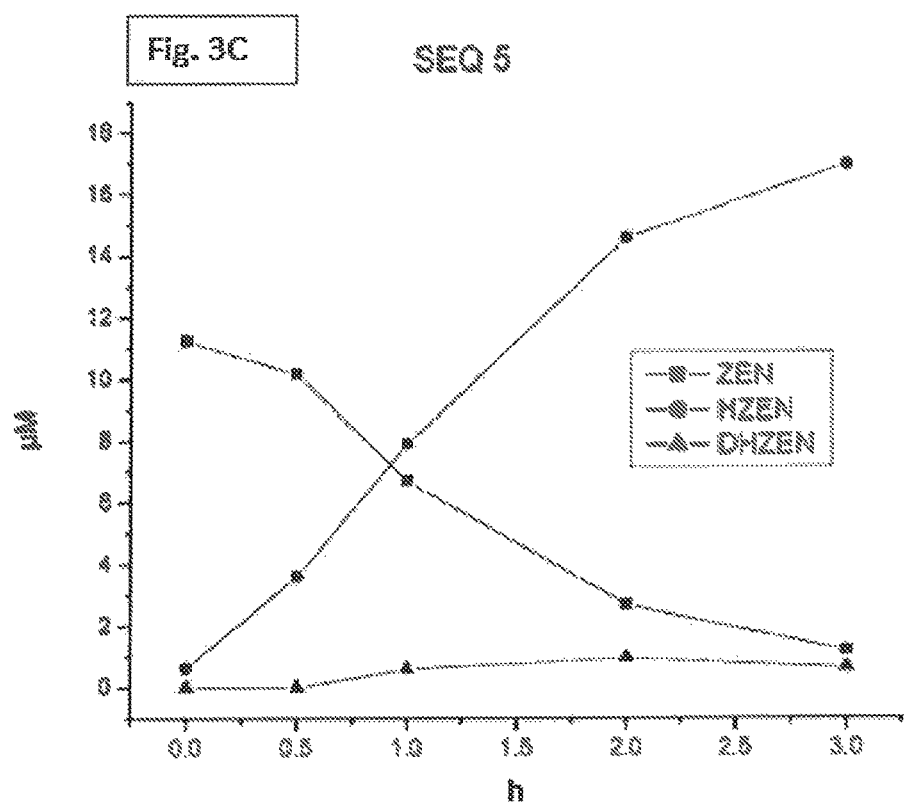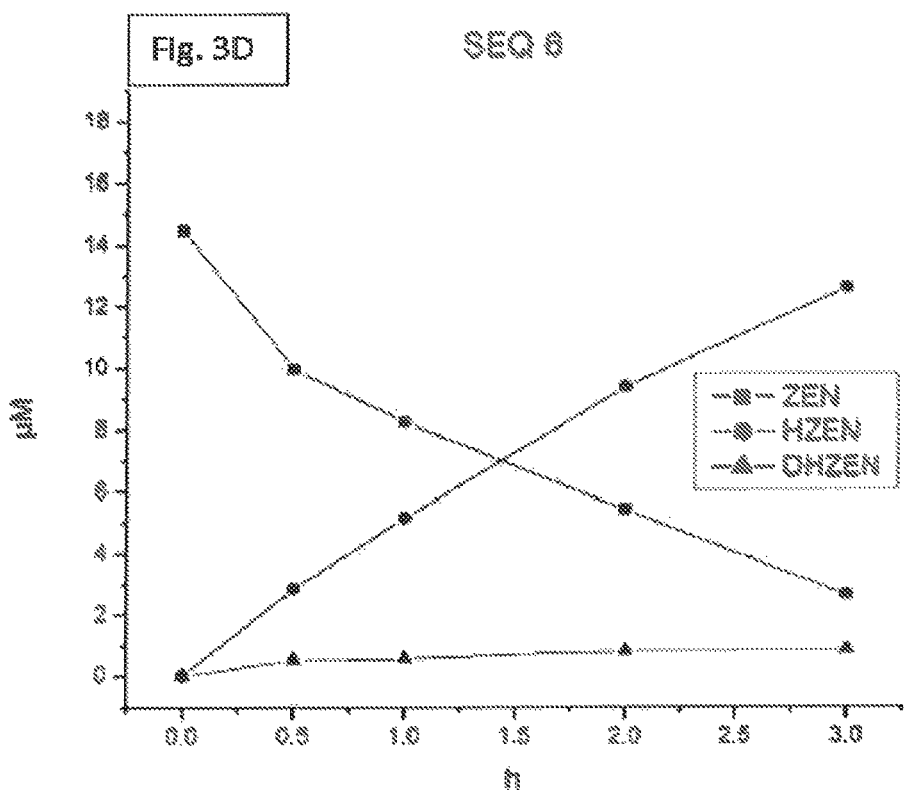

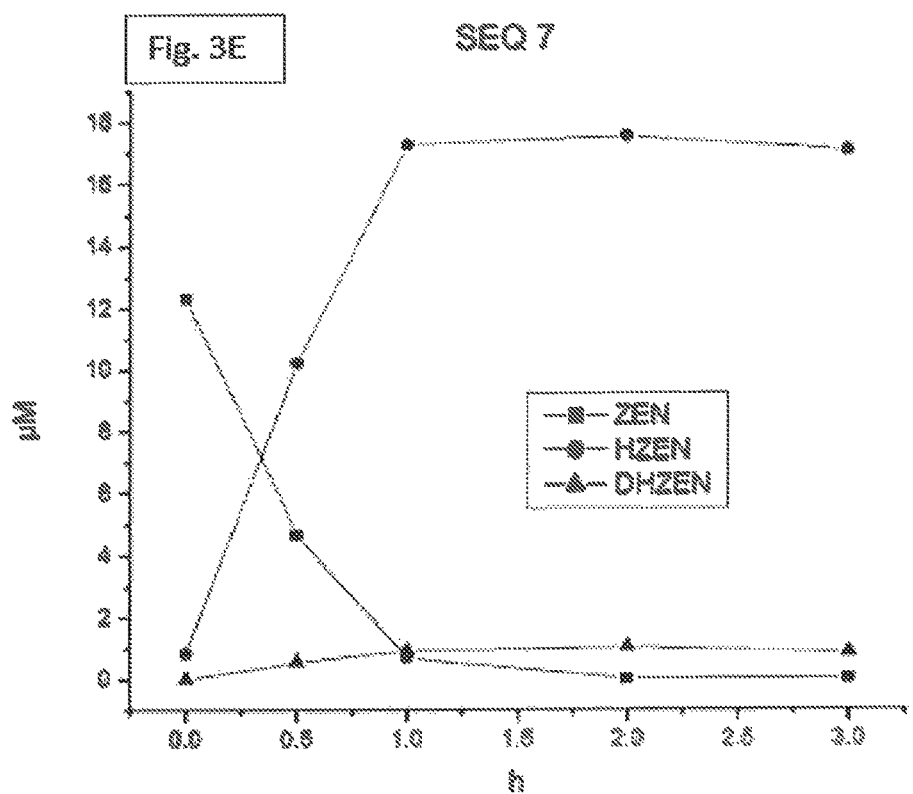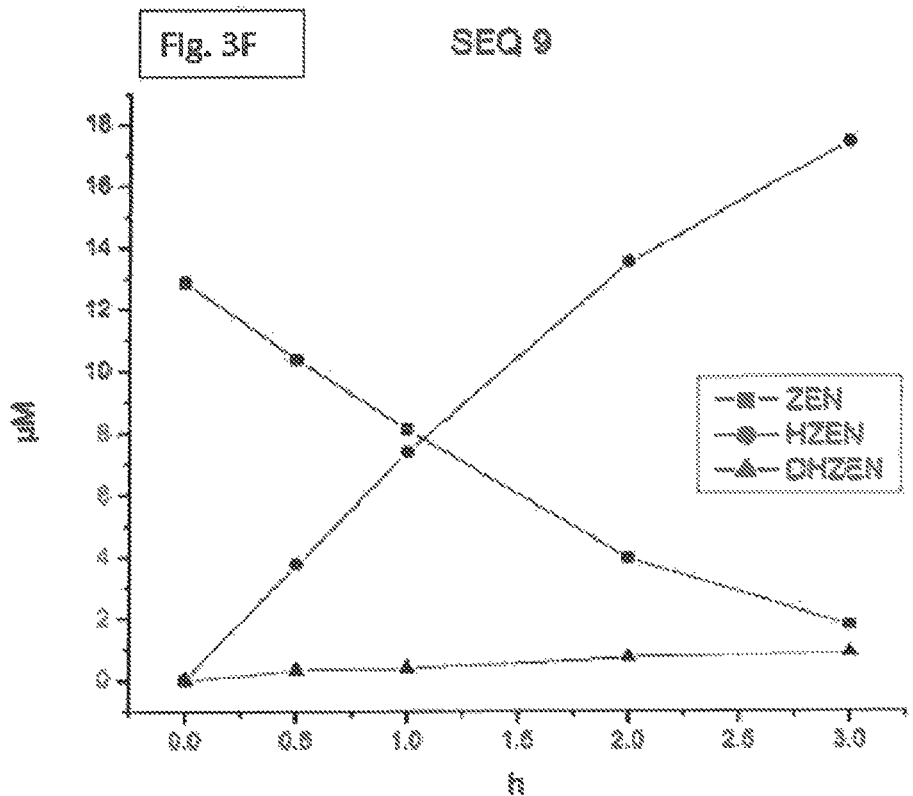

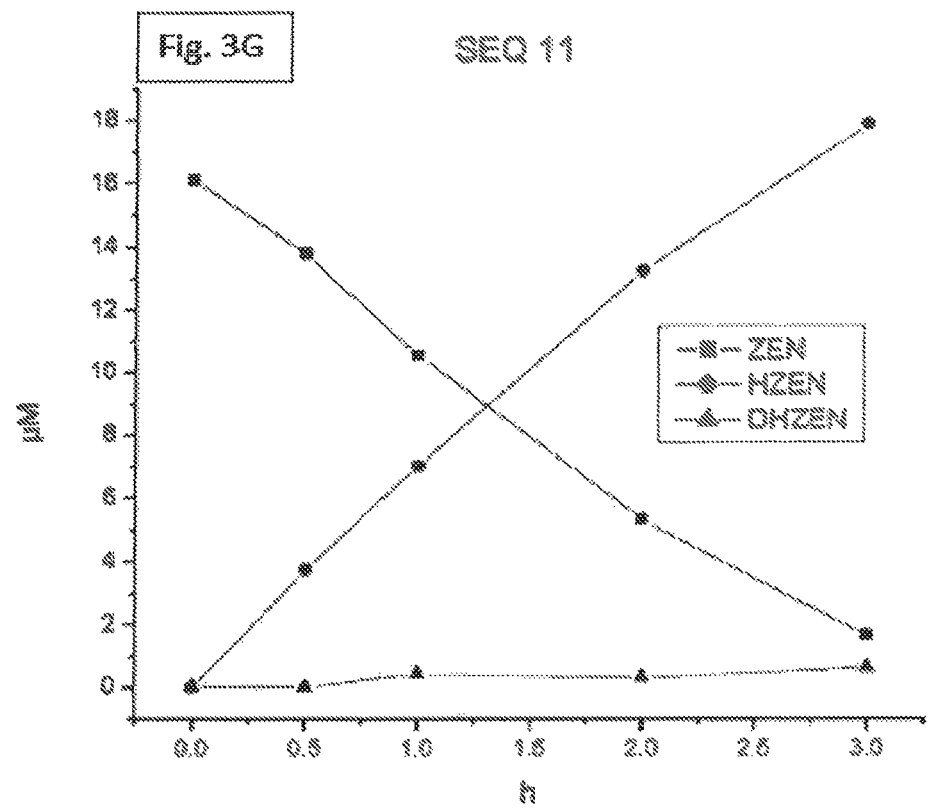
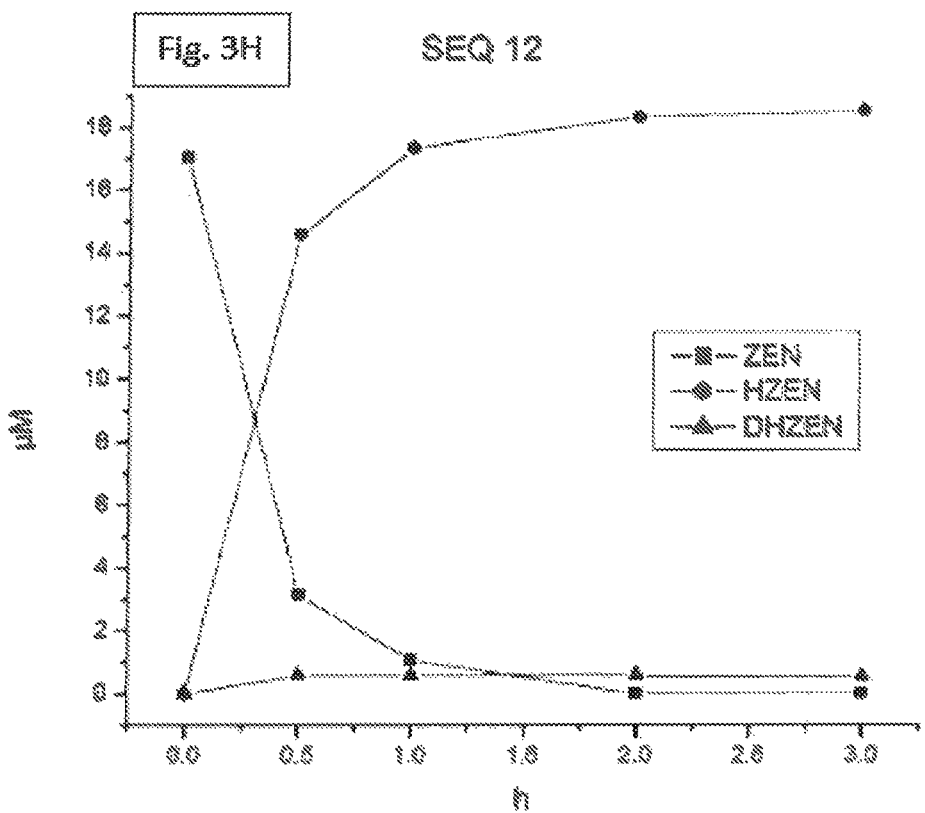

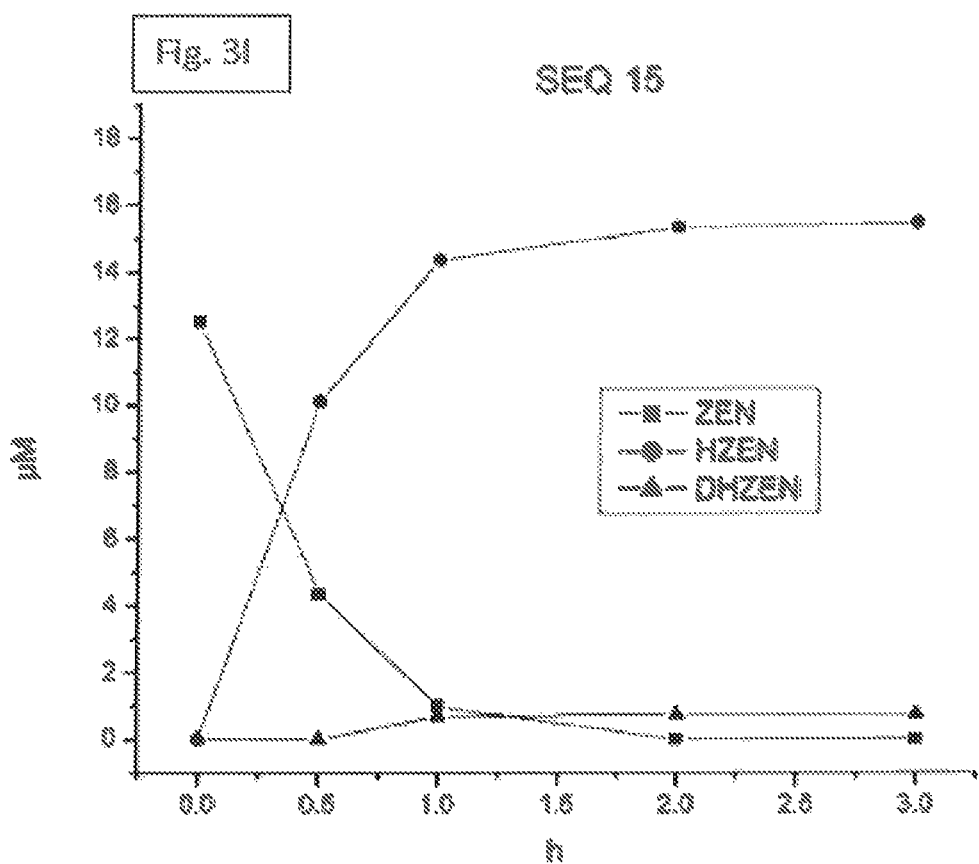

SEQUENCE LISTING

<160> NUMBER OF SEQ ID NOS: 69

<210> SEQ ID NO 1
<211> LENGTH: 328
<212> TYPE: PRT
<213> ORGANISM: Rhodococcus erythropolis

<400> SEQUENCE: 1

Met Ala Glu Glu Gly Thr Arg Ser Glu Ala Ala Asp Ala Ala Thr Gln
1               5                   10                  15

Ala Arg Gln Leu Pro Asp Ser Arg Asn Ile Phe Val Ser His Arg Phe
            20                  25                  30

Pro Glu Arg Gln Val Asp Leu Gly Glu Val Val Met Asn Phe Ala Glu
        35                  40                  45

Ala Gly Ser Pro Asp Asn Pro Ala Leu Leu Leu Leu Pro Glu Gln Thr
    50                  55                  60

Gly Ser Trp Trp Ser Tyr Glu Pro Val Met Gly Leu Leu Ala Glu Asn
65                  70                  75                  80

Phe His Val Phe Ala Val Asp Ile Arg Gly Gln Gly Arg Ser Thr Trp
                85                  90                  95

Thr Pro Arg Arg Tyr Ser Leu Asp Asn Phe Gly Asn Asp Leu Val Arg
            100                 105                 110

Phe Ile Ala Leu Val Ile Lys Arg Pro Val Val Val Ala Gly Asn Ser
        115                 120                 125

Ser Gly Gly Leu Leu Ala Ala Trp Leu Ser Ala Tyr Ala Met Pro Gly
    130                 135                 140

Gln Ile Arg Ala Ala Leu Cys Glu Asp Ala Pro Phe Phe Ala Ser Glu
145                 150                 155                 160

Leu Val Pro Ala Tyr Gly His Ser Val Leu Gln Ala Ala Gly Pro Ala
                165                 170                 175

Phe Glu Leu Tyr Arg Asp Phe Leu Gly Asp Gln Trp Ser Ile Gly Asp
            180                 185                 190

Trp Lys Gly Phe Val Glu Ala Ala Lys Ala Ser Pro Ala Lys Ala Met
        195                 200                 205

Gln Leu Phe Pro Thr Pro Asp Glu Ala Pro Gln Asn Leu Lys Glu Tyr

```
            210                 215                 220
Asp Pro Glu Trp Gly Arg Ala Phe Phe Glu Gly Thr Val Ala Leu His
225                 230                 235                 240

Cys Pro His Asp Arg Met Leu Ser Gln Val Lys Thr Pro Ile Leu Ile
                245                 250                 255

Thr His His Ala Arg Thr Ile Asp Pro Glu Thr Gly Glu Leu Leu Gly
            260                 265                 270

Ala Leu Ser Asp Leu Gln Ala Glu His Ala Gln Asp Ile Ile Arg Ser
            275                 280                 285

Ala Gly Val Arg Val Asp Tyr Gln Ser His Pro Asp Ala Leu His Met
            290                 295                 300

Met His Leu Phe Asp Pro Ala Arg Tyr Ala Glu Ile Leu Thr Ser Trp
305                 310                 315                 320

Ser Ala Thr Leu Pro Ala Asn Asp
                325

<210> SEQ ID NO 2
<211> LENGTH: 308
<212> TYPE: PRT
<213> ORGANISM: Streptomyces violaceusniger

<400> SEQUENCE: 2

Met Ala Asp Pro Ala Gln Arg Asp Val Tyr Val Pro His Ala Tyr Pro
1               5                   10                  15

Glu Lys Gln Ala Asp Leu Gly Glu Ile Thr Met Asn Tyr Ala Glu Ala
                20                  25                  30

Gly Glu Pro Asp Met Pro Ala Val Leu Leu Ile Pro Glu Gln Thr Gly
            35                  40                  45

Ser Trp Trp Gly Tyr Glu Glu Ala Met Gly Leu Leu Ala Glu Asn Phe
        50                  55                  60

His Val Tyr Ala Val Asp Leu Arg Gly Gln Gly Arg Ser Ser Trp Ala
65                  70                  75                  80

Pro Lys Arg Tyr Ser Leu Asp Asn Phe Gly Asn Asp Leu Val Arg Phe
                85                  90                  95

Ile Ala Leu Val Val Lys Arg Pro Val Ile Val Ala Gly Asn Ser Ser
            100                 105                 110

Gly Gly Val Leu Ala Ala Trp Leu Ser Ala Tyr Ser Met Pro Gly Gln
        115                 120                 125

Val Arg Gly Ala Leu Cys Glu Asp Ala Pro Phe Phe Ala Ser Glu Leu
130                 135                 140

Val Thr Thr Cys Gly His Ser Ile Arg Gln Ala Ala Gly Pro Met Phe
145                 150                 155                 160

Glu Leu Phe Arg Thr Tyr Leu Gly Asp Gln Trp Ser Val Gly Asp Trp
                165                 170                 175

Thr Gly Tyr Cys Arg Ala Ala Asp Ala Ser Ser Ser Pro Met Ala Arg
            180                 185                 190

Tyr Phe Val Ala Asp Glu Ile Pro Gln His Met Arg Glu Tyr Asp Pro
        195                 200                 205

Glu Trp Ala Arg Ala Phe Trp Glu Gly Thr Val Ala Leu His Cys Pro
    210                 215                 220

His Glu Gln Leu Leu Thr Gln Val Lys Thr Pro Val Leu Leu Thr His
225                 230                 235                 240

His Met Arg Asp Ile Asp Pro Asp Thr Gly His Leu Val Gly Ala Leu
                245                 250                 255
```

```
Ser Asp Glu Gln Ala Ala Arg Ala Arg Leu Leu Met Glu Ser Ala Gly
            260                 265                 270

Val Lys Val Asp Tyr Ala Ser Val Pro Asp Ala Leu His Met Met His
        275                 280                 285

Gln Phe Asp Pro Pro Arg Tyr Val Glu Ile Phe Thr Gln Trp Ala Ala
        290                 295                 300

Thr Leu Ala Ala
305

<210> SEQ ID NO 3
<211> LENGTH: 309
<212> TYPE: PRT
<213> ORGANISM: Streptomyces coelicolor

<400> SEQUENCE: 3

Met Val Thr Ser Pro Ala Leu Arg Asp Val His Val Pro His Ala Tyr
1               5                   10                  15

Pro Glu Gln Gln Val Asp Leu Gly Glu Ile Thr Met Asn Tyr Ala Glu
            20                  25                  30

Ala Gly Asp Pro Gly Arg Pro Ala Val Leu Leu Ile Pro Glu Gln Thr
        35                  40                  45

Gly Ser Trp Trp Ser Tyr Glu Glu Ala Met Gly Leu Leu Ala Glu His
    50                  55                  60

Phe His Val Tyr Ala Val Asp Leu Arg Gly Gln Gly Arg Ser Ser Trp
65                  70                  75                  80

Thr Pro Lys Arg Tyr Ser Leu Asp Asn Phe Gly Asn Asp Leu Val Arg
                85                  90                  95

Phe Ile Ala Leu Val Val Arg Arg Pro Val Val Ala Gly Asn Ser
            100                 105                 110

Ser Gly Gly Val Leu Ala Ala Trp Leu Ser Ala Tyr Ser Met Pro Gly
        115                 120                 125

Gln Ile Arg Gly Val Leu Cys Glu Asp Pro Pro Phe Phe Ala Ser Glu
    130                 135                 140

Leu Val Pro Ala His Gly His Ser Val Arg Gln Gly Ala Gly Pro Val
145                 150                 155                 160

Phe Glu Leu Phe Arg Thr Tyr Leu Gly Asp Gln Trp Ser Val Gly Asp
                165                 170                 175

Trp Glu Gly Phe Arg Ser Ala Ala Asp Ala Ser Ala Ser Pro Met Ala
            180                 185                 190

Arg Ser Phe Val Ala Asp Thr Ile Pro Gln His Leu Lys Glu Tyr Asp
        195                 200                 205

Pro Glu Trp Ala Arg Ala Phe Tyr Glu Gly Thr Val Gly Leu Asn Cys
    210                 215                 220

Pro His Glu Arg Met Leu Asn Arg Val Asn Thr Pro Val Leu Leu Thr
225                 230                 235                 240

His His Met Arg Gly Thr Asp Pro Glu Thr Gly Asn Leu Leu Gly Ala
                245                 250                 255

Leu Ser Asp Glu Gln Ala Ala Gln Val Arg Arg Leu Met Glu Ser Ala
            260                 265                 270

Gly Val Lys Val Asp Tyr Glu Ser Val Pro Asp Ala Ser His Met Met
        275                 280                 285

His Gln Ser Asp Pro Ala Arg Tyr Ala Glu Ile Leu Thr Pro Trp Thr
    290                 295                 300

Ala Ala Leu Ala Pro
305
```

<210> SEQ ID NO 4
<211> LENGTH: 309
<212> TYPE: PRT
<213> ORGANISM: Streptomyces rapamycinicus

<400> SEQUENCE: 4

```
Met Val Thr Ser Pro Ala Leu Arg Asp Val His Val Pro His Ala Tyr
1               5                   10                  15

Pro Glu Gln Gln Val Asp Leu Gly Glu Ile Thr Met Asn Tyr Ala Glu
            20                  25                  30

Ala Gly Asp Pro Asp Arg Pro Ala Val Leu Leu Ile Pro Glu Gln Thr
        35                  40                  45

Gly Ser Trp Trp Ser Tyr Glu Glu Ala Met Gly Leu Leu Ala Glu His
    50                  55                  60

Phe His Val Tyr Ala Val Asp Leu Arg Gly Gln Gly Arg Ser Ser Trp
65                  70                  75                  80

Thr Pro Lys Arg Tyr Ser Leu Asp Asn Phe Gly Asn Asp Leu Val Arg
                85                  90                  95

Phe Ile Ala Leu Val Val Lys Arg Pro Val Val Ala Gly Asn Ser
            100                 105                 110

Ser Gly Gly Val Leu Ala Ala Trp Leu Ser Ala Tyr Ser Met Pro Gly
        115                 120                 125

Gln Leu Arg Gly Val Leu Cys Glu Asp Pro Pro Phe Phe Ala Ser Glu
    130                 135                 140

Leu Val Pro Ala His Gly His Ser Val Arg Gln Gly Ala Gly Pro Val
145                 150                 155                 160

Phe Glu Leu Phe Arg Thr Tyr Leu Gly Asp Gln Trp Ser Val Ser Asp
                165                 170                 175

Trp Glu Gly Phe Cys Arg Ala Ala Gly Ala Ser Ala Ser Pro Met Ala
            180                 185                 190

Arg Ser Phe Val Ala Asp Gly Ile Pro Gln His Leu Lys Glu Tyr Asp
        195                 200                 205

Pro Glu Trp Ala Arg Ala Phe His Gly Thr Val Gly Leu Asn Cys
    210                 215                 220

Pro His Glu Arg Met Leu Gly Arg Val Asn Thr Pro Val Leu Leu Thr
225                 230                 235                 240

His His Met Arg Gly Thr Asp Pro Glu Thr Gly Asn Leu Leu Gly Ala
                245                 250                 255

Leu Ser Asp Glu Gln Ala Ala Gln Ala Arg Leu Leu Met Glu Ser Ala
            260                 265                 270

Gly Val Arg Val Asp Tyr Glu Ser Val Pro Asp Ala Ser His Met Met
        275                 280                 285

His Gln Ser Asp Pro Ala Arg Tyr Ala Glu Ile Phe Thr Arg Trp Ala
    290                 295                 300

Ala Ala Leu Ala Pro
305
```

<210> SEQ ID NO 5
<211> LENGTH: 309
<212> TYPE: PRT
<213> ORGANISM: Streptomyces lividans

<400> SEQUENCE: 5

```
Met Val Thr Ser Pro Ala Leu Arg Asp Val His Val Pro His Ala Tyr
1               5                   10                  15
```

Pro Glu Gln Gln Val Asp Leu Gly Glu Ile Thr Met Asn Tyr Ala Glu
             20                  25                  30

Ala Gly Asp Pro Gly Arg Pro Ala Val Leu Leu Ile Pro Glu Gln Thr
         35                  40                  45

Gly Ser Trp Trp Ser Tyr Glu Glu Ala Met Gly Leu Leu Ala Glu His
     50                  55                  60

Phe His Val Tyr Ala Val Asp Leu Arg Gly Gln Gly Arg Ser Ser Trp
65                  70                  75                  80

Thr Pro Lys Arg Tyr Ser Leu Asp Asn Phe Gly Asn Asp Leu Val Arg
             85                  90                  95

Phe Met Ala Leu Val Val Arg Arg Pro Val Val Ala Gly Asn Ser
            100                 105                 110

Ser Gly Gly Val Leu Ala Ala Trp Leu Ser Ala Tyr Ser Met Pro Gly
        115                 120                 125

Gln Ile Arg Gly Val Leu Cys Glu Asp Pro Pro Phe Phe Ala Ser Glu
    130                 135                 140

Leu Val Pro Ala His Gly His Ser Val Arg Gln Gly Ala Gly Pro Val
145                 150                 155                 160

Phe Glu Leu Phe Arg Thr Tyr Leu Gly Asp Gln Trp Ser Val Gly Asp
                165                 170                 175

Trp Glu Gly Phe Arg Ser Ala Ala Gly Ala Ser Ala Ser Pro Met Ala
            180                 185                 190

Arg Ser Phe Val Ala Asp Thr Ile Pro Gln His Leu Lys Glu Tyr Asp
        195                 200                 205

Pro Glu Trp Ala Arg Ala Phe Tyr Glu Gly Thr Val Gly Leu Asn Cys
    210                 215                 220

Pro His Glu Arg Met Leu Asn Arg Val Asn Thr Pro Val Leu Leu Thr
225                 230                 235                 240

His His Met Arg Gly Thr Asp Pro Glu Thr Gly Asn Leu Leu Gly Ala
                245                 250                 255

Leu Ser Asp Glu Gln Ala Ala Gln Ala Arg Arg Leu Met Glu Ser Ala
            260                 265                 270

Gly Val Lys Val Asp Tyr Glu Ser Val Pro Asp Ala Ser His Met Met
        275                 280                 285

His Gln Ser Asp Pro Ala Arg Tyr Ala Glu Ile Leu Thr Pro Trp Ala
    290                 295                 300

Ala Ala Leu Ala Pro
305

<210> SEQ ID NO 6
<211> LENGTH: 309
<212> TYPE: PRT
<213> ORGANISM: Streptomyces coelicoflavus

<400> SEQUENCE: 6

Met Val Thr Ser Pro Ala Leu Arg Asp Val His Val Pro His Ala Tyr
1               5                   10                  15

Pro Glu Gln Gln Val Asp Leu Gly Glu Ile Thr Met Asn Tyr Ala Glu
             20                  25                  30

Ala Gly Asp Pro Asp Arg Pro Ala Val Leu Leu Ile Pro Glu Gln Thr
         35                  40                  45

Gly Ser Trp Trp Ser Tyr Glu Glu Ala Met Gly Leu Leu Ser Glu His
     50                  55                  60

Phe His Val Tyr Ala Val Asp Leu Arg Gly Gln Gly Arg Ser Ser Trp

```
                65                  70                  75                  80
        Thr Pro Lys Arg Tyr Ser Leu Asp Asn Phe Gly Asn Asp Leu Val Arg
                            85                  90                  95

Phe Ile Ala Leu Val Val Lys Arg Pro Val Val Ala Gly Asn Ser
                        100                 105                 110

Ser Gly Gly Val Leu Ala Ala Trp Leu Ser Ala Tyr Ser Met Pro Gly
                        115                 120                 125

Gln Leu Arg Gly Val Leu Cys Glu Asp Pro Pro Phe Phe Ala Ser Glu
                130                 135                 140

Leu Val Pro Ala His Gly His Ser Val Arg Gln Gly Ala Gly Pro Val
        145                 150                 155                 160

Phe Glu Leu Phe Arg Thr Tyr Leu Gly Asp Gln Trp Ser Val Gly Asp
                            165                 170                 175

Trp Glu Gly Phe Cys Arg Ala Ala Gly Ala Ser Ala Ser Pro Met Ala
                        180                 185                 190

Arg Ser Phe Val Ala Asp Gly Ile Pro Gln His Leu Gln Glu Tyr Asp
                        195                 200                 205

Pro Glu Trp Ala Arg Val Phe Tyr Glu Gly Thr Val Gly Leu Ser Cys
                210                 215                 220

Pro His Glu Arg Met Leu Gly Gln Val Lys Thr Pro Val Leu Leu Thr
        225                 230                 235                 240

His His Met Arg Gly Ile Asp Pro Glu Thr Gly Asn Leu Leu Gly Ala
                            245                 250                 255

Leu Ser Asp Glu Gln Ala Leu Arg Ala Arg Leu Met Asp Ser Ala
                        260                 265                 270

Gly Val Thr Val Asp Tyr Glu Ser Val Pro Asp Ala Ser His Met Met
                        275                 280                 285

His Gln Ser Ala Pro Ala Arg Tyr Val Glu Ile Phe Thr Arg Trp Ala
                290                 295                 300

Ala Ala Leu Ala Pro
        305

<210> SEQ ID NO 7
<211> LENGTH: 300
<212> TYPE: PRT
<213> ORGANISM: Rhodococcus triatome

<400> SEQUENCE: 7

Met Pro His Asp Tyr Glu Glu Lys Leu Val Asp Leu Gly Glu Ile Asp
        1               5                   10                  15

Leu Asn Tyr Ala Glu Ala Gly Ser Pro Asp Lys Pro Ala Leu Leu Leu
                        20                  25                  30

Ile Pro Ser Gln Ser Glu Ser Trp Trp Gly Tyr Glu Glu Ala Met Gly
                    35                  40                  45

Leu Leu Ala Glu Asp Tyr His Val Phe Ala Val Asp Met Arg Gly Gln
        50                  55                  60

Gly Arg Ser Thr Trp Thr Pro Gly Arg Tyr Ser Leu Asp Asn Phe Gly
        65                  70                  75                  80

Asn Asp Leu Val Arg Phe Ile Asp Leu Val Ile Gly Arg Thr Val Ile
                            85                  90                  95

Val Ser Gly Asn Ser Ser Gly Gly Val Val Ala Ala Trp Leu Ala Ala
                        100                 105                 110

Phe Ser Leu Pro Gly Gln Val Arg Ala Ala Leu Ala Glu Asp Ala Pro
                        115                 120                 125
```

```
Phe Phe Ala Ser Glu Leu Asp Pro Lys Val Gly His Thr Ile Arg Gln
    130                 135                 140

Ala Ala Gly His Ile Phe Val Asn Trp Arg Asp Tyr Leu Gly Asp Gln
145                 150                 155                 160

Trp Ser Val Gly Asp Tyr Ala Gly Phe Leu Lys Ala Met Lys Ser Ser
                165                 170                 175

Glu Val Pro Met Leu Arg Gln Val Pro Leu Pro Glu Thr Ala Pro Gln
            180                 185                 190

Asn Leu Leu Glu Tyr Asp Pro Glu Trp Ala Arg Ala Phe Tyr Glu Gly
        195                 200                 205

Thr Val Ala Gln Thr Cys Pro His Asp Tyr Met Leu Ser Gln Val Lys
210                 215                 220

Val Pro Met Leu Val Thr His His Ala Arg Met Ile Asp Glu Ala Thr
225                 230                 235                 240

Ser Gly Leu Val Gly Ala Met Ser Asp Leu Gln Val Gln Lys Ala Ala
                245                 250                 255

Glu Ile Ile Arg Gly Thr Gly Val Gln Val Asp Val Val Asp Leu Pro
            260                 265                 270

Glu Ala Pro His Ile Leu His Gln Leu Ala Pro Lys Glu Tyr Val Glu
        275                 280                 285

Ile Leu Asn Asn Trp Val Glu Lys Leu Pro Pro Val
290                 295                 300

<210> SEQ ID NO 8
<211> LENGTH: 307
<212> TYPE: PRT
<213> ORGANISM: Hirschia baltica

<400> SEQUENCE: 8

Met Ile Gln Asn Asn Lys Thr Ala Pro Tyr Lys Tyr Lys Glu Lys Leu
1               5                   10                  15

Val Asp Leu Gly Glu Ile Lys Met Asn Tyr Ile Val Ala Gly Ala Asp
            20                  25                  30

Val Ser Pro Ala Leu Leu Leu Ile Pro Gly Gln Thr Glu Ser Trp Trp
        35                  40                  45

Gly Phe Glu Ala Ala Ile Glu Lys Leu Glu Ser Asn Phe Gln Val Phe
    50                  55                  60

Ala Ile Asp Leu Arg Gly Gln Gly Lys Ser Thr Gln Thr Pro Gly Arg
65                  70                  75                  80

Tyr Ser Leu Asn Leu Met Gly Asn Asp Leu Val Arg Phe Ile Ser Leu
                85                  90                  95

Val Ile Lys Arg Pro Val Ile Val Ser Gly Asn Ser Ser Gly Gly Leu
            100                 105                 110

Leu Ala Ala Trp Leu Ser Ala Tyr Ala Met Pro Asn Gln Ile Arg Ala
        115                 120                 125

Ile His Cys Glu Asp Ala Pro Phe Phe Thr Ala Glu Lys Ala Pro Leu
    130                 135                 140

Tyr Gly His Ala Ile Gln Gln Ala Gly Pro Ile Phe Ser Leu Met
145                 150                 155                 160

Ser Lys Phe Leu Gly Asp Gln Trp Ser Ile Asn Asn Trp Glu Gly Leu
                165                 170                 175

Lys Ala Ala Gln Ala Lys Asp Thr His Pro Ala Asn Lys Met Ile Ser
            180                 185                 190

Gln Val Glu Gln Pro Pro Gln His Leu Lys Glu Tyr Asp Pro Glu Trp
        195                 200                 205
```

```
Gly Arg Ala Phe Ile Glu Gly Lys Phe Asn Leu Asn Ser Pro His His
    210                 215                 220

Thr Leu Leu Ser Asp Ile Lys Thr Pro Met Leu Tyr Thr His His Met
225                 230                 235                 240

Arg Phe Glu Asp Pro Gln Thr Gly Leu Leu Ile Gly Ala Thr Ser Asp
                245                 250                 255

Phe Gln Ala Ser Lys Ile Lys Glu Ile Ala Leu Lys Thr Gly Asn Ser
                260                 265                 270

Phe Glu Leu Ile Asp Ala Pro Asp Ala Phe His Ser Met His Glu Ala
                275                 280                 285

Asp Pro Gln Arg Phe Val Asp Ile Leu Thr Ser Trp Ile Glu Arg Leu
                290                 295                 300

Asn Leu Gln
305

<210> SEQ ID NO 9
<211> LENGTH: 321
<212> TYPE: PRT
<213> ORGANISM: Nocardia brasiliensis

<400> SEQUENCE: 9

Met Gly Ile Ser Glu Ala Ala Asp Arg Ala Asp Thr Phe Val Ala His
1               5                   10                  15

Lys Phe Glu Glu Gln Leu Val Asp Leu Gly Ile Arg Met Asn Tyr
                20                  25                  30

Val Ala Ala Gly Asp Pro Thr Ser Pro Ala Leu Leu Leu Ile Pro Ala
            35                  40                  45

Gln Gly Glu Ser Trp Trp Gly Tyr Glu Asn Ala Ile Thr Leu Leu Ala
50                  55                  60

Asn Asp Phe Arg Val Phe Ala Ile Asp Leu Arg Gly Gln Gly Arg Ser
65                  70                  75                  80

Thr Trp Thr Pro Gly Arg Tyr Asn Leu Asn Thr Trp Gly Asn Asp Val
                85                  90                  95

Glu Arg Phe Ile Asp Leu Val Ile Gly Arg Pro Thr Leu Val Ala Gly
                100                 105                 110

Asn Ser Ser Gly Gly Val Ile Ala Ala Trp Leu Ala Ala Tyr Ala Lys
            115                 120                 125

Pro Gly Gln Ile Arg Gly Ala Met Leu Glu Asp Pro Pro Leu Phe Ala
130                 135                 140

Ser Gln Ala Ala Pro Pro Tyr Gly Pro Gly Ile Met Gln Thr Leu Gly
145                 150                 155                 160

Pro Ile Phe Val Leu Trp Ala Lys Trp Leu Gly Pro Gln Trp Ser Val
                165                 170                 175

Gly Asp Trp Asp Gly Met Val Ala Ala Pro Arg Glu Leu Pro Glu
                180                 185                 190

Phe Leu His Pro Gly Ile Ala Phe Leu Phe Gly Asp Gly Thr Gly Glu
            195                 200                 205

Gly Ala Ala Ala Thr Pro Pro Gln His Leu Lys Glu Tyr Asp Pro Glu
210                 215                 220

Trp Ala Gln Ala Trp Ala Thr Asp Val Ala Asn Ala Gly Cys Asp His
225                 230                 235                 240

Ala Thr Met Leu Ala Gln Asn Arg Val Pro Val Leu Leu Thr His His
                245                 250                 255

Phe His Leu Thr Asp Pro Asp Thr Gly Gln Leu Met Gly Ala Met Thr
```

```
                260                 265                 270
Asp Ile Gln Ala Gln Ala Arg Arg Leu Leu Ala Ala Thr Gly Gln
            275                 280                 285

Pro Val Thr Phe Thr Ala Leu Asp Ala Pro His Thr Met His Asp Pro
290                 295                 300

Glu Pro Glu Arg Tyr Phe Glu Val Leu Thr Glu Trp Ala Ser Ala Leu
305                 310                 315                 320

Asp

<210> SEQ ID NO 10
<211> LENGTH: 319
<212> TYPE: PRT
<213> ORGANISM: Mycobacterium vaccae

<400> SEQUENCE: 10

Met Gly Arg Tyr Ala Gly Val Phe Gly Pro His Ala Pro Glu Ser Thr
1               5                   10                  15

Tyr Val Gly His Ala Tyr Pro Glu Gln Leu Phe Asp Thr Gly Glu Val
            20                  25                  30

Arg Leu Asn Tyr Ala Val Ala Gly Asp Ala Ser Ala Ser Pro Leu Leu
        35                  40                  45

Leu Ile Pro Gly Gln Thr Glu Ser Trp Trp Gly Tyr Glu Pro Ala Met
    50                  55                  60

Gly Leu Leu Ala Glu His Phe His Val His Ala Val Asp Leu Arg Gly
65                  70                  75                  80

Gln Gly Arg Ser Thr Arg Thr Pro Arg Arg Tyr Thr Leu Asp Asn Ile
                85                  90                  95

Gly Asn Asp Leu Val Arg Phe Leu Asp Gly Val Ile Gly Arg Pro Ala
            100                 105                 110

Phe Val Ser Gly Leu Ser Ser Gly Gly Leu Leu Ser Ala Trp Leu Ser
        115                 120                 125

Ala Phe Ala Glu Pro Gly Gln Val Leu Ala Ala Cys Tyr Glu Asp Pro
    130                 135                 140

Pro Phe Phe Ser Ser Glu Leu Asp Pro Val Ile Gly Pro Gly Leu Met
145                 150                 155                 160

Ser Thr Val Gly Pro Leu Phe Ala Leu Tyr Val Lys Tyr Leu Gly Asp
                165                 170                 175

Gln Trp Ser Ile Gly Asp Trp Asp Gly Phe Val Ala Gly Ala Pro Gln
            180                 185                 190

Glu Leu Ala Gly Trp Gln Ala His Val Ala Leu Ala Gly Gly Thr Ala
        195                 200                 205

Glu Pro Pro Gln His Leu Lys Glu Tyr Asp Pro Glu Trp Gly Arg Ala
    210                 215                 220

Phe Val Gly Gly Thr Phe Thr Thr Gly Cys Pro His Gln Val Met Leu
225                 230                 235                 240

Ser Gln Val Lys Val Pro Val Leu Phe Thr His His Phe Arg Met Leu
                245                 250                 255

Asp Asp Glu Ser Gly Ser Leu Ile Gly Ala Ala Thr Asp Asp Gln Ala
            260                 265                 270

Ala Arg Val Val Glu Leu Val Glu Asn Ser Gly Ala Pro Leu Thr Tyr
        275                 280                 285

Arg Ser Phe Pro Met Met Gly His Ser Met His Ala Gln Asp Pro Ala
    290                 295                 300

Leu Phe Ala Gly Thr Leu Val Asp Trp Phe Thr Ala Ala Arg Ser
```

```
                305                 310                 315

<210> SEQ ID NO 11
<211> LENGTH: 319
<212> TYPE: PRT
<213> ORGANISM: Mycobacterium gilvum

<400> SEQUENCE: 11

Met Gly Arg Tyr Ala Gly Val Phe Gly Pro His Ala Pro Glu Ala Thr
1               5                   10                  15

Tyr Val Glu His Gly Tyr Pro Glu Arg Leu Phe Asp Thr Gly Glu Val
            20                  25                  30

Gln Leu Asn Tyr Val Val Ala Gly Asp Ala Ala Ala Pro Pro Leu Leu
        35                  40                  45

Leu Ile Pro Gly Gln Ser Glu Ser Trp Trp Gly Tyr Glu Ala Ala Ile
    50                  55                  60

Pro Leu Leu Ala Arg His Phe His Val His Ala Val Asp Leu Arg Gly
65                  70                  75                  80

Gln Gly Arg Ser Thr Arg Thr Pro Gly Arg Tyr Thr Leu Asp Asn Val
                85                  90                  95

Gly Asn Asp Leu Val Arg Phe Leu Asp Gly Val Ile Gly Arg Pro Ala
            100                 105                 110

Phe Val Ser Gly Leu Ser Ser Gly Gly Leu Ala Ser Ala Trp Leu Ser
        115                 120                 125

Ala Phe Ala Lys Pro Gly Gln Val Ala Ala Cys Trp Glu Asp Pro
    130                 135                 140

Pro Phe Phe Ser Ser Glu Thr Ala Pro Ile Val Gly Pro Pro Ile Thr
145                 150                 155                 160

Asp Ser Ile Gly Pro Leu Phe Gly Met Trp Ala Arg Tyr Leu Gly Asp
                165                 170                 175

Gln Trp Ser Val Gly Asp Trp Asp Gly Phe Val Ala Ala Val Pro Thr
            180                 185                 190

Glu Leu Ala Asp Trp Gln Ala His Val Ala Leu Val Val Gly Thr Ala
        195                 200                 205

Asp Pro Pro Gln Asn Leu Arg Glu Tyr Asp Pro Glu Trp Gly Lys Ala
    210                 215                 220

Phe Ile Thr Gly Thr Phe Ala Ala Ser Cys Pro His His Val Met Leu
225                 230                 235                 240

Ser Lys Val Lys Val Pro Val Leu Tyr Thr His His Phe Arg Met Ile
                245                 250                 255

Asp Glu Gly Ser Gly Gly Leu Ile Gly Ala Cys Ser Asp Ile Gln Ala
            260                 265                 270

Gly Arg Val Thr Gln Leu Ala Lys Ser Gly Arg Ser Val Thr Tyr
        275                 280                 285

Arg Ser Phe Pro Met Met Ala His Ser Met His Gly Gln Asp Pro Ala
    290                 295                 300

Leu Phe Ser Glu Thr Leu Val Glu Trp Phe Ser Arg Phe Thr Gly
305                 310                 315

<210> SEQ ID NO 12
<211> LENGTH: 322
<212> TYPE: PRT
<213> ORGANISM: Gordonia effusa

<400> SEQUENCE: 12

Met Pro Lys Ser Glu Ala Ala Asp Arg Ala Asp Ser Phe Val Ser His
```

```
  1               5                  10                 15
Asp Phe Lys Glu Asn Ile Val Asp Leu Gly Glu Ile Arg Met Asn Tyr
             20                 25                 30

Val Val Gln Gly Asn Lys Lys Ser Pro Ala Leu Leu Ile Pro Ala
             35                 40                 45

Gln Gly Glu Ser Trp Trp Gly Tyr Glu Ala Ala Ile Pro Leu Leu Ala
             50                 55                 60

Lys His Phe Gln Val Phe Ala Ile Asp Leu Arg Gly Gln Gly Arg Thr
 65              70                 75                 80

Thr Trp Thr Pro Gly Arg Tyr Thr Leu Asp Ile Phe Gly Asn Asp Val
                 85                 90                 95

Val Arg Phe Ile Asp Leu Val Ile Gly Arg Glu Thr Leu Ile Ala Gly
                100                105                110

Asn Ser Ser Gly Gly Leu Ile Gly Ala Trp Leu Ala Ala Phe Ala Lys
                115                120                125

Pro Gly Gln Val Arg Ala Val Met Leu Glu Asp Pro Pro Leu Phe Ala
                130                135                140

Ser Glu Ile Arg Pro Pro Tyr Gly Pro Gly Ile Trp Gln Gly Leu Gly
145                150                155                160

Pro Met Phe Ala Ala Trp Ala Lys Trp Leu Gly Pro Gln Trp Ser Ile
                165                170                175

Gly Asp Trp Asp Gly Met Val Lys Ala Leu Pro Asp Glu Leu Pro Glu
                180                185                190

Asp Leu Leu Pro Gly Ile Gly Phe Met Leu Gly Asp Gly Glu Ser Asp
                195                200                205

Gly Ala Ala Pro Thr Pro Pro Gln His Leu Lys Glu Tyr Asp Pro Glu
                210                215                220

Trp Gly Ala Ser Trp Ala Ser Gly Phe Ala Asn Thr Gly Cys Glu His
225                230                235                240

Glu Ala Val Ile Ser Gln Val Arg Val Pro Val Leu Thr His His
                245                250                255

Phe Arg Gln Ile Asn Glu Glu Thr Gly His Leu Met Gly Ala Leu Ser
                260                265                270

Asp Leu Gln Ala Ala Gln Val Arg His Ile Ile Glu Glu Val Ala Gly
                275                280                285

Gln Glu Val Thr Tyr Val Ser Leu Asp Ala Pro His Thr Met His Glu
                290                295                300

Pro Gln Pro Glu Arg Tyr Thr Asp Val Leu Leu Asp Trp Val Lys Lys
305                310                315                320

Leu Gly

<210> SEQ ID NO 13
<211> LENGTH: 328
<212> TYPE: PRT
<213> ORGANISM: Togninia minima

<400> SEQUENCE: 13

Met Asn Tyr Ala Thr Ala Gly Ser Ser Asp Lys Pro Ala Leu Leu Leu
 1               5                 10                 15

Val Pro Gly Gln Ser Glu Ser Trp Trp Gly Tyr Glu Met Ala Met Trp
             20                 25                 30

Leu Leu Lys Asp Asp Tyr Gln Val Phe Ala Val Asp Met Arg Gly Gln
             35                 40                 45

Gly Gln Ser Thr Trp Thr Pro Gly Arg Tyr Ser Leu Asp Thr Phe Gly
```

```
                    50                  55                  60
Asn Asp Leu Val Lys Phe Ile Asp Ile Val Ile Lys Arg Pro Val Val
 65                  70                  75                  80

Val Ser Gly Leu Ser Ser Gly Val Val Ser Ala Trp Leu Ser Ala
                     85                  90                  95

Phe Ala Lys Pro Gly Gln Ile Arg Ala Ala Val Tyr Glu Asp Pro Pro
                    100                 105                 110

Leu Phe Ala Ser Gln Ser Lys Pro Ala Ile Gly Gln Ser Val Met Gln
                    115                 120                 125

Thr Val Ala Gly Pro Phe Phe Asn Leu Trp Tyr Lys Trp Leu Gly Ala
                    130                 135                 140

Gln Trp Thr Ile Gly Asp Gln Ala Gly Met Val Ala Ala Met Pro Lys
145                 150                 155                 160

Glu Ile Pro Ala Trp Ile Leu Gln Tyr Leu Gly Asn Thr Thr Ser Gly
                    165                 170                 175

Pro Thr Gly Leu Asp Leu Thr Leu Asn Glu Tyr Asp Pro Glu Trp Gly
                    180                 185                 190

His Gly Phe Val Ser Gly Thr Val Asp Ala Thr Cys Asp His Glu Ala
                    195                 200                 205

Met Leu Thr His Val Lys Val Pro Val Leu Phe Thr His His Ser Arg
210                 215                 220

Ala Ile Asp Pro Tyr Thr Gly Asn Leu Ile Gly Ser Val Ser Asp Thr
225                 230                 235                 240

Gln Val Ser Tyr Ala Gln Gly Leu Ile Thr Thr Asn Gly Asn Gln Ser
                    245                 250                 255

Phe Thr Leu Lys Asn Phe Pro Leu Ala Ser His Asp Met His Asn Ser
                    260                 265                 270

Asp Pro Ala Thr Tyr Val Ser Ala Ile Thr Thr Trp Met Ala Ser Leu
                    275                 280                 285

Gly Ile Gly Ser Ala Val Ile Pro Gly Pro Val Lys Val Ala Ser Ala
                    290                 295                 300

Ser Ala Gln Val Ser Ala Ala Ser Thr Ala Pro Pro Ser Cys Thr Ser
305                 310                 315                 320

Thr Ser Ala Pro Ser Thr Gly His
                    325

<210> SEQ ID NO 14
<211> LENGTH: 280
<212> TYPE: PRT
<213> ORGANISM: Actinosynnema mirum

<400> SEQUENCE: 14

Met Thr Val Val Asp Pro Pro Ala Pro Arg Asp Phe Pro Glu Leu Leu
  1               5                  10                  15

Val Asp Leu Gly Glu Val Val Leu Asn His Ala Glu Ala Gly Ser Pro
                 20                  25                  30

Asp Arg Pro Ala Leu Val Pro Val Pro Glu Gln Gly Gly Ser Trp Trp
                 35                  40                  45

Ser Tyr Glu Arg Val Met Pro Leu Pro Ala Arg Asp Phe His Val Phe
                 50                  55                  60

Ala Val Asp Leu Arg Gly Arg Gly Arg Ser Thr Arg Thr Pro Arg Arg
 65                  70                  75                  80

Tyr Ser Leu Asp Asp Phe Gly Asn Asp Leu Val Arg Phe Leu Ala Leu
                 85                  90                  95
```

```
Val Val Arg Arg Pro Ala Val Ala Gly Asn Ser Ser Gly Gly Val
            100                 105                 110

Leu Ala Ala Trp Ser Ser Ala Tyr Ala Met Pro Gly Gln Val Arg Ala
            115                 120                 125

Val Leu Leu Glu Asp Pro Pro Leu Phe Ser Ser Glu Leu Thr Pro Val
            130                 135                 140

Cys Gly Pro Gly Val Arg Gln Ala Ala Gly Pro Leu Phe Glu Leu Leu
145                 150                 155                 160

Ser Thr His Leu Gly Asp Gln Trp Gly Gly Gly Arg Pro Gly Arg Val
            165                 170                 175

His Gly Gly Val Pro Arg Leu Gly Leu Ala Ala Ala Ala Val Arg
            180                 185                 190

Val Ala Arg Arg Ala Ala Ala Thr Asp Ala Arg Gly Arg Pro Gly Ala
            195                 200                 205

Ala Arg Gly Arg Pro Ala Gly Val Gly Gly Ala Ala Arg Arg Gly Arg
            210                 215                 220

Gly Gly Arg Glu Arg Thr Gly Thr Thr Val Leu Ser Gly Leu Thr
225                 230                 235                 240

Gly Ser Arg Thr Ser Gly Thr Gly Arg Cys Arg Lys Pro Phe Arg Leu
            245                 250                 255

Arg Gln Trp Trp Ala Gly Gly Ala Arg Gly Pro Pro Pro Arg Gln
            260                 265                 270

Ile Arg Ala Asp Val Arg Thr Arg
            275                 280

<210> SEQ ID NO 15
<211> LENGTH: 326
<212> TYPE: PRT
<213> ORGANISM: Kutzneria albida

<400> SEQUENCE: 15

Met Ser Val Pro Val Thr Pro Ser Ala Arg Asn Val Phe Val Pro His
1               5                   10                  15

Ala Phe Pro Glu Lys Gln Ile Asp Leu Gly Glu Val Val Leu Asn Tyr
            20                  25                  30

Ala Glu Ala Gly Thr Pro Asp Lys Pro Ala Leu Leu Leu Pro Glu
            35                  40                  45

Gln Thr Gly Ser Trp Trp Ser Tyr Glu Pro Ala Met Gly Leu Leu Ala
            50                  55                  60

Glu His Phe His Val Phe Ala Val Asp Leu Arg Gly Gln Gly Arg Ser
65                  70                  75                  80

Thr Trp Thr Pro Gly Arg Tyr Ser Leu Asp Asn Phe Gly Asn Asp Leu
            85                  90                  95

Val Arg Phe Ile Ala Leu Ala Ile Arg Arg Pro Val Val Val Ala Gly
            100                 105                 110

Cys Ser Ser Gly Gly Val Leu Ala Ala Trp Leu Ser Ala Tyr Ala Leu
            115                 120                 125

Pro Gly Gln Ile Arg Gly Ala Leu Cys Glu Asp Ala Pro Leu Phe Ala
            130                 135                 140

Ser Glu Leu Thr Pro Ala His Gly His Gly Val Arg Gln Gly Ala Gly
145                 150                 155                 160

Pro Val Phe Glu Leu Tyr Arg Asp Tyr Leu Gly Asp Gln Trp Ser Val
            165                 170                 175

Gly Asp Trp Ala Gly Leu Val Ala Ala Gln Ala Ser Pro Ala Lys
            180                 185                 190
```

```
Met Met Ser Leu Phe Lys Met Pro Gly Glu Pro Gln Asn Leu Arg
        195                 200                 205

Glu Tyr Asp Pro Glu Trp Ala Arg Val Phe Phe Glu Gly Thr Val Gly
210                 215                 220

Leu His Cys Pro His Asp Arg Met Leu Ser Gln Val Lys Thr Pro Val
225                 230                 235                 240

Leu Ile Thr His His Ala Arg Thr Thr Asp Pro Glu Thr Gly Glu Phe
                245                 250                 255

Leu Gly Ala Leu Ser Glu Leu Gln Ala Glu Arg Ala Gln Ala Ile Ile
                260                 265                 270

Arg Ala Ala Gly Val Pro Val Asp Tyr Gln Ser Phe Pro Asp Ala Ala
                275                 280                 285

His Ala Met His Thr Thr Glu Pro Ala Arg Tyr Ala Ala Val Leu Thr
        290                 295                 300

Ala Trp Ala Ala Lys Leu Pro Pro Val Ala Asp Thr Ser Pro Ser Ala
305                 310                 315                 320

Ala Ala Ser Ala His Val
                325

<210> SEQ ID NO 16
<211> LENGTH: 987
<212> TYPE: DNA
<213> ORGANISM: Rhodococcus erythropolis
<220> FEATURE:
<221> NAME/KEY: misc_feature
<223> OTHER INFORMATION: Artificial DNA sequence encodes polypeptid with
      SEQ ID NO: 1

<400> SEQUENCE: 16
atggccgaag aaggaactag gtccgaagca gcggatgctg ccacacaagc gagacagcta      60
cccgattcgc ggaacatctt tgtctcgcac cgatttccgg aaaggcaggt cgatctcggt     120
gaagtggtga tgaacttcgc ggaggcgggc tctccggaca cccggcact gctcctcctc      180 cccgagcaga ccgggtcgtg gtggagttac gagccagtga tgggtcttct ggcagagaac     240
tttcatgtct tgccgtcga tatccgtggg caaggtcgca gtacctggac gccacggcga      300
tacagcctgg acaacttcgg caatgatctg gtgcgtttca tcgctctggt catcaagcgc     360
cctgtcgtcg tggcagggaa ctcctcgggg gggctgctgg ccgcctggct ctcggcgtac     420
gcgatgcccg ccagatccg tgcagcattg tgtgaggacg caccgttctt tgcgtcggag     480
ttggtccccg catacggtca ctcggttctg caggcggcgg gtccggcatt cgagttgtac     540
cgggacttcc tcggggacca gtggtcgatt ggggactgga aagggttcgt tgaggcagcc     600
aaagcgtcgc cggcaaaggc tatgcaatta tttccgaccc cggatgaggc gccgcagaat     660
ctcaaggaat cgaccccgga atgggggcgc gcattcttcg aagggactgt ggcactgcac     720
tgcccacacg acaggatgct ctcgcaagtc aagacaccaa ttctcatcac tcaccacgcg     780
cggacgatcg acccccgagac gggcgagctg ttgggcgcgc tctccgacct tcaggcagag     840
catgcgcagg acatcattcg gtctgcgggc gttcgggtgg actatcagtc gcaccccgac     900
gcgcttcaca tgatgcatct gttcgatccc gctcgttacg cggagatctt gacatcctgg     960
tccgcaacac tgcctgcgaa cgactag                                         987

<210> SEQ ID NO 17
<211> LENGTH: 987
<212> TYPE: DNA
<213> ORGANISM: Artificial sequence
```

<220> FEATURE:
<223> OTHER INFORMATION: ORF was codon optimized and thus differce from
      natural occuring DNA sequence.

<400> SEQUENCE: 17

| | | | | | |
|---|---|---|---|---|---|
| atggcagaag | aaggcacccg | tagcgaagca | gcagatgcag | caacccaggc | acgtcagctg | 60 |
| ccggatagcc | gtaacatttt | tgttagccat | cgttttccgg | aacgtcaggt | tgatctgggt | 120 |
| gaagttgtta | tgaattttgc | agaagcaggt | agtccggata | tccggcatt | actgctgctg | 180 |
| ccggaacaga | ccggtagttg | gtggtcttat | gaaccggtta | tgggtctgct | ggcagaaaac | 240 |
| tttcatgttt | ttgcagttga | tattcgtggt | cagggtcgta | gcacctggac | accgcgtcgt | 300 |
| tatagcctgg | ataattttgg | taatgatctg | gtgcgtttta | ttgccctggt | tattaaacgt | 360 |
| ccggttgttg | ttgcaggtaa | tagcagcggt | ggcctgctgg | ctgcatggct | gagcgcctat | 420 |
| gcaatgcctg | gtcagattcg | tgcagcactg | tgtgaagatg | caccgttttt | tgcaagcgaa | 480 |
| ctggttcctg | cctatggtca | tagcgttctg | caggcagcag | gtccggcatt | tgaactgtat | 540 |
| cgtgattttc | tgggtgatca | gtggtcaatt | ggtgattgga | aaggttttgt | tgaagcagca | 600 |
| aaagcaagtc | cggctaaagc | aatgcagctg | tttccgacac | cggatgaagc | accgcagaat | 660 |
| ctgaaagaat | atgatccgga | atggggtcgt | gcatttttg | aaggcaccgt | tgcactgcat | 720 |
| tgtccgcatg | atcgtatgct | gagccaggtt | aaaacccga | ttctgattac | ccatcatgca | 780 |
| cgtaccatcg | atccggaaac | cggtgaactg | ctgggtgcac | tgagtgatct | gcaggccgaa | 840 |
| catgcacagg | atattattcg | tagtgccggt | gttcgtgttg | attatcagag | ccatcctgat | 900 |
| gcactgcaca | tgatgcacct | gtttgatccg | gcacgttatg | cagaaattct | gaccagttgg | 960 |
| agcgcaaccc | tgcctgcaaa | tgattaa | | | | 987 |

<210> SEQ ID NO 18
<211> LENGTH: 927
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 2

<400> SEQUENCE: 18

| | | | | | |
|---|---|---|---|---|---|
| atggcagatc | cggcacagcg | tgatgtttat | gttccgcatg | catatccgga | aaaacaggca | 60 |
| gatctgggtg | aaattaccat | gaattatgcc | gaagccggtg | aacctgatat | gcctgcagtt | 120 |
| ctgctgattc | cggaacagac | cggtagttgg | tggggttatg | aagaagcaat | gggtctgctg | 180 |
| gcagaaaact | ttcatgttta | tgcagttgat | ctgcgtggtc | agggtcgtag | cagctgggca | 240 |
| ccgaaacgtt | atagcctgga | taattttggt | aatgatctgg | tgcgttttat | tgccctggtt | 300 |
| gttaaacgtc | cggttattgt | tgcaggtaat | agcagcggtg | tgttctggc | agcatggctg | 360 |
| agcgcatata | gcatgcctgg | tcaggttcgt | ggtgcactgt | gtgaagatgc | accgttttt | 420 |
| gcaagcgaac | tggttaccac | ctgtggtcat | agcattcgtc | aggcagcagg | tccgatgttt | 480 |
| gaactgtttc | gtacctatct | gggcgatcag | tggtcagttg | gtgattggac | cggctattgt | 540 |
| cgtgcagcag | atgcaagcag | cagcccgatg | gcacgttatt | tgttgcaga | tgaaattccg | 600 |
| cagcacatgc | gtgaatatga | tccggaatgg | gcacgtgcat | ttgggaagg | caccgttgca | 660 |
| ctgcattgtc | cgcatgaaca | gctgctgacc | caggttaaaa | caccggtgct | gctgacacat | 720 |

```
cacatgcgcg atattgatcc tgataccggt catctggttg gtgccctgag tgatgaacag    780
gcagcccgtg cacgtctgct gatggaaagt gccggtgtta agttgatta tgcaagcgtt    840 ccggatgcac tgcacatgat gcaccagttt gatccgcctc gttatgttga aatctttacc    900
cagtgggcag caaccctggc agcataa                                        927
```

```
<210> SEQ ID NO 19
<211> LENGTH: 930
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 3

<400> SEQUENCE: 19
```

```
atggttacca gtccggcact gcgtgatgtt catgttccgc atgcatatcc ggaacagcag     60
gttgatctgg gtgaaattac catgaattat gccgaagccg gtgatccggg tcgtccggca    120
gttctgctga tcccggaaca gaccggtagt tggtggtctt atgaagaagc aatgggtctg    180
ctggcagaac attttcatgt ttatgcagtt gatctgcgtg gtcagggtcg tagcagctgg    240
accccgaaac gttatagcct ggataatttt ggtaatgatc tggtgcgttt tattgccctg    300
gttgttcgtc gtccggttgt tgttgcaggt aatagcagcg gtggtgttct ggcagcatgg    360
ctgagcgcat atagcatgcc tggtcagatt cgtggtgtgc tgtgtgaaga tccgcctttt    420
tttgcaagcg aactggttcc ggcacatggt catagcgttc gtcagggtgc aggtccggtt    480
tttgaactgt ttcgtaccta tctgggcgat cagtggtcag ttggtgattg ggaaggtttt    540
cgtagcgcag cagatgcaag cgcaagcccg atggcacgta gctttgttgc agataccatt    600
ccgcagcatc tgaaagaata tgatccggaa tgggcacgtg cattttatga aggcaccgtt    660
ggtctgaatt gtccgcatga acgtatgctg aatcgtgtta atacaccggt gctgctgacc    720
catcacatgc gtggcaccga tccggaaacc ggtaatctgc tgggtgcact gagtgatgaa    780
caggcagcac aggtgcgtcg tctgatggaa agtgccggtg ttaaagttga ttatgaaagc    840
gttccggatg caagccacat gatgcaccag agcgatccgg cacgttatgc agaaattctg    900
accccgtgga ccgcagcact ggcaccgtaa                                     930
```

```
<210> SEQ ID NO 20
<211> LENGTH: 930
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 4

<400> SEQUENCE: 20
```

```
atggttacca gtccggcact gcgtgatgtt catgttccgc atgcatatcc ggaacagcag     60
gttgatctgg gtgaaattac catgaattat gccgaagccg gtgatcctga tcgtccggca    120
gttctgctga tcccggaaca gaccggtagt tggtggtcat atgaagaagc aatgggtctg    180
ctggcagaac attttcatgt ttatgcagtt gatctgcgtg gtcagggtcg tagcagctgg    240
accccgaaac gttatagcct ggataatttt ggtaatgatc tggtgcgttt tattgccctg    300
```

```
gttgttaaac gtccggttgt tgttgcaggt aatagcagcg gtggtgttct ggcagcatgg    360
ctgagcgcat atagcatgcc tggtcagctg cgtggtgtgc tgtgtgaaga tccgccttt    420 tttgcaagcg aactggttcc ggcacatggt catagcgttc gtcagggtgc aggtccggtt    480
tttgaactgt ttcgtaccta tctgggcgat cagtggtcag ttagcgattg ggaaggtttt    540
tgtcgtgcag ccggtgcaag cgcaagcccg atggcacgta gctttgttgc agatggtatt    600
ccgcagcatc tgaaagaata tgatccggaa tgggcacgtg catttcatga aggcaccgtt    660
ggtctgaatt gtccgcatga acgtatgctg ggtcgtgtta ataccggt gctgctgacc    720 catcatatgc gtggcaccga tccggaaacc ggtaatctgc tgggtgcact gagtgatgaa    780
caggcagcac aggcacgtct gctgatggaa agtgccggtg ttcgtgttga ttatgaaagc    840
gttccggatg caagccatat gatgcaccag agcgatccgg cacgttatgc agaaatcttt    900
acccgttggg cagcagccct ggcaccgtaa                                     930

<210> SEQ ID NO 21
<211> LENGTH: 930
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 5

<400> SEQUENCE: 21
atggttacca gtccggcact gcgtgatgtt catgttccgc atgcatatcc ggaacagcag    60
gttgatctgg gtgaaattac catgaattat gccgaagccg gtgatccggg tcgtccggca    120
gttctgctga tcccggaaca gaccggtagt tggtggtctt atgaagaagc aatgggtctg    180
ctggcagaaa cttttcatgt ttatgcagtt gatctgcgtg gtcagggtcg tagcagctgg    240 acccccgaaac gttatagcct ggataatttt ggtaatgatc tggtgcgttt tatggcactg    300
gttgttcgtc gtccggttgt tgttgcaggt aatagcagcg gtggtgttct ggcagcatgg    360
ctgagcgcat atagcatgcc tggtcagatt cgtggtgtgc tgtgtgaaga tccgccttt    420 tttgcaagcg aactggttcc ggcacatggt catagcgttc gtcagggtgc aggtccggtt    480
tttgaactgt ttcgtaccta tctgggcgat cagtggtcag ttggtgattg ggaaggtttt    540
cgtagcgcag ccggtgcaag cgcaagcccg atggcacgta gctttgttgc agataccatt    600
ccgcagcatc tgaaagaata tgatccggaa tgggcacgtg cattttatga aggcaccgtt    660
ggtctgaatt gtccgcatga acgtatgctg aatcgtgtta ataccggt gctgctgacc    720 catcacatgc gtggcaccga tccggaaacc ggtaatctgc tgggtgcact gagtgatgaa    780
caggcagcac aggcacgtcg tctgatggaa agtgccggtg ttaaagttga ttatgaaagc    840
gttccggatg caagccacat gatgcaccag agcgatccgg cacgttatgc agaaattctg    900
accccgtggg cagcagccct ggcaccgtaa                                     930

<210> SEQ ID NO 22
<211> LENGTH: 930
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
```

<221> NAME/KEY: misc_feature
<223> OTHER INFORMATION: Artificial DNA sequence encodes polypeptid with
      SEQ ID NO: 6

<400> SEQUENCE: 22

```
atggttacca gtccggcact gcgtgatgtt catgttccgc atgcatatcc ggaacagcag      60
gttgatctgg gtgaaattac catgaattat gccgaagccg gtgatcctga tcgtccggca     120
gttctgctga tcccggaaca gaccggtagt tggtggtctt atgaagaagc aatgggtctg     180
ctgagcgaac attttcatgt ttatgcagtt gatctgcgtg gtcagggtcg tagcagctgg     240
accccgaaac gttatagcct ggataatttt ggtaatgatc tggtgcgttt tattgccctg     300
gttgttaaac gtccggttgt tgttgcaggt aatagcagcg gtggtgttct ggcagcatgg     360
ctgagcgcat atagcatgcc tggtcagctg cgtggtgtgc tgtgtgaaga tccgcctttt     420
tttgcaagcg aactggttcc ggcacatggt catagcgttc gtcagggtgc aggtccggtt     480
tttgaactgt ttcgtaccta tctgggcgat cagtggtcag ttggtgattg gaaggtttt     540
tgtcgtgcag ccggtgcaag cgcaagcccg atggcacgta gctttgttgc agatggtatt     600
ccgcagcatc tgcaagaata tgatccggaa tgggcacgtg ttttttatga aggcaccgtt     660
ggtctgagct gtccgcatga acgtatgctg gtcaggttaa aaacaccggt gctgctgacc     720
catcacatgc gtggtatcga tccggaaacc ggtaatctgc tgggtgcact gagtgatgaa     780
caggccctgc gtgcacgtcg tctgatggat agtgccggtg ttaccgttga ttatgaaagc     840
gttccggatg caagccacat gatgcaccag agcgcaccgg cacgttatgt tgaaatcttt     900
acccgttggg cagcagccct ggcaccgtaa                                      930
```

<210> SEQ ID NO 23
<211> LENGTH: 903
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 7

<400> SEQUENCE: 23

```
atgccgcacg attatgaaga aaaactggtt gatctgggcg aaatcgatct gaattatgca      60
gaagcaggta gtccggataa accggcactg ctgctgattc cgagccagag cgaaagttgg     120
tggggctatg aagaagcaat gggtctgctg gccgaagatt atcatgtttt tgcagttgat     180
atgcgtggtc agggtcgtag cacctggaca ccgggtcgtt atagcctgga taattttggt     240
aatgatctgg tgcgctttat cgatctggtt attggtcgta ccgttattgt tagcggtaat     300
agcagcggtg gtgttgttgc agcatggctg gcagcattta gcctgcctgg tcaggttcgt     360
gcagcactgg cagaagatgc accgtttttt gcaagcgaac tggacccgaa agtgggtcat     420
accattcgtc aggcagcagg tcatattttt gttaactggc gtgattatct gggtgatcag     480
tggtcagttg gtgattatgc aggttttctg aaagcaatga aaagcagcga agttccgatg     540
ctgcgtcagg ttccgctgcc ggaaaccgca ccgcagaatc tgctggaata tgatccggaa     600
tgggcacgtg cattttatga aggcaccgtt gcacagacct gtccgcatga ttatatgctg     660
agccaggtta aagtgcctat gctggttacc catcatgcac gtatgattga tgaagcaacc     720
agcggtctgg ttggtgcaat gagcgatctg caggttcaga aagcagcaga aattattcgt     780
```

```
ggcaccggtg ttcaggttga tgttgttgat ctgccggaag caccgcatat tctgcatcag    840
ctggcaccga agaatatgt ggaaattctg ataactggg tggaaaaact gcctccggtt       900
taa                                                                                                    903
```

<210> SEQ ID NO 24
<211> LENGTH: 924
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 8

<400> SEQUENCE: 24

```
atgatccaga caataaaac cgcaccgtat aaatacaaag aaaaactggt tgatctgggc    60
gaaatcaaaa tgaactatat tgttgccggt gcagatgtta gtccggcact gctgctgatt    120
ccgggtcaga ccgaaagttg gtggggtttt gaagcagcaa ttgagaaact ggaaagcaac    180
tttcaggtgt ttgcaattga tctgcgtggt cagggtaaaa gcacccagac accgggtcgt    240
tatagcctga atctgatggg taatgatctg gttcgtttta ttagcctggt tattaaacgt    300
ccggttattg ttagcggtaa tagcagcggt ggtctgctgg cagcatggct gagcgcctat    360
gcaatgccga atcagattcg tgcaattcat tgtgaagatg caccgttttt taccgcagaa    420
aaagcaccgc tgtatggtca tgcaattcag caggcagcag gtccgatttt tagcctgatg    480
agcaaatttc tgggtgatca gtggtcaatt aacaattggg aaggtctgaa agcagcacag    540
gcaaaagata cccatccggc aaacaaaatg attagccagg ttgaacagcc tccgcagcat    600
ctgaaagaat atgatccgga atgggtcgt gcatttattg aaggcaaatt taacctgaac    660
agtccgcatc ataccctgct gagcgacatt aaaaccccga tgctgtatac ccatcacatg    720
cgttttgaag atccgcagac aggtctgctg attggtgcaa ccagcgattt tcaggcaagc    780
aaaatcaaag aaattgccct gaaaaccggc aatagcttcg aactgattga tgcaccggat    840
gcatttcata gtatgcatga agccgatccg cagcgttttg ttgatattct gaccagctgg    900
attgaacgtc tgaatctgca gtaa                                          924
```

<210> SEQ ID NO 25
<211> LENGTH: 966
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 9

<400> SEQUENCE: 25

```
atgggtatta gcgaagcagc agatcgtgca gataccttg ttgcacataa atttgaagaa    60
cagctggttg atctgggtga aattcgtatg aattatgttg cagccggtga tccgaccagt    120
ccggcactgc tgctgattcc ggcacagggt gaaagttggt ggggttatga aaatgcaatt    180
accctgctgg caaatgattt tcgtgttttt gcaattgatc tgcgtggtca gggtcgtagc    240
acctggacac cgggtcgtta taatctgaat acctggggta tgatgtgga acgctttatt    300 gatctggtta ttggtcgtcc gaccctggtt gcaggtaata gcagcggtgg tgttattgca    360
```

```
gcatggctgg cagcctatgc aaaaccgggt cagattcgtg gtgcaatgct ggaagatccg     420
cctctgtttg caagccaggc agcaccgcct tatggtccgg tattatgca gaccctgggt     480 ccgatttttg ttctgtgggc aaaatggctg gtccgcagt ggtcagttgg tgattgggat      540
ggtatggttg cagcggcacc gcgtgaactg ccggaatttc tgcatccggg tatcgcattt     600
ctgtttggtg atggcaccgg tgaaggtgca gcagcaaccc ctccgcagca tctgaaagaa     660
tatgatccgg aatgggcaca ggcatgggca accgatgttg caaatgcagg ttgtgatcat     720
gcaaccatgc tggcacagaa tcgtgttccg gttctgctga cccatcattt tcatctgacc     780
gatccggata caggccagct gatgggtgca atgaccgata ttcaggcaca gcaggcacgt     840
cgtctgctgg cagcaaccgg tcagccggtt acctttaccg cactggatgc accgcatacc     900
atgcatgatc ctgaacctga acgttatttt gaagttctga ccgaatgggc aagtgcactg     960
gattaa                                                               966
```

<210> SEQ ID NO 26
<211> LENGTH: 960
<212> TYPE: DNA
<213> ORGANISM: Artificial sequence
<220> FEATURE:
<223> OTHER INFORMATION: ORF was codon optimized and thus differce from natural occuring DNA sequence.
<220> FEATURE:
<221> NAME/KEY: misc_feature
<223> OTHER INFORMATION: Artificial DNA sequence encodes polypeptid with SEQ ID NO: 10

<400> SEQUENCE: 26

```
atgggtcgtt atgccggtgt ttttggtccg catgcaccgg aaagcaccta tgttggtcat     60
gcatatccgg aacaactgtt tgataccggt gaagttcgtc tgaattatgc agttgccggt    120
gatgcaagcg caagtccgct gctgctgatt ccgggtcaga ccgaaagttg gtggggttat    180
gaaccggcaa tgggtctgct ggcagaacat tttcatgttc atgcagttga tctgcgtggt    240
cagggtcgta gcaccgtac accgcgtcgt tataccctgg ataatattgg taatgatctg    300
gtgcgttttc tggatggtgt tattggtcgt ccggcatttg ttagcggtct gagcagcggt     360
ggtctgctga gcgcatggct gagcgccttt gcagaaccgg tcaggttct ggcagcatgt     420 tatgaagatc cgcctttttt tagcagcgaa ctgaccccgg tgattggtcc gggtctgatg     480
agcaccgttg gtccgctgtt tgcactgtat gttaaatatc tgggtgatca gtggtcaatt     540
ggtgattggg atggttttgt tgcaggcgca ccgcaagaac tggcaggttg caggcacat     600 gttgcactgg caggcggtac agcagaaccg cctcagcatc tgaaagaata tgatccggaa     660
tggggtcgtg catttgttgg tggcaccttt accaccggtt gtccgcatca ggttatgctg     720
agccaggtta aagttccggt tctgtttacc catcattttc gtatgctgga tgatgaaagc     780
ggtagcctga ttggtgcagc aaccgatgat caggcagcac gtgttgttga actggttgaa     840
aatagtggtg caccgctgac ctatcgtagc tttccgatga tgggtcatag tatgcatgca     900
caagatccgg cactgtttgc aggcaccctg gttgattggt ttaccgcagc acgtagctaa    960
```

<210> SEQ ID NO 27
<211> LENGTH: 960
<212> TYPE: DNA
<213> ORGANISM: Artificial sequence
<220> FEATURE:
<223> OTHER INFORMATION: ORF was codon optimized and thus differce from natural occuring DNA sequence.
<220> FEATURE:

<221> NAME/KEY: misc_feature
<223> OTHER INFORMATION: Artificial DNA sequence encodes polypeptid with
      SEQ ID NO: 11

<400> SEQUENCE: 27

| | | | | | |
|---|---|---|---|---|---|
| atgggtcgtt | atgccggtgt | ttttggtccg | catgcaccgg | aagcaaccta | tgttgaacat | 60 |
| ggttatccgg | aacgtctgtt | tgataccggt | gaagtgcagc | tgaattatgt | tgttgccggt | 120 |
| gatgcagcag | caccgcctct | gctgctgatt | ccgggtcaga | gcgaaagttg | gtggggttat | 180 |
| gaagcagcaa | ttccgctgct | ggcacgtcat | tttcatgttc | atgcagttga | tctgcgtggt | 240 |
| cagggtcgta | gcacccgtac | accgggtcgc | tatcccctgg | ataatgttgg | taatgatctg | 300 |
| gtgcgttttc | tggatggtgt | tattggtcgt | ccggcatttg | ttagcggtct | gagcagcggt | 360 |
| ggtctggcaa | gcgcatggct | gagcgcattt | gcaaaaccgg | tcaggttgt | tgcagcatgt | 420 |
| tgggaagatc | cgcctttttt | tagcagcgaa | accgcaccga | ttgttggtcc | gcctattacc | 480 |
| gatagcattg | gtccgctgtt | tggtatgtgg | gcacgttatc | tgggtgatca | gtggtcagtt | 540 |
| ggtgattggg | atggttttgt | tgccgcagtt | ccgaccgaac | tggcagattg | gcaggcacat | 600 |
| gttgcactgg | ttgttggcac | cgcagatcct | ccgcagaatc | tgcgtgaata | tgatccggaa | 660 |
| tggggtaaag | catttattac | cggcaccttt | gcagcaagct | gtccgcatca | tgttatgctg | 720 |
| agcaaagtta | aagttccggt | tctgtatacc | catcactttc | gcatgattga | tgaaggtagt | 780 |
| ggtggtctga | ttggtgcatg | tagcgatatt | caggcaggtc | gtgttaccca | gctggcaaaa | 840 |
| tcaggtggtc | gtagcgttac | ctatcgtagc | tttccgatga | tggcacatag | catgcatggt | 900 |
| caagatccgg | cactgtttag | cgaaaccctg | gttaatggt | ttagccgttt | taccggttaa | 960 |

<210> SEQ ID NO 28
<211> LENGTH: 969
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 12

<400> SEQUENCE: 28

| | | | | | |
|---|---|---|---|---|---|
| atgccgaaaa | gcgaagcagc | agatcgtgca | gatagctttg | ttagccatga | tttcaaagaa | 60 |
| aacattgtgg | atctgggcga | aatccgcatg | aattatgttg | ttcagggcaa | caaaaaaagt | 120 |
| ccggcactgc | tgctgattcc | ggcacagggt | gaaagttggt | ggggttatga | agcagcaatt | 180 |
| ccgctgctgg | caaaacattt | tcaggttttt | gcaattgatc | tgcgtggtca | gggtcgtacc | 240 |
| acctggacac | cggtcgtta | taccctggat | attttggta | atgatgtggt | gcgctttatc | 300 |
| gatctggtta | ttggtcgtga | accctgatt | gcaggtaata | gcagcggtgg | tctgattggt | 360 |
| gcatggctgg | cagcatttgc | aaaaccgggt | caggttcgtg | cagttatgct | ggaagatccg | 420 |
| cctctgtttg | caagcgaaat | tcgtccgcct | tatggtccgg | tatttggca | gggtctgggt | 480 |
| ccgatgtttg | cagcatgggc | aaaatggctg | gtccgcagt | ggtcaattgg | tgattgggat | 540 |
| ggtatggtta | aagcactgcc | ggatgaactg | ccggaagatc | tgctgcctgg | tattggtttt | 600 |
| atgctgggtg | atggtgaaag | tgatggtgca | gcaccgaccc | ctccgcagca | tctgaaagaa | 660 |
| tatgatccgg | aatggggtgc | aagctgggca | agcggttttg | ccaataccgg | ttgtgaacat | 720 |
| gaagcagtta | ttagccaggt | gcgtgttccg | gttctgctga | cccatcattt | tcgtcagatt | 780 |

```
aatgaagaaa ccggtcatct gatgggtgca ctgagcgatc tgcaggcagc acaggttcgt      840
catatcattg aagaagttgc aggtcaagag gttacctatg ttagcctgga tgcaccgcat      900
accatgcatg aaccgcagcc ggaacgttat accgatgttc tgctggattg ggttaaaaaa      960
ctgggttaa                                                              969
```

<210> SEQ ID NO 29
<211> LENGTH: 987
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 13

<400> SEQUENCE: 29

```
atgaattatg caaccgcagg tagcagcgat aaaccggcac tgctgctggt tccgggtcag       60
agcgaaagtt ggtggggtta tgaaatggca atgtggctgc tgaaagatga ttatcaggtt      120
tttgcagttg atatgcgtgg tcagggtcag agtacctgga caccgggtcg ttatagcctg      180
ataccttttg gtaatgatct ggtgaaattc atcgatatcg tgattaaacg tccggttgtt      240
gttagcggtc tgagcagcgg tggtgttgtg agcgcatggc tgagcgcatt tgcaaaacct      300
ggtcagattc gtgcagcagt ttatgaagat ccgcctctgt ttgcaagcca gagcaaaccg      360
gcaattggtc agagtgttat gcagaccgtt gcaggtccgt ttttttaacct gtggtataaa      420 tggctgggtg cacagtggac cattggtgat caggcaggta tggttgcagc aatgccgaaa      480
gaaattccgg catggattct gcagtatctg ggtaatacca ccgtggtcc gaccggtctg      540 gatctgacac tgaatgaata tgatccggaa tggggtcatg gttttgttag tggcaccgtt      600
gatgcaacct gtgatcatga agcaatgctg acccatgtta aagttccggt tctgtttacc      660
catcatagcc gtgcaattga tccgtatacc ggtaatctga ttggtagcgt tagcgatacc      720
caggttagct atgcacaggg tctgattacc accaatggca atcagagctt taccctgaaa      780
aactttccgc tggcaagcca tgatatgcat aattctgatc cggcaaccta tgttagcgca      840
attaccacct ggatggcaag cctgggtatt ggtagtgcag ttattccggg tccggttaaa      900
gttgcaagcg caagcgcaca ggttagcgca gcaagcaccg caccgcctag ctgtaccagc      960
accagcgcac cgagcaccgg tcattaa                                          987
```

<210> SEQ ID NO 30
<211> LENGTH: 843
<212> TYPE: DNA
<213> ORGANISM: Artificial sequence
<220> FEATURE:
<223> OTHER INFORMATION: ORF was codon optimized and thus differce from
      natural occuring DNA sequence.
<220> FEATURE:
<221> NAME/KEY: misc_feature
<223> OTHER INFORMATION: Artificial DNA sequence encodes polypeptid with
      SEQ ID NO: 14

<400> SEQUENCE: 30

```
atgaccgttg ttgatccgcc tgcaccgcgt gattttccgg aactgctggt tgatctgggt       60
gaagttgttc tgaatcatgc agaagcaggt agtccggatc gtccggcact ggttccggtg      120
ccggaacagg gtggtagttg gtggtcttat gaacgtgtta tgccgctgcc tgcacgcgat      180
tttcatgttt ttgcagttga tctgcgtggt cgtggtcgta gcacccgtac accgcgtcgt      240
```

```
tatagcctgg atgattttgg taatgatctg gttcgttttc tggccctggt tgttcgccgt    300
ccggcagttg ttgcaggtaa tagcagcggt ggtgttctgg cagcatggtc aagcgcctat    360
gcaatgcctg gtcaggttcg tgcagttctg ctggaagatc cgcctctgtt agcagcgaa     420 ctgacaccgg tttgtggtcc gggtgttcgt caggcagcag gtccgctgtt tgaactgctg    480
agcacccatc tgggcgatca gtggggtggt ggtcgtccgg tcgtgttca tggtggcgtt     540 ccgcgtctgg gtctggcagc cgcagcagca gttcgtgttg cacgtcgtgc agcagcaacc    600
gatgcacgtg gtcgccctgg tgcagcacgt ggacgtcctg ccggtgttgg tggtgcagct    660
cgtcgcggtc gcgttggtcg tgaacgcacc ggtacaacca ccgttctgag cggtctgacc    720
ggtagccgta ccagcggcac cggtcgttgt cgtaaaccgt tcgtctgcg tcagtggtgg     780 gcaggcggtg cccgtggtcc tcctccgcct cgtcagattc gcgcagatgt tcgtacccgt    840
taa                                                                  843

<210> SEQ ID NO 31
<211> LENGTH: 981
<212> TYPE: DNA
<213> ORGANISM: Artificial Sequence
<220> FEATURE:
<221> NAME/KEY: misc_feature
<223> OTHER INFORMATION: Artificial DNA sequence encodes polypeptid with
      SEQ ID NO: 15

<400> SEQUENCE: 31
atgagcgttc cggttacccc gagcgcacgt aatgttttg ttccgcatgc atttccagag      60
aaacaaattg atctgggtga agtggttctg aattatgcag aagcaggtac accggataaa    120
ccggcattac tgctgctgcc ggaacagacc ggtagttggt ggtcttatga accggcaatg    180
ggtctgctgg cagaacattt tcatgttttt gcagttgatc tgcgtggtca gggtcgtagc    240
acctggacac cgggtcgtta tagcctggat aattttggta atgatctggt gcgttttatt    300
gcactggcaa ttcgtcgtcc ggttgttgtt gcaggttgta gcagcggtgg tgttctggca    360
gcatggctga gcgcctatgc actgcctggt cagattcgtg gtgcactgtg tgaagatgca    420
ccgctgtttg caagcgaact gacaccggca catggtcatg tgttcgtca gggtgcaggt    480 ccggtttttg aactgtatcg tgattatctg ggcgatcagt ggtcagttgg tgattgggca    540
ggtctggttg cagcagcaca ggcaagtccg gcaaaaatga tgagcctgtt taaaatgcct    600
ggtgaaccgc ctcagaatct gcgtgaatat gatccggaat gggcacgtgt tttttttgaa    660
ggcaccgttg gtctgcattg tccgcatgat cgtatgctga gccaggttaa acaccggtt    720 ctgattaccc atcatgcacg taccaccgat ccggaaaccg gtgaatttct gggtgcactg    780
agcgaactga aggcagaacg tgcacaggcc attattcgtg cagccggtgt tccggttgat    840
tatcagagct ttccggatgc agcacatgca atgcatacca cagaaccggc acgttatgca    900
gcagttctga ccgcatgggc agcaaaactg cctccggttg cagataccag cccgtcagca    960
gcagcaagcg cacatgttta a                                              981

<210> SEQ ID NO 32
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)
```

```
<400> SEQUENCE: 32

Ala Gly Asn Ser Ser Gly Gly
1               5

<210> SEQ ID NO 33
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 33

Arg Thr Ile Asp Pro Glu Thr
1               5

<210> SEQ ID NO 34
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 34

Asp Ala Leu His Met Met His
1               5

<210> SEQ ID NO 35
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 35

Ala Gly Asp Ser Ser Gly Gly
1               5

<210> SEQ ID NO 36
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 36

Ala Gly Asp Ser Ser Leu Gly
1               5

<210> SEQ ID NO 37
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
```

```
<222> LOCATION: (1)..(7)

<400> SEQUENCE: 37

Ala Gly Gln Ser Ser Gly Gly
1               5

<210> SEQ ID NO 38
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 38

Ala Gly His Ser Ser Gly Gly
1               5

<210> SEQ ID NO 39
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 39

Ala Gly Ser Ser Ser Gly Gly
1               5

<210> SEQ ID NO 40
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 40

Ser Gly Asn Ser Ser Gly Gly
1               5

<210> SEQ ID NO 41
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 41

Ser Gly Asp Ser Ser Gly Gly
1               5

<210> SEQ ID NO 42
<211> LENGTH: 7
<212> TYPE: PRT
<213> ORGANISM: Artificial sequence
<220> FEATURE:
<223> OTHER INFORMATION: amino acid motif
<220> FEATURE:
```

```
<221> NAME/KEY: PEPTIDE
<222> LOCATION: (1)..(7)

<400> SEQUENCE: 42

Ser Gly Gln Ser Ser Gly Gly
1               5

<210> SEQ ID NO 43
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 43

Ser Gly His Ser Ser Gly Gly
1               5

<210> SEQ ID NO 44
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 44

Ser Gly Ser Ser Ser Gly Gly
1               5

<210> SEQ ID NO 45
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 45

Arg Thr Ile Asp Pro Glu Thr
1               5

<210> SEQ ID NO 46
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 46

Arg Asp Ile Asp Pro Asp Thr
1               5

<210> SEQ ID NO 47
<211> LENGTH: 7
<212> TYPE: PRT
<213> ORGANISM: Artificial sequence
<220> FEATURE:
<223> OTHER INFORMATION: amino acid motif
```

```
<220> FEATURE:
<221> NAME/KEY: PEPTIDE
<222> LOCATION: (1)..(7)

<400> SEQUENCE: 47

Arg Gly Thr Asp Pro Glu Thr
1               5

<210> SEQ ID NO 48
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 48

Arg Gly Ile Asp Pro Glu Thr
1               5

<210> SEQ ID NO 49
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 49

Asp Ala Leu His Met Met His
1               5

<210> SEQ ID NO 50
<211> LENGTH: 7
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(7)

<400> SEQUENCE: 50

Asp Ala Ser His Met Met His
1               5

<210> SEQ ID NO 51
<211> LENGTH: 11
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(11)

<400> SEQUENCE: 51

Val Val Ala Gly Asn Ser Ser Gly Gly Leu Leu
1               5                   10

<210> SEQ ID NO 52
<211> LENGTH: 11
<212> TYPE: PRT
<213> ORGANISM: Artificial sequence
<220> FEATURE:
```

```
<223> OTHER INFORMATION: amino acid motif
<220> FEATURE:
<221> NAME/KEY: PEPTIDE
<222> LOCATION: (1)..(11)

<400> SEQUENCE: 52

Ile Val Ala Gly Asn Ser Ser Gly Gly Val Leu
1               5                   10

<210> SEQ ID NO 53
<211> LENGTH: 11
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(11)

<400> SEQUENCE: 53

His Ala Arg Thr Ile Asp Pro Glu Thr Gly Glu
1               5                   10

<210> SEQ ID NO 54
<211> LENGTH: 11
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(11)

<400> SEQUENCE: 54

His Met Arg Asp Ile Asp Pro Asp Thr Gly His
1               5                   10

<210> SEQ ID NO 55
<211> LENGTH: 11
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(11)

<400> SEQUENCE: 55

His Met Arg Gly Thr Asp Pro Glu Thr Gly Asn
1               5                   10

<210> SEQ ID NO 56
<211> LENGTH: 11
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(11)

<400> SEQUENCE: 56

His Pro Asp Ala Leu His Met Met His Leu Phe
1               5                   10

<210> SEQ ID NO 57
<211> LENGTH: 11
<212> TYPE: PRT
<213> ORGANISM: Artificial sequence
```

```
<220> FEATURE:
<223> OTHER INFORMATION: amino acid motif
<220> FEATURE:
<221> NAME/KEY: PEPTIDE
<222> LOCATION: (1)..(11)

<400> SEQUENCE: 57

Val Pro Asp Ala Leu His Met Met His Gln Phe
1               5                   10

<210> SEQ ID NO 58
<211> LENGTH: 11
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(11)

<400> SEQUENCE: 58

Val Pro Asp Ala Ser His Met Met His Gln Ser
1               5                   10

<210> SEQ ID NO 59
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 59

Ile Lys Arg Pro Val Val Val Ala Gly Asn Ser Ser Gly Gly Leu Leu
1               5                   10                  15

Ala Ala Trp Leu Ser
            20

<210> SEQ ID NO 60
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 60

Val Lys Arg Pro Val Ile Val Ala Gly Asn Ser Ser Gly Gly Val Leu
1               5                   10                  15

Ala Ala Trp Leu Ser
            20

<210> SEQ ID NO 61
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 61

Val Arg Arg Pro Val Val Val Ala Gly Asn Ser Ser Gly Gly Val Leu
```

```
1               5                   10                  15

Ala Ala Trp Leu Ser
            20

<210> SEQ ID NO 62
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 62

Val Lys Arg Pro Val Val Val Ala Gly Asn Ser Ser Gly Gly Val Leu
1               5                   10                  15

Ala Ala Trp Leu Ser
            20

<210> SEQ ID NO 63
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 63

Ile Leu Ile Thr His His Ala Arg Thr Ile Asp Pro Glu Thr Gly Glu
1               5                   10                  15

Leu Leu Gly Ala Leu
            20

<210> SEQ ID NO 64
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 64

Val Leu Leu Thr His His Met Arg Asp Ile Asp Pro Asp Thr Gly His
1               5                   10                  15

Leu Val Gly Ala Leu
            20

<210> SEQ ID NO 65
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 65

Val Leu Leu Thr His His Met Arg Gly Thr Asp Pro Glu Thr Gly Asn
1               5                   10                  15

Leu Leu Gly Ala Leu
```

```
<210> SEQ ID NO 66
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 66

Val Leu Leu Thr His His Pro Asp Ala Leu His Met Met His Leu Phe
1               5                   10                  15

Leu Leu Gly Ala Leu
            20

<210> SEQ ID NO 67
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 67

Val Asp Tyr Gln Ser His Pro Asp Ala Leu His Met Met His Leu Phe
1               5                   10                  15

Asp Pro Ala Arg Tyr
            20

<210> SEQ ID NO 68
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 68

Val Asp Tyr Ala Ser Val Pro Asp Ala Leu His Met Met His Gln Phe
1               5                   10                  15

Asp Pro Pro Arg Tyr
            20

<210> SEQ ID NO 69
<211> LENGTH: 21
<212> TYPE: PRT
<213> ORGANISM: Artificial sequence
<220> FEATURE:
<223> OTHER INFORMATION: amino acid motif
<220> FEATURE:
<221> NAME/KEY: PEPTIDE
<222> LOCATION: (1)..(21)

<400> SEQUENCE: 69

Val Asp Tyr Glu Ser Val Pro Asp Ala Ser His Met Met His Gln Ser
1               5                   10                  15

Ala Pro Ala Arg Tyr
            20
```

POLYPEPTIDE FOR HYDROLYTIC CLEAVAGE OF ZEARALENONE AND/OR ZEARALENONE DERIVATIVES, ISOLATED POLYNUCLEOTIDE THEREOF AS WELL AS A POLYPEPTIDE CONTAINING AN ADDITIVE, USE OF SAME AS WELL AS A PROCESS

The present invention relates to a polypeptide for hydrolytic cleavage of zearalenone and/or at least one zearalenone derivative, as well as an additive containing such a polypeptide as well as a use of such a polypeptide as well as a method for hydrolytic cleavage of zearalenone and/or at least one zearalenone derivative.

BACKGROUND OF THE INVENTION

Mycotoxins are secondary metabolites produced by filamentary fungi. An important representative of mycotoxins is zearalenone (ZEN), which was previously known as F-2 toxin, which is produced by a variety of *Fusarium* fungi and can be found throughout the world. These fungi infest cultivated plants, among others, such as various types of grain, wherein the fungal infestation usually occurs before the harvest when the growth of the fungi and/or the mycotoxin production may take place before storage or may even take place after harvest, either prior to storage or under improper storage conditions. The FAO has estimated that 25% of agrarian products throughout the world are contaminated with mycotoxins, thus resulting in substantial economic losses. In an international study concluded recently, a total of 23,781 samples were analyzed from January 2009 to December 2011, 81% of them testing positive for at least one mycotoxin and 45% testing positive for ZEN. ZEN has been found in all regions of the world and in all types of grain and feed crops tested, such as corn, soy flour, wheat, wheat bran, DDGS (dried distillers grains with solubles) as well as in finished animal feed mixtures with an incidence of up to 100%.

ZEN is a nonsteroidal estrogenic macrocyclic lactone with the following structural formula, synthesized by way of the polyketide metabolic pathway:

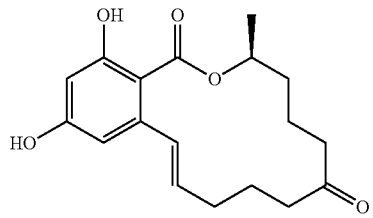

and its name according to the IUPAC nomenclature is (2E,11S)-15,17-dihydroxy-11-methyl-12-oxabicyclo [12.4.0]octadeca-1(18),2,14,16-tetraene-7,13-dione.

However, a variety of ZEN derivatives also occurs in nature and may be formed by enzymatic or chemical modifications of ZEN. Examples include glycosidic ZEN conjugates or those containing sulfate, formed by fungi, plants or a mammalian metabolism as well as ZEN metabolites formed in the human or animal organism, among others. ZEN derivatives are understood below to be ZEN conjugates or ZEN metabolites that occur naturally or are synthesized by chemical or biochemical synthesis but in particular α-zearalenol (α-ZEL; (2E,7R,11S)-7,15,17-trihydroxy-11-methyl-12-oxabicyclo[12.4.0]-octadeca-1(18),2,14,16-tetraen-13-one), β-zearalenol (β-ZEL; (2E,7S,11S)-7,15,17-trihydroxy-11-methyl-12-oxabicyclo[12.4.0]octadeca-1 (18),2,14,16-tetraen-13-one), α-zearalanol (α-ZAL; (7R, 11S)-7,15,17-trihydroxy-11-methyl-12-oxabicyclo[12.4.0] octadeca-1(18),14,16-trien-13-one), β-zearalanol (β-ZAL; (7S,11S)-7,15,17-trihydroxy-11-methyl-12-oxabicyclo [12.4.0]octadeca-1 (14),15,17-trien-13-one), zearalenone 14-sulfate (Z14S; [(2E,11S)-15-hydroxy-11-methyl-7,13-dioxo-12-oxabicyclo[12.4.0]octadeca-1(18),2,14,16-tetraen-17-yl]hydrogen sulfate), zearalenone-14-glycoside (Z14G; (2E,11S)-15-hydroxy-11-methyl-17-[(3R,4S,5S,6R)-3,4,5-trihydroxy-6-(hydroxymethyl)-tetrahydropyran-2-yl]oxy-12-oxabicyclo[12.4.0]octadeca-1(18),2,14,16-tetraene-7, 13-dione) as well as zearalanone (ZAN; (11S)-15,17-dihydroxy-11-methyl-12-oxabicyclo-[12.4.0]octadeca-1 (18),14,16-triene-7,13-dione).

ZEN as well as ZEN derivatives, in particular α-ZEL, β-ZEL, Z14S, α-ZAL, β-ZAL, Z14G and ZAN can also be detected in processed foods and animal feed products, such as bread or beer because of their high chemical and physical stability.

ZEN binds to the estrogen receptor and can cause hormonal disruptions, being absorbed immediately after oral ingestion and converted by mammals into the two stereoisomeric metabolites α-ZEL and/or β-ZEL. For example, α-ZEL but also α-ZAL and/or ZAN have a much stronger estrogenic effect than ZEN. Meanwhile, conjugated ZEN derivatives have a lower estrogenic activity than ZEN but ZEN can be released again from these ZEN derivatives in the digestive tract under some circumstances.

Although ZEN has a relatively low acute toxicity and has an oral $LD_{50}$ of up to 20,000 mg/kg body weight, subacute and/or subchronic toxic effects such as teratogenic, carcinogenic, estrogenic and immunosuppressant effects may occur in animals or humans with prolonged exposure. Feed contaminated with ZEN leads to developmental disorders in mammalian animals, but pigs, in particular piglets, are extremely sensitive to ZEN. ZEN concentrations of more than 0.5 ppm in feed result in developmental disorders, and concentrations of more than 1.5 ppm in pigs, for example, can result in hyperestrogenicity, and concentrations of 12 ppm ZEN have been blamed for spontaneous abortions in cattle. Since zearalenone is absorbed rapidly through the mucous membranes, in particular through the gastric mucosa as well as the oral mucosa, immediate and quantitative deactivation is essential. ZEN can be detected in blood even 30 minutes after oral administration. In this case, the use of isolated enzymes offers some advantages with respect to microorganisms, such as a higher specific activity or a quicker effect. Because of the harmful effects of ZEN, the European Union has binding upper limits for ZEN in foodstuffs as well as recommendations for upper limits for ZEN in animal feed products (EC No. 1881/2006).

The primary strategy for reducing ZEN contamination of foods and animal feed products is to restrict the growth of fungi, for example, by maintaining "good agricultural practice." This includes, among other things, ensuring that the seed is free of pests and fungal infestation or that agricultural waste products are removed from the field promptly. In addition, fungal growth in the field can be reduced through the use of fungicides. After the harvest, the harvested material should be stored at a residual moisture level of less than 15% and at a low temperature to prevent the growth of fungi. Likewise, material contaminated by fungal infestation should be removed before further processing. Despite the list of measures, I. Rodriges and K. Naehrer (2012) have reported that, even in regions with the highest agricultural standards, such as the United States and Central Europe in the years 2009 to 2011, 29% and 39% respectively, of the tested corn samples were contaminated with ZEN.

Additional possibilities for removing ZEN from foodstuffs or animal feed products include adsorption and/or transformation of the mycotoxin. This requires that binding of the mycotoxin to the adsorbent must be strong and specific over a wide pH range and must remain stable in the gastrointestinal tract. Although some nonbiological adsorbents such as activated carbon and silicates or synthetic polymers such as cholestyramine can be used efficiently for aflatoxins, their use for other mycotoxins is limited. The main disadvantage of adsorbents is the nonspecific binding of other molecules, which are in some cases essential for nutrition. Biological adsorbents such as yeast or yeast extracts have also been described in the literature but have a limitation similar to that of nonbiological adsorbents.

Detoxification of ZEN by physical and chemical treatments is also limited. ZEN cannot be deactivated effectively by thermal treatment, but the ZEN content can be reduced by 83.9% by extrusion and treatment with oxidizing agents, for example, for 16 hours at 80° C. with 10% hydrogen peroxide solution. Use of extrusion methods and oxidizing agents such as ozone or hydrogen peroxide in the production of foodstuffs and animal feed products is limited because of the high cost, the loss of quality and in some cases the low efficacy and low specificity.

Biotransformation of ZEN by means of microorganisms such as *Trichosporon mycotoxinivorans*, *Gliocladium roseum* or *Bacillus subtilis* strains and/or enzymes isolated from them such as hydrolases or peroxidases his described, for example, by E. Vekiru et al. in Appl. and Environ. Microb., 2010, 76, 7, 2353-2359.

EP 0 938 575 B1 has described ZEN-degrading properties of bacteria of the genus *Rhodococcus* or *Nocardia*, in particular *R. globerulus*, *R. erythropolis* and *N. globerula*.

WO 02/076205 describes the ZEN-degrading effect of enzymes isolated from *Gliocladium roseum*, including α,β-hydrolase and zearalenone hydrolase 1 (ZHD1), which catalyze the degradation of ZEN by means of a catalytic triad.

WO 2012/113827 discloses recombinant zonases, namely enzymes that degrade ZEN and remain stable in the gastrointestinal tract. These include microorganisms such as *Thermobifidia fusca*, *Streptomyces exfoliates*, *Acidovorans delafieldii* and *Streptomyces* sp. in particular.

Polypeptides or enzymes capable of hydrolyzing ZEN and/or at least one ZEN derivative may also be designated as zonases.

The terms used hereinafter are taken from the technical language and each is used in the traditional meanings, unless something to the contrary is indicated. Thus, for example, the term "polynucleotide" relates to all types of genetic material of all lengths and sequences such as single-stranded and double-stranded DNA and RNA molecules, including regulatory elements, structural elements, groups of genes, plasmids, entire genomes and fragments thereof. The designation "polypeptide" includes proteins such as, for example, enzymes, antibodies as well as polypeptides with up to 500 amino acids, such as, for example, peptide inhibitors, domains of proteins or also short polypeptides with short sequence lengths, for example, less than 10 amino acids, such as receptors, ligands, peptide hormones, tags and the like. The designation "position" in a polynucleotide or polypeptide relates to a single specific base or amino acid in the sequence of the polynucleotide or of the polypeptide.

BRIEF SUMMARY OF THE INVENTION

The present invention is now aimed at making available a polypeptide with which it is possible to rapidly and reliably transform ZEN and/or at least one ZEN derivative into hydrolyzed ZEN and/or hydrolyzed ZEN derivatives.

To achieve this object, the present invention is characterized essentially in that the polypeptide is a hydrolase with an amino acid sequence of sequence ID number 1 or a functional variation thereof, wherein there is a sequence identity of at least 70% between the functional variant and the amino acid sequence.

The term "sequence identity" according to the present invention relates to a percentage sequence identity. For amino acid sequences and nucleotide sequences, the sequence identity can be determined visually, but is preferably calculated by a computer program. The sequence comparison is also carried out within sequence segments, wherein the segment is understood to be a continuous sequence of the reference sequence and preferably comprises a conserved region of the sequence.

In the present case, the sequence identity was determined with the help of the NCBI BLAST program (BLAST=Basic Logic Alignment Search Tool), in particular with BLASTP for polypeptides and BLASTN for polynucleotides, which are made available on the homepage of the National Center for Biotechnology Information. It is thus possible to compare two or more sequences with one another according to the algorithm of Altschul et al., 1997 (Nucleic Acids Res., 25:3389-3402). For this purpose of this invention, the programs were used in the version of 15 May 2013. The basic settings were used as the program settings, but in particular for the amino acid sequence comparison: "max target sequence"=100; "expected threshold"=10; "word size"=3; "matrix"=BLOSOM62; "gap costs"="existence: 11; extension: 1"; "computational adjustment"="conditional compositional score matrix adjustment" as well as for the nucleotide sequence comparison word size: 11; expect value: 10; gap costs: existence=5, extension=2; filter=low complexity activated; match/mismatch scores: 2-3; filter string: L; m.

The terms "functional polypeptide variant" or "functional variant" relate first to "allelic variants" of the polypeptide and to "functional fragments" of the polypeptide and secondly to "modification" of the polypeptide, wherein the enzymatic function is essentially unchanged. The term "allelic variant" relates to a polypeptide formed by naturally occurring mutation(s) in the nucleotide sequence and causing a change in the amino acid sequence, wherein the enzymatic function thereof is not affected. "Modifications" may be, for example, C- or N-terminal fusions with polypeptides or mutated polypeptides, wherein mutations can be obtained by substitution, insertion or deletion of at least one amino acid, in particular by site-directed mutagenesis, i.e., random mutagenesis, recombination and/or any other protein engineering method. The terms "substitution," "insertion" and "deletion" are used here in the common meanings in genetic engineering, with which those skilled in the art are familiar. The term "functional fragment" refers to a part or a subsequence of a polypeptide or a part and/or a subsequence of a functional variant thereof, wherein the enzymatic function is essentially retained. An enzymatic function is retained in particular when the enzymatic reaction mechanism remains unchanged, i.e., the mycotoxin is hydrolyzed in the same location, and the specific residual activity "functional variant" amounts to at least 5%, preferably at least 10%, especially at least 10%, and in particular at least 50%, based on the original polypeptide. The polypeptides with the amino acid sequences having the sequence ID numbers 1 through 15 are functional allelic variants either of one another or of one and the same enzyme, wherein the sequences originate from different microorganisms. This is clearly recognizable from the close relationship to one another, measured by means of the percentage sequence identity, as well as the fact that all polypeptides act on ZEN and ZEN derivatives by means of the same degradation mechanisms.

Because of the similarity in the amino acid sequences of the polypeptides with the sequence ID numbers 1 through 15 to one another, it is possible that a functional variant of one of these polypeptides may have a sequence identity of at least 40%, with more than one of the claimed polypeptides having the sequence ID numbers 1 through 15.

Through the choice of such an amino acid sequence or a functional variant thereof, a surprisingly fast and complete hydrolysis of ZEN and/or at least one ZEN derivative has been detected.

As corresponds to a preferred further development of the invention, the polypeptide has an amino acid sequence, which contains at least one conserved amino acid sequence segment or a functional variant thereof, wherein the functional variant of the amino acid sequence segment has a sequence identity of at least 70%, preferably at least 84%, more preferably at least 92% and most preferably at least 98%, and the at least one conserved amino acid sequence segment is selected from the group of amino acid sequences +24 to +50, +52 to +77, +79 to +87, +89 to +145, +150 to +171, +177 to +193, +223 to +228, +230 to +237, +239 to +247, +249 to +255, +257 to +261, +263 to +270, +272 to +279, +297 to +301, +303 to +313, +24 to 328, +1 to +328 of the sequence having the sequence ID no. 1. Due to the presence of at least one such conserved amino acid sequence segment, it has been possible to make available a polypeptide which also has, in addition to the rapid and complete hydrolysis of ZEN and/or of at least one ZEN derivative, a particularly high activity value in comparison with ZEN degrading polypeptides known previously.

Equally good results have been achieved when the functional variant has at least one amino acid modification selected from the group of substitution, deletion and insertion of one or more amino acids.

If the polypeptide has a specific activity of at least 0.01 U/mg, preferably at least 0.1 U/mg, in particular at least 1 U/mg; and/or a $K_M$ value of the hydrolytic cleavage of ZEN of at most 50 µM, preferably at most 3.5 µM, in particular at most 0.5 µM; and/or a $k_{cat}$ value of the hydrolytic cleavage of ZEN of at least 0.05 $s^{-1}$, preferably at least 0.6 $s^{-1}$, in particular at least 5 $s^{-1}$; and/or a $v_{max}$ value of the hydrolytic cleavage of ZEN of at least 0.00001 $µM^{-1}\ s^{-1}$, preferably at least 0.0001 $µM^{-1}\ s^{-1}$, in particular at least 0.001 $µM^{-1}\ s^{-1}$, then ZEN and/or ZEN derivatives can be hydrolyzed especially rapidly and completely, in particular being detoxified.

Hereby the polypeptide may contain an amino acid sequence selected from the group of sequence ID numbers 5, 6 and 15 or a functional variant thereof, wherein the functional variant has at least 70% sequence identity with at least one of the amino acid sequences, and the pH stability of the polypeptide at pH 5.0 amounts to at least 15%, preferably 50% and in particular preferably 90%. It is possible in this way to ensure that the polypeptide zearalenone and/or at least one zearalenone derivative will be cleaved and/or detoxified even in an acidic medium, such as the mammalian stomach, for example. The pH stability of polypeptides is defined here as the percentage residual activity of the polypeptides at pH 5.0 in relation to the activity at the respective optimum pH.

Corresponding to such further development, the polypeptide may contain an amino acid sequence selected from the group of sequence ID numbers 1, 5, 6 and 15 or a functional variant thereof, wherein the functional variant has at least 70% sequence identity with at least one of the amino acid sequences, and the polypeptide still has the highest enzymatic activity in a temperature range between 30° C. and 75° C., preferably between 38° C. and 55° C., in particular preferably between 38° C. and 52° C. Using such further development, it can be guaranteed that zearalenone and/or at least one zearalenone derivative is also hydrolyzed and/or detoxified by the polypeptide even at mesophilic temperatures, in particular at the body temperature of humans and farm animals. The temperature at which the polypeptide has the highest enzymatic activity is defined as the optimum temperature of the polypeptide.

Corresponding to a variant, the polypeptide may have an amino acid sequence selected from the group of sequence ID numbers 1, 5, 6 and 15 or a functional variant thereof, wherein the functional variant has at least 70% sequence identity with at least one of the amino acid sequences, and the polypeptide is thermally stable up to a temperature of 90° C., preferably 75° C. and in particular preferably 60° C. This way, the polypeptide and its enzymatic function will remain essentially intact even under elevated temperature stress, such as that which may occur, for example, during shipping in a container or during pelletization of feed. The thermal stability of polypeptides is defined as the temperature at which, after 15 minutes of preliminary incubation, the polypeptide has a 50% residual activity in comparison with the activity at the respective optimum temperature.

The polypeptide may be selected so that it has an α,β-hydrolase, which is suitable for oxygen-independent and cofactor-free hydrolytic cleavage of the ester group of zearalenone and/or of the ZEN derivatives, which has an amino acid triad that catalyzes the hydrolytic cleavage and consists of serine, an acidic amino acid selected from glutamic acid and aspartic acid, in particular aspartic acid and histidine, and the catalytic triad is, for example, S128, D264 and H303, wherein the positioning relative to the sequence ID no. 1 is shown.

Hydrolysis of ZEN and ZEN derivatives succeeds with any of the polypeptides of the sequence ID numbers 1 to 15 on the ester group of zearalenone or its derivatives according to the following reaction mechanism;

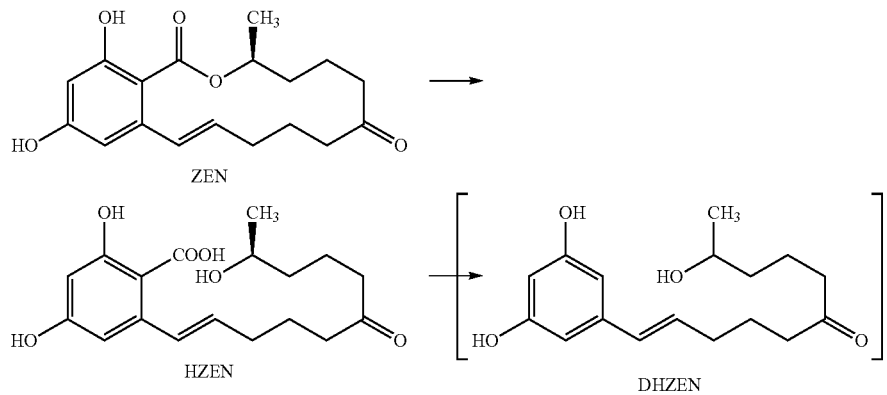

The hydrolysis of ZEN to form nontoxic hydrolyzed zearalenone (HZEN) and/or hydrolyzed ZEN derivatives takes place by means of polypeptides according to the invention, in particular α,β-hydrolases. The further decarboxylation of HZEN to decarboxylated hydrolyzed ZEN (DHZEN) and/or decarboxylated hydrolyzed ZEN derivatives is usually spontaneous.

In particular, by means of the aforementioned catalytic triads, it is possible to completely hydrolyze ZEN and ZEN derivatives, wherein the degradation reaction has a good pH stabilizing effect, in particular at a pH in the acidic range.

It has been found that it is possible to achieve uniformly good results with a polypeptide that contains in a sequence segment consisting of three amino acids before the serine and three amino acids after the serine of the aforementioned catalytic triad, at least one polar amino acid selected from Y, Q, N, T, K, R, E, D and at least one nonpolar amino acid selected from F, M, L, I, V, A, G, P, and it is also possible to improve at least one enzyme kinetic parameter.

In a preferred refinement of the invention, the polypeptide has at least one mutation of the amino acid sequence with respect to the sequence ID no. 1 in at least one of the following positions: 22, 23, 25, 26, 27, 29, 31, 32, 35, 37, 42, 43, 46, 51, 53, 54, 57, 60, 69, 72, 73, 78, 80, 84, 88, 95, 97, 99, 114, 118, 119, 123, 132, 141, 146, 148, 149, 154, 163, 164, 165, 169, 170, 172, 176, 180, 182, 183, 190, 191, 194, 196, 197, 198, 201, 204, 205, 206, 207, 208, 209, 210, 212, 213, 214, 216, 217, 220, 221, 222, 229, 231, 233, 238, 240, 244, 245, 246, 248, 249, 251, 254, 256, 260, 262, 263, 266, 269, 271, 277, 280, 281, 282, 283, 284, 285, 286, 287, 292, 296, 298, 302, 307, 308, 309, 311, 314, 317, 319, 321, 323, 325 and 326. These positions are derived from the sequence differences between the polypeptide with the sequence ID no. 1 and the polypeptides having the sequence ID numbers 2 to 6, which are especially active and have a high degree of identity with this sequence. If the polypeptide with sequence ID no. 1 is modified in at least one of these positions, so that the amino acid variants of sequence ID numbers 2 through 6 can be taken over in this position, it is possible to show that these positions have a significant influence on the enzyme kinetic parameters of the polypeptide and that combinations of the sequence ID no. 1 with sequence ID numbers 2 through 6 also having a high degree of sequence identity in addition will lead to higher activities.

According to one refinement of the invention, the polypeptide has at least one mutation selected from the group comprising: D22A, S23Q, S23L, N25D, I26V, F27Y, F27H, S29P, R31A, F32Y, R35K, R35Q, V37A, V42I, V43T, F46Y, S51E, S51D, D53G, N54M, N54R, L57V, L60I, S69G, P72E, V73A, A78S, N80H, F84Y, I88L, T95S, T97A, R99K, I114M, I118V, K119R, V123I, L132V, A141S, I146V, I146L, A148G, A149V, A154P, P163T, A164T, Y165C, Y165H, V169I, L170R, A172G, A176M, A176V, Y180F, D182T, F183Y, I190V, G191S, K194T, K194E, F196Y, V197C, V197R, E198R, E198S, K201D, K201G, P204S, P204A, A205S, K206P, A207M, M208A, Q209R, L210A, L210S, AP212, T213V, P214A, E216T, E216G, A217I, N220H, L221M, K222R, K222Q, G229A, A231V, F233W, F233Y, F233H, A238G, H240N, H240S, D244E, R245Q, M246L, S248T, S248N, S248G, Q249R, K251N, I254V, I256L, A260M, T262D, T262G, I263T, E266D, E269H, E269N, L271V, L277E, E280A, E280L, H281R, H281Q, A282V, Q283R, D284L, D284R, I285L, I286M, R287E, R287D, R292K, R292T, Q296A, Q296E, H298V, L302S, L307Q, F308S, D309A, A311P, A314V, L317F, S319Q, S319P, S319R, S321A, S321T, T323A, P325A, A326P in the amino acid sequence with respect to sequence ID no. 1. With such a polypeptide, it is possible to completely hydrolyze ZEN within a short period of time, in particular to detoxify it, wherein the specific activity of the polypeptide amounts to at least 6.00 U/mg, preferably at least 7.00 U/mg, in particular at least 8.00 U/mg. The unit "U" or also "unit" is a measure of the absolute catalytic activity and is defined by the hydrolysis of 1 μmol ZEN per minute at 32° C. in 50 mM Tris-HCl buffer (pH 8.2), wherein "catalytic activity" is understood to refer to the enzymatic conversion of a substrate under defined reaction conditions, and "specific activity" is understood to refer to the ratio of the catalytic activity and the polypeptide mass concentration (mass per unit of volume).

If, according to one refinement of the invention, the polypeptide is embodied so that at least one of the following amino acid motifs with a sequence having sequence ID numbers 32 to 50 is contained in it, it is then possible to make available polypeptides having a specific activity of at least 17.00 U/mg, preferably at least 8.00 U/mg. It has surprisingly been found that when at least one of the following amino acid motifs with a sequence having the sequence ID numbers 51 to 58 is contained in it, the enzymatic activity of the polypeptide is increased further, for example, in comparison with a motif containing seven amino acids. An even higher specific activity is achieved when at least one of the following amino acid motifs having the sequence having the sequence ID numbers 59 to 69 is contained in it.

Furthermore, the polypeptide may contain at least one conservative amino acid substitution in at least one position, where the conservative amino acid substitution is selected from substitutions of G to A; or A to G, S; or V to I, L, A, T, S; or I to V, L, M; or L to I, M, V; or M to L, I, V; or P to A, S, N; or F to Y, W, H; or Y to F, W, H; or W to Y, F, H; or R to K, E, D; or K to R, E, D; or H to Q, N, S; or D to N, E, K, R, Q; or E to Q, D, K, R, N; or S to T, A; or T to S, V, A; or C to S, T, A; or N to D, Q, H, S; or Q to E, N, H, K, R, wherein the designation "conservative amino acid substitution" relates to the substitution of amino acids by other amino acids regarded by those skilled in the art as being conservative, i.e., having similar specific properties. Such specific properties include, for example, the size, polarity, hydrophobicity, charge or pKs value of the amino acid. A conservative mutation, for example, is understood to be a substitution of one acidic amino acid for another acidic amino acid, a basic amino acid for another basic amino acid or a polar amino acid for another polar amino acid.

With such conservative amino acid substitutions, it is possible to produce functional polypeptide variants whose specific activity is approximately the same in comparison with the parental polypeptide but is preferably increased by at least 0.1 U/mg.

Furthermore, an isolated polynucleotide is made available with which it is possible to produce a polypeptide for the rapid and reliable hydrolytic cleavage of ZEN and/or at least one ZEN-derivative.

Therefore, the isolated polynucleotin may have a nucleotide sequence that codes for a polypeptide, wherein the polypeptide has a zearalenone and/or the property of hydrolyzing at least one zearalenone derivative, and the nucleotide sequence codes for at least one polypeptide according to the invention and/or the nucleotide sequence has a degree of sequence identity of at least 70% with a nucleotide sequence selected from the group of sequence ID numbers 16 to 31 and/or the nucleotide sequence hydrolyzes under moderate stringency conditions with at least one nucleotide sequence selected from the group of sequence ID numbers 16 to 31 and/or with a subsequence thereof with at least 200 nucleotides, in particular at least 100 nucleotides and/or with a complementary strand of the nucleotide sequence or subsequences thereof.

Nucleotide sequences to be expressed, in particular their triplets (codons) are usually altered depending on the host cell so that the codon bias is optimized according to the host cell. This results in the fact that even polynucleotides having a degree of sequence identity of far less than 80% but even less than 70% or less than 60% can code for the same polypeptide. The sequence comparison for determining the degree of sequence identity must also be performed within sequence segments, wherein one section is to be understood as a continuous sequence of the reference sequence. The length of the sequence segments for nucleotide sequences is normally 15 to 600.

With the help of the present isolated nucleotide sequences or sequence segments, it is possible to generate nucleic acid probes having a length of usually at least 15, 30 or 40 nucleotides. With such probes, which are typically also labeled, e.g., by $^3$H, $^{32}$P, $^{35}$S, biotin or avidine, it is possible, by using standard methods, to identify nucleotide sequences that code for polypeptides with the property of degrading ZEN and/or ZEN derivatives. For example, DNA, RNA or cDNA from individual microorganisms, genomic DNA libraries or cDNA libraries can be used as the starting material for identification of such sequences.

For nucleotide sequences and/or nucleotide probes with a length of at least 100 nucleotides, moderate stringency conditions are defined as prehybridization and hybridization at 42° C. in Na-EDTA buffer provided with 5× NaCl (SPE, 0.9M NaCl, 60 mM NaH$_2$PO$_4$, 6 mM EDTA) containing 0.3% sodium dodecyl sulfate (SDS), 200 μg/mL sheared and denatured salmon sperm DNA and 35% formamide followed by standard Southern Blot conditions, wherein the carrier material is washed three times at the end for 15 minutes each with 2× sodium chloride citrate buffer (SSC, 300 mM NaCl and 30 mM trisodium citrate, 0.2% SDS) at 55° C.

For nucleotide sequences and/or nucleotide probes with a length of 15 nucleotides to 100 nucleotides, moderate stringency conditions are defined as prehybridization and hybridization in buffer consisting of 0.9M NaCl, 0.09M Tris-HCl pH=7.6, 6 mM EDTA, 0.5% NP-40, 1×Denhardt's solution, 1 mM sodium pyrophosphate, 1 mM sodium dihydrogen phosphate, 0.1 mM ATP and 0.2 mg/mL yeast RNA, wherein prehybridization and hybridization are performed at a temperature 5° C. to 10° C. below the calculated melting point (Tm), where Tm is determined by calculation according to Bolton and McCarthy (1962, Proceedings of the National Academy of Sciences USA, 48:1390). Following this, the experiment is continued under standard Southern Blot conditions (J. Sambrook, E. F. Fritsch and T. Maniatis, 1989, Molecular Cloning, A Laboratory Manual, 2$^{nd}$ edition, Cold Spring Harbor, N.Y.). The carrier material is washed at the end once for 15 minutes with 6×SCC buffer [sic; SSC buffer] containing 0.1% SDS and twice for 15 minutes with 6×SSC buffer each at 5° C. to 10° C. under the calculated Tm.

The present invention is additionally aimed at making available an additive with which it is possible to achieve a rapid and reliable hydrolytic cleavage of ZEN and/or at least one ZEN derivative in a defined or complex matrix, such as, for example, in food or animal feed products.

To achieve this goal, an additive that hydrolytically cleaves a zearalenone and/or at least zearalenone derivative is made available for animal feed products for pigs, poultry or aquaculture, for foodstuffs or DDGS (distillers dried grain and solubles), wherein the additive contains at least one polypeptide having an amino acid sequence of sequence ID number 1 or a functional variant thereof, wherein the sequence identity between the functional variant and the amino acid sequences amounts to at least 70%, and auxiliary substances are also present.

With such an additive, the biochemical conversion of ZEN and/or at least one ZEN derivative to hydrolyzed ZEN and/or hydrolyzed ZEN derivative is possible. This additive can also be used, for example, for stereoselective hydrolysis of ZEN and/or ZEN derivatives in industrial processes.

In a preferred refinement of the invention, the additive is embodied so that the auxiliary substances are selected from at least one inert carrier as well as optionally additional ingredients, such as vitamins and/or minerals and/or enzymes and/or additional components for detoxification of mycotoxins. Due to the use of such an additive, for example, in foodstuffs or animal feed products, it is possible to ensure that any amounts of ZEN and/or ZEN derivatives that might be present are reliably hydrolyzed, in particular being detoxified to the extent that they will have no harmful effect on the organism of the subject consuming this foodstuff or animal feed product.

A polypeptide according to the invention here may also be present in an enzyme preparation, which additionally contains at least one enzyme in addition to at least one polypeptide according to the invention, such that the enzyme takes part in the degradation of proteins, for example, such as proteases, or plays a role in the metabolism of starch or fiber or fat or glycogen, such as, for example, amylase, cellulase or glucanases as well as, for example, hydrolases, lipolytic enzymes, mannosidase, oxidases, oxidoreductases, phytases, xylanases and/or combinations thereof.

Additional fields of use of the invention include enzyme preparations, which, in addition to at least one polypeptide according to the invention, also contain at least one component for detoxification of mycotoxins, such as a mycotoxin-degrading enzyme, for example, aflatoxin oxidase, ergotamine hydrolases, ergotamine amidases, zearalenone esterases, zearalenone lactonases, ochratoxin amidases, fumonisin carboxyl esterases, fumonisin aminotransferases, aminopolyol aminooxidases, deoxynivalenol epoxide hydrolases and/or at least one mycotoxin-degrading microorganism, such as *Bacillus subtilis* and/or at least one mycotoxin-binding component, for example, microbial cell walls or inorganic materials such as bentonites.

According to one particularly preferred refinement of the invention, the polypeptide is present in the additive in a concentration of at most 10,000 U/g, preferably at most 1000 U/g, more preferably at most 100 U/g and most preferably at most 10 U/g, so that it is possible to convert ZEN and/or ZEN derivatives rapidly and in particular to do so already before they are absorbed by the body of a subject, in particular a mammal consuming a contaminated foodstuff or animal feed product, converting them into nontoxic or less toxic metabolites, in particular HZEN and DHZEN.

According to a refinement of the invention, the polypeptide is present in encapsulated or coated form, wherein standard methods such as those described in WO 92/12645 can be used for the encapsulation or coating. By encapsulation and/or coating, it is possible to transport the polypeptide without any change, in particular without degradation or damage, to its site of use, so that only after the protective shell has been dissolved in the digestive tract of animals, for example, does the polypeptide begin to act so that an even more targeted, rapid and complete degradation of ZEN and/or ZEN derivatives can be achieved even in the acidic protease-rich and anaerobic medium. In addition, it is also possible through encapsulation or coating to increase the thermal stability of the polypeptides in the additive.

The present invention is additionally aimed at use of an additive containing one polypeptide having an amino acid sequence of sequence ID number 1 or a functional variant thereof, wherein the sequence identity between the functional variant and the amino acid sequence amounts to at least 70% for hydrolytic cleavage of zearalenone and/or at least one zearalenone derivative in animal feed products, in particular for pigs, poultry and agriculture, in foodstuffs or in distillers dried grain and solubles. Through the use of the additive according to the invention, it is possible to hydrolyze and/or detoxify the ZEN and/or ZEN derivatives contained in the foodstuff or animal feed product and/or distillers dried grain and solubles, wherein such a detoxification is possible even with polypeptide concentrations of approximately 1 U/g contaminated foodstuff or animal feed product.

The present invention is additionally aimed at making available a method with which a rapid and reliable hydrolytic cleavage of ZEN and/or at least one ZEN derivative is made possible.

To achieve this goal, this method is carried out in such a way that zearalenone and/or at least one zearalenone derivative having an amino acid sequence of sequence ID number 1 or a functional variant thereof is hydrolyzed, wherein the sequence identity between the functional variant and the amino acid sequences amounts to at least 70%.

According to one refinement of the invention the method is carried out in such a way that the polypeptide therein is used in an additive corresponding to this invention.

According to another preferred refinement, the method is carried out in such a way that the polypeptide or the additive therein is mixed with a foodstuff or animal feed product contaminated with zearalenone and/or with at least one zearalenone derivative; the contaminated foodstuff or animal feed product is brought in contact with moisture and the polypeptide or the additive hydrolyzes the zearalenone and/ or at least one zearalenone derivative contained in the contaminated foodstuff or animal feed product. In the case of moist foodstuffs or animal feed products, such as mash or slurries, the hydrolysis of the zearalenone and/or of at least one zearalenone derivative will take place in the moist foodstuff or animal feed product before oral consumption. Due to this method, it is possible to ensure that the harmful effects of zearalenone and zearalenone derivatives on humans and animals will be largely eliminated. Moisture here is understood to refer to the presence of water or aqueous liquids, which also include, for example, saliva or other liquids present in the digestive tract. The digestive tract is defined as the oral cavity, the pharynx (throat), the esophagus and the gastrointestinal tract or equivalents thereof, wherein there may be different designations for animals and/or individual components may not occur in the digestive tract of animals.

The method according to the invention may also be carried out in such a way that the foodstuff or animal feed product is pelletized before oral consumption.

According to one refinement of the invention, the method is carried out so that at least 70%, preferably at least 80% in particular at least 90% of the zearalenone and/or at least one zearalenone derivative is hydrolyzed. Therefore, subacute and/or chronic toxic effects such as teratogenic, carcinogenic, estrogenic and immunosuppressant effects in animals or humans, for example, can be suppressed.

BRIEF DESCRIPTION OF THE SEVERAL VIEWS OF THE DRAWINGS

The invention is explained in greater detail below on the basis of exemplary embodiments as well as drawings, in which:

FIG. 1 consists of FIGS. 1A-1C.

FIG. 1A depicts the degradation of ZEN and the increase in the metabolites HZEN and DHZEN over time when incubating with the polypeptide having the sequence ID no. 1, whereas at the y-axes the ZEN, HZEN and DHZEN concentrations in ppm and at the x-axes the reaction time in hours are plotted.

FIG. 1B depicts the degradation of ZEN and the increase in the metabolites HZEN and DHZEN over time when incubating with the polypeptide having the sequence ID no. 1 having an additional C-terminal 6×His tag, whereas at the y-axes the ZEN, HZEN and DHZEN concentrations in ppm and at the x-axes the reaction time in hours are plotted.

FIG. 1C depicts the degradation of ZEN and the increase in the metabolites HZEN and DHZEN over time when incubating with the polypeptide having the sequence ID no. 1 having an additional N-terminal 6×His tag, whereas at the y-axes the ZEN, HZEN and DHZEN concentrations in ppm and at the x-axes the reaction time in hours are plotted.

FIG. 2 consists of FIGS. 2A-2B.

FIG. 2A depicts the Michaelis-Menten kinetics of the polypeptide with sequence ID no. 1, whereas at the y-axes the enzymatic reaction rates in μmol/s and at the x-axes the substrate concentrations in μM are plotted.

FIG. 2 B depicts as a biological replicate to FIG. 1 A as well the Michaelis-Menten kinetics of the polypeptide with sequence ID no. 1, whereas at the y-axes the enzymatic reaction rates in μmol/s and at the x-axes the substrate concentrations in μM are plotted.

FIG. 3 consists of FIGS. 3A-3I.

FIG. 3 A depicts the degradation of ZEN and the increase in metabolites HZEN and DHZEN over time when incubating with the purified polypeptide having the sequence ID numbers 1 having an additional C-terminal 6×His tag, whereas at the y-axes the ZEN, HZEN and DHZEN concentrations in μM and at the x-axes the reaction time in hours are plotted.

FIG. 3 B depicts the degradation of ZEN and the increase in metabolites HZEN and DHZEN over time when incubating with the purified polypeptide having the sequence ID numbers 2 having an additional C-terminal 6×His tag, whereas at the y-axes the ZEN, HZEN and DHZEN concentrations in μM and at the x-axes the reaction time in hours are plotted.

FIG. 3 C depicts the degradation of ZEN and the increase in metabolites HZEN and DHZEN over time when incubating with the purified polypeptide having the sequence ID numbers 5 having an additional C-terminal 6×His tag, whereas at the y-axes the ZEN, HZEN and DHZEN concentrations in μM and at the x-axes the reaction time in hours are plotted.

FIG. 3 D depicts the degradation of ZEN and the increase in metabolites HZEN and DHZEN over time when incubating with the purified polypeptide having the sequence ID numbers 6 having an additional C-terminal 6×His tag, whereas at the y-axes the ZEN, HZEN and DHZEN concentrations in μM and at the x-axes the reaction time in hours are plotted.

FIG. 3 E depicts the degradation of ZEN and the increase in metabolites HZEN and DHZEN over time when incubating with the purified polypeptide having the sequence ID numbers 7 having an additional C-terminal 6×His tag, whereas at the y-axes the ZEN, HZEN and DHZEN concentrations in μM and at the x-axes the reaction time in hours are plotted.

FIG. 3 F depicts the degradation of ZEN and the increase in metabolites HZEN and DHZEN over time when incubating with the purified polypeptide having the sequence ID numbers 9 having an additional C-terminal 6×His tag, whereas at the y-axes the ZEN, HZEN and DHZEN concentrations in μM and at the x-axes the reaction time in hours are plotted.

FIG. 3 G depicts the degradation of ZEN and the increase in metabolites HZEN and DHZEN over time when incubating with the purified polypeptide having the sequence ID numbers 11 having an additional C-terminal 6×His tag, whereas at the y-axes the ZEN, HZEN and DHZEN concentrations in μM and at the x-axes the reaction time in hours are plotted.

FIG. 3 H depicts the degradation of ZEN and the increase in metabolites HZEN and DHZEN over time when incubating with the purified polypeptide having the sequence ID numbers 12 having an additional C-terminal 6×His tag, whereas at the y-axes the ZEN, HZEN and DHZEN concentrations in μM and at the x-axes the reaction time in hours are plotted.

FIG. 3 I depicts the degradation of ZEN and the increase in metabolites HZEN and DHZEN over time when incubating with the purified polypeptide having the sequence ID numbers 15 having an additional C-terminal 6×His tag, whereas at the y-axes the ZEN, HZEN and DHZEN concentrations in μM and at the x-axes the reaction time in hours are plotted.

DETAILED DESCRIPTION OF THE INVENTION

Example 1: Modification, Cloning and Expression of Polynucleotides that Code for Polypeptides Which are Capable of Hydrolytic Cleavage of ZEN and/or at Least One ZEN Derivative Amino acid substitutions, insertions or deletions were performed by mutation of the nucleotide sequences by means of PCR using the "quick change site-directed mutagenesis kits" (Stratagene) according to the instructions. As an alternative, complete nucleotide sequences were also ordered (GeneArt). The nucleotide sequences generated by means of PCR mutagenesis and/or ordered from GeneArt optionally also contained a C- or N-terminal 6×His tag on an amino acid level and were integrated by means of standard methods into expression vectors for expression in *E. coli* or *P. pastoris*, transformed in *E. coli* or *P. pastoris* and expressed in *E. coli* and *P. pastoris* (J. M. Cregg, *Pichia Protocols*, second edition, ISBN-10: 1588294293, 2007; J. Sambrook et al., 2012, Molecular Cloning, A Laboratory Manual, 4$^{th}$ edition, Cold Spring Harbor), wherein any other suitable host cell may also be used for this task.

The designation "expression vector" relates to a DNA construct that is capable of expressing a gene in vive or in vitro. In particular this is understood to refer to DNA constructs that are suitable for transferring the polypeptide coding nucleotide sequence into the host cell to integrate into the genome there or to be present freely in the extra-chromosomal space and to express the polypeptide coding nucleotide sequence intracellularly and optionally also to remove the polypeptide from the cell.

The designation "host cell" refers to all cells containing either a nucleotide sequence to be expressed or an expression vector and being capable of synthesizing a polypeptide according to the Invention. In particular this is understood to include prokaryotic and/or eukaryotic cells, preferably *P. pastoris*, *E. coli*, *Bacillus subtilis*, *Streptomyces*, *Hansenula*, *Trichoderma*, *Lactobacillus*, *Aspergillus*, plant cells and/or spores of *Bacillus*, *Trichoderma* or *Aspergillus*.

The soluble cell lysate in the case of *E. coli* and/or the culture supernatant in the case of *P. pastoris* was/were used for determination of the catalytic properties of the polypeptides. To determine the $K_M$ value, $v_{max}$, $k_{cat}$ and the specific activity, the polypeptides were selectively enriched chromatographically by standard methods over nickel-Sepharose columns. The determination of the protein concentration was performed by means of standard methods, either being calculated by the BCA method (Pierce BCA Protein Assay KitProd #23225) or preferably photometrically with the specific extinction coefficients for the respective proteins that are available online with the ProtParam program at (Gasteiger E. et al.; *Protein Identification and Analysis Tools on the ExPASy Server*, in John M. Walker (ed): The Proteomics Protocols Handbook, Humana Press, 2005, pp. 571-607).

Example 2: Determination of the Sequence Identity and the Conserved Amino Acid Sequence Segments The determination of the percentage sequence identity based on the total polypeptide length of the polypeptides with eh amino acid sequences having the sequence ID numbers 1 to 15 relative to one another (Table 1) was performed with the help of the BLAST program (Basic Local Alignment Search Tool), in particular with BLASTP, which can be used at homepage of the National Center for Biotechnology Information (NCBI). It is thus possible to compare two or more sequences with one another according to the algorithm of Altschul et al., 1997 (Nucleic Acids Res. (1997), 25:3389-3402). The basic settings were used as the program settings in particular. However. "max target sequence"=100; expected threshold"=10; "word size"=3; "matrix"=BLOSOM62; "gap costs"="existence: 11; extension: 1"; "computational adjustment"="conditional compositional score matrix adjustment."

To determine the conserved amino acid sequence segments, the polypeptides having sequence ID numbers 1 to 6, which have a sequence identity of at least 70% with one another, were compared with the help of the COBALT software (J. S. Papadopoulos and R. Agarwala, 2007, COBALT: Constraint-Based Alignment Tool for Multiple Protein Sequences, Bioinformatics 23:1073-79) while using the standard parameters, in particular the parameters ("gap penalties": −11, −1; "end-gap penalties": −5, −1; "use RPS BLAST": on; "Blast E-value": 0.003; "find conserved columns and recompute": on; "use query clusters": on; "word size": 4; "may cluster distance": 0,8; "alphabet": regular; "homology conversation setting": 3 bits). The result of this analysis represents the conserved amino acids. The following ranges of at least five successive conserved amino acids were defined as the conserved amino acid sequence segments, namely with respect to the segment having the sequence ID no. 1, the segments A from position +24 to position +50, B from position +52 to position +77, C from position +79 to position +87, D from position +89 to position +145, E from position +150 to position +171, F from position +177 to position +193, G from position +223 to position +228, H from position +230 to position +237, I from position +239 to position +247, J from position +249 to position +255, K from position +257 to position +261, L from position +263 to position +270, M from position +272 to position +279, N from position +297 to position +301 and O from position +303 to position +313.

The determinations of the percentage sequence identity of the polypeptides to one another and of the conserved amino acid sequence segments of the individual polypeptides relative to the conserved amino acid sequence segments of the sequence having the sequence ID no. 1 were formed as described above. The results are presented in Tables 1 and 2.

TABLE 1

Percentage sequence identity of the polypeptides to one another.

|  | SEQ ID No. 1 | SEQ ID No. 2 | SEQ ID No. 3 | SEQ ID No. 4 | SEQ ID No. 5 | SEQ ID No. 6 | SEQ ID No. 7 |
|---|---|---|---|---|---|---|---|
| SEQ ID No. 1 | — | 70% | 71% | 71% | 71% | 71% | 64% |
| SEQ ID No. 2 | 70% | — | 81% | 83% | 81% | 83% | 63% |
| SEQ ID No. 3 | 71% | 81% | — | 95% | 99% | 92% | 60% |
| SEQ ID No. 4 | 71% | 83% | 95% |  | 95% | 95% | 60% |
| SEQ ID No. 5 | 71% | 81% | 99% | 95% | — | 93% | 60% |
| SEQ ID No. 6 | 71% | 83% | 92% | 95% | 93% | — | 61% |
| SEQ ID No. 7 | 64% | 63% | 60% | 60% | 60% | 61% | — |
| SEQ ID No. 8 | 57% | 54% | 54% | 53% | 53% | 53% | 53% |
| SEQ ID No. 9 | 50% | 50% | 53% | 53% | 53% | 55% | 51% |
| SEQ ID No. 10 | 55% | 52% | 55% | 54% | 55% | 53% | 52% |
| SEQ ID No. 11 | 53% | 51% | 53% | 51% | 51% | 52% | 54% |
| SEQ ID No. 12 | 50% | 49% | 50% | 50% | 50% | 49% | 51% |
| SEQ ID No. 13 | 55% | 49% | 51% | 51% | 51% | 52% | 54% |
| SEQ ID No. 14 | 73% | 65% | 69% | 70% | 69% | 68% | 80% |
| SEQ ID No. 15 | 79% | 68% | 71% | 71% | 71% | 72% | 63% |

|  | SEQ ID No. 8 | SEQ ID No. 9 | SEQ ID No. 10 | SEQ ID No. 11 | SEQ ID No. 12 | SEQ ID No. 13 | SEQ ID No. 14 | SEQ ID No. 15 |
|---|---|---|---|---|---|---|---|---|
| SEQ ID No. 1 | 57% | 50% | 55% | 53% | 50% | 55% | 73% | 79% |
| SEQ ID No. 2 | 54% | 50% | 52% | 51% | 49% | 49% | 65% | 68% |
| SEQ ID No. 3 | 54% | 53% | 55% | 53% | 50% | 51% | 69% | 71% |
| SEQ ID No. 4 | 53% | 53% | 54% | 51% | 50% | 51% | 70% | 71% |
| SEQ ID No. 5 | 53% | 53% | 55% | 51% | 50% | 51% | 69% | 71% |

TABLE 1-continued

Percentage sequence identity of the polypeptides to one another.

| | | | | | | | | |
|---|---|---|---|---|---|---|---|---|
| SEQ ID No. 6 | 53% | 55% | 53% | 52% | 49% | 52% | 68% | 72% |
| SEQ ID No. 7 | 53% | 51% | 52% | 54% | 51% | 54% | 80% | 63% |
| SEQ ID No. 8 | — | 50% | 49% | 51% | 49% | 48% | 83% | 51% |
| SEQ ID No. 9 | 50% | — | 51% | 52% | 69% | 51% | 67% | 51% |
| SEQ ID No. 10 | 49% | 51% | — | 76% | 52% | 52% | 63% | 56% |
| SEQ ID No. 11 | 41% | 50% | 76% | — | 52% | 51% | 58% | 52% |
| SEQ ID No. 12 | 49% | 52% | 52% | 52% | — | 49% | 71% | 51% |
| SEQ ID No. 13 | 48% | 51% | 52% | 51% | 49% | — | 54% | 53% |
| SEQ ID No. 14 | 83% | 67% | 63% | 58% | 71% | 55% | — | 72% |
| SEQ ID No. 15 | 51% | 51% | 56% | 52% | 51% | 53% | 72% | — |

TABLE 2

Percentage sequence identity of the conserved amino acid sequence segments A to O.

| Polypeptide | Sequence identity relative to the sequence ID no. 1 | | | | | |
|---|---|---|---|---|---|---|
| | Segment A | Segment B | Segment C | Segment D | Segment E | Segment F |
| SEQ ID No. 1 | 100% | 100% | 100% | 100% | 100% | 100% |
| SEQ ID No. 2 | 59.6% | 76.9% | 88.9% | 87.7% | 77.3% | 76.5% |
| SEQ ID No. 3 | 63.0% | 76.9% | 77.8% | 89.5% | 86.4% | 76.5% |
| SEQ ID No. 4 | 63.0% | 80.8% | 77.8% | 91.2% | 86.4% | 76.5% |
| SEQ ID No. 5 | 63.0% | 76.9% | 77.8% | 87.7% | 86.4% | 76.5% |
| SEQ ID No. 6 | 63.0% | 80.8% | 77.8% | 91.2% | 86.4% | 76.5% |
| SEQ ID No. 7 | 44.7% | 69.2% | 77.8% | 78.9% | 68.2% | 64.7% |
| SEQ ID No. 8 | 40.7% | 50.0% | 66.7% | 82.5% | 59.1% | 64.7% |
| SEQ ID No. 9 | 51.9% | 57.7% | 55.6% | 73.7% | 45.5% | 58.8% |
| SEQ ID No. 10 | 44.4% | 61.5% | 77.8% | 75.4% | 47.8% | 76.5% |
| SEQ ID No. 11 | 44.4% | 50.0% | 66.7% | 71.9% | 43.5% | 58.8% |
| SEQ ID No. 12 | 51.9% | 53.8% | 55.6% | 71.9% | 50.0% | 58.8% |
| SEQ ID No. 13 | 18.5% | 61.5% | 55.6% | 77.2% | 54.5% | 52.9% |
| SEQ ID No. 14 | 55.6% | 69.2% | 77.8% | 84.2% | 54.5% | 52.9% |
| SEQ ID No. 15 | 74.1% | 86.7% | 88.9% | 89.0% | 77.3% | 88.2% |

| | Segment G | Segment H | Segment I | Segment J | Segment K | Segment L |
|---|---|---|---|---|---|---|
| SEQ ID No. 1 | 100% | 100% | 100% | 100% | 100% | 100% |
| SEQ ID No. 2 | 100% | 87.5% | 66.7% | 85.7% | 80.0% | 75.0% |
| SEQ ID No. 3 | 100% | 87.5% | 77.8% | 57.1% | 80.0% | 75.0% |
| SEQ ID No. 4 | 100% | 87.5% | 77.8% | 57.1% | 80.0% | 75.0% |
| SEQ ID No. 5 | 100% | 87.5% | 77.8% | 57.1% | 80.0% | 75.0% |
| SEQ ID No. 6 | 100% | 75.0% | 77.8% | 85.7% | 80.0% | 87.5% |
| SEQ ID No. 7 | 100% | 87.5% | 66.7% | 71.4% | 100% | 50.0% |
| SEQ ID No. 8 | 100% | 62.5% | 44.4% | 57.1% | 80.0% | 62.5% |
| SEQ ID No. 9 | 100% | 12.5% | 44.4% | 42.9% | 60.0% | 62.5% |
| SEQ ID No. 10 | 100% | 62.5% | 55.6% | 71.4% | 80.0% | 50.0% |
| SEQ ID No. 11 | 100% | 50.0% | 55.6% | 57.1% | 80.0% | 50.0% |
| SEQ ID No. 12 | 100% | 12.5% | 22.2% | 57.1% | 80.0% | 52.5% |
| SEQ ID No. 13 | 100% | 50.0% | 44.4% | 57.1% | 80.0% | 75.0% |
| SEQ ID No. 14 | 0% | 8.3% | 0% | 14.3% | 0% | 25.0% |
| SEQ ID No. 15 | 100% | 87.5% | 100% | 85.7% | 100% | 75.0% |

| | Segment M | Segment N | Segment O |
|---|---|---|---|
| SEQ ID No. 1 | 100% | 100% | 100% |
| SEQ ID No. 2 | 87.5% | 80.0% | 81.8% |
| SEQ ID No. 3 | 87.0% | 80.0% | 81.8% |
| SEQ ID No. 4 | 87.5% | 80.0% | 81.8% |
| SEQ ID No. 5 | 87.5% | 80.0% | 81.8% |
| SEQ ID No. 6 | 87.5% | 80.0% | 72.7% |
| SEQ ID No. 7 | 75.0% | 40.0% | 36.4% |
| SEQ ID No. 8 | 75.0% | 60.0% | 54.5% |
| SEQ ID No. 9 | 62.5% | 40.0% | 54.5% |
| SEQ ID No. 10 | 62.5% | 40.0% | 54.5% |
| SEQ ID No. 11 | 75.0% | 40.0% | 54.5% |
| SEQ ID No. 12 | 100% | 40.0% | 54.5% |
| SEQ ID No. 13 | 50.0% | 40.0% | 63.6% |
| SEQ ID No. 14 | 6.2% | 0% | 0% |
| SEQ ID No. 15 | 87.5% | 80.0% | 63.6% |

Example 3: Hydrolysis of ZEN by Polypeptides in Cell Lysates

To determine their ability to degrade ZEN into the non-toxic or less toxic metabolites HZEN and DHZEN, the polypeptide with the sequence ID no. 1, coded by the nucleotide sequence having the sequence ID no. 17 was synthesized as such and with a C-terminal and/or N-terminal 6×His tag in *E. coli* as described in example 1. The polypeptides with the amino acid sequences having the sequence ID numbers 2 to 15 which were coded by the nucleotide sequences having the sequence ID numbers 18 to 31, were labeled with 6×His exclusively at the C-terminus. 100 mL portions of an *E. coli* culture having an optical density (OD 600 nm) of 2.0-2.5 were harvested by centrifugation at 4° C. and resuspended in 20 mL Brunner mineral medium (DSMZ microorganisms medium number 462, 2012). The cell suspensions were lysed by treating three times with a French press at 20,000 psi. The resulting cell lysates were used in a 1:10, 1:100 or 1:1000 dilution prepared in Brunner mineral medium including 0.1 mg/mL BSA (bovine serum albumin). For the ZEN degradation experiments, 9.9 mL Brunner mineral medium was used, including 0.1 mg/mL BSA, 0.1 mL dilute cell lysate and 31 μL ZEN substrate stock solution. On the whole, the cell lysates were thus diluted 1:1000, 1:10,000 and/or 1:100,000. The ZEN substrate stock solution used was a 2.08 mM ZEN solution (40 vol % CAN+60 vol % $H_2O$). To prepare this solution, ZEN in crystalline form (Biopure Standard from Romer Labs, article no. 001109, purity at least 98%) was weighed and dissolved accordingly. Each degradation batch was carried out in 25 mL glass vials and incubated at 25° C. and 100 rpm for a total of 120 hours with agitation. At the times 0, 0.5, 1, 2, 5, 24, 47, 72 and 120 h, a sample of 1 mL was taken each time, the polypeptides were heat inactivated for 10 minutes at 99° C. and stored at −20° C. After thawing the sample, the insoluble constituents were separated by centrifugation. ZEN, HZEN and DHZEN were analyzed by means of LC/MS/MS. To do so, the metabolites were separated chromatographically on a Phenomenex Luna C18(2) column having the dimensions 250 mm×3 mm and a particle size of 5 μm, using as the mobile phase an acetonitrile-water mixture with a formic acid concentration of 1 mL/L. The UV signal at 270 nm was recorded using electrospray ionization (ESI) as the ionizing source. ZEN, HZEN and DHZEN were quantified by means of QTrap/LC/MS/MS (triple quadrupole, Applied Biosystems) in the enhanced mode. After 24 hours at the latest, substantial amounts of ZEN could not be detected any more in any of the batches. Most of the ZEN, i.e., more than 80%, was converted into HZEN or DHZEN. FIG. 1 shows the degradation of ZEN over time and the increase in HZEN as well as DHZEN for a 1:10,000 diluted cell lysate solution as an example for untagged (FIG. 1A) as well as for C-terminal 6×His tagged (FIG. 1B) and N-terminal 6×His tagged (FIG. 1C) polypeptide with the sequence ID no. 1. It can be seen here clearly that 1) the reaction of ZEN takes place directly and completely because almost no ZEN could be detected any longer in the first sample (0 h), which was taken immediately after the start of the experiment, and 2) no mentionable losses of activity occurred as a result of attaching a tag, whether C-terminal or N-terminal.

Example 4: Hydrolysis of ZEN Derivatives by Polypeptides in Cell Lysates

To determine the capability of polypeptides to also transform ZEN derivatives, in addition to ZEN, into nontoxic and/or less toxic metabolites, the polypeptides having the sequence ID numbers 1 to 15 were prepared as described in Example 3 with C-terminal His tag and the respective synthetic nucleotide sequences with the sequences having sequence ID numbers 17 to 31 were used as the cell lysates in degradation 15.

The degradation experiments were performed as described in Example 3, where each polypeptide was tested with each ZEN derivative selected from the group comprised of α-ZEL, β-ZEL, α-ZAL, β-ZAL, Z14G, Z14S and ZAN, The cell lysates were used in a total dilution of 1:10,000. Instead of a 2.08 mM ZEN solution (40 vol % CAN+60 vol % H$_2$O), equimolar, i.e., 2.08 mM solutions of the ZEN derivatives were used as the substrate stock solution. α-ZEL, β-ZEL, α-ZAL, β-ZAL and ZAN were obtained from Sigma and used as standards for the analysis. Z14G and Z14S were prepared in a purity of at least 90% according to the methods such as those described by P. Krenn et al., 2007 (Mykotoxin Research, 23, 4, 180-184) and M. Sulyok et al., 2007 (Anal. Bioanal. Chem. 289, 1505-1523) and used as standards for the analysis. Another difference in comparison with Example 3 is that only one sample was taken, namely after 24 hours. The reduction in concentration of the ZEN derivatives during the degradation experiment was quantified by means of LC/MS/MS. α-ZEL, β-ZEL, Z14G and Z14S were measured by the method of M. Sulyok et al. (2010, Food Chemistry, 119, 408-416); α-ZAL, β-ZAL and ZAN were measured by the method of P. Songsermaskul et al. (2011, J. of Animal Physiol. and Animal Nutr., 97, 155-161). It was surprisingly found that only 0 to max. 13% of the starting amounts of the ZEN derivatives was present after 24 hours of incubation in all the degradation experiments.

Example 5: Specific Activity and Enzyme Kinetic Parameters of the Polypeptides as Well as Variants Thereof The specific activity of the polypeptides and variants thereof was determined photometrically, wherein all the polypeptides used had a C-terminal 6×His tag. The preparation, enrichment and purification of the polypeptides and/or variants thereof were performed as described in example 1. Degradation of ZEN to HZEN was measured on the basis of the reduction in absorption at the wavelength of 315 nm. The molar extinction coefficients ($\epsilon$) of ZEN and HZEN were determined experimentally and were found to amount to 0.0078895 L μmol$^{-1}$ cm$^{-1}$ and 0.0030857 L μmol$^{-1}$ cm$^{-1}$. The extinction coefficients have a strong dependence on pH and therefore the activity must always be measured precisely at the same pH and preferably also in the same matrix. The measurements were performed in a 50 mM Tris-HCl pH=8.2 buffer solution in quartz cuvettes in a wavelength range of 200 to 2500 nm in a UV-VIS photometer (Hitachi U-2001) at 32° C.

A 2.08 mM ZEN solution (40 vol % ACN+60 vol % H$_2$O) was used as the ZEN substrate stock solution. To prepare this solution, ZEN in crystalline form (Biopure Standard from Romer Labs, article no. 001109, purity at least 98%) was weighed and dissolved accordingly. The ZEN substrate dilutions (0.79 μM, 1.57 μM, 2.36 μM, 3.14 μM, 4.71 μM, 6.28 μM, 7.85 μM, 9.42 μM, 10.99 μM, 12.56 μM, 14.13 μM, 15.71 μM, 17.28 μM and 18.85 μM) were prepared with 50 mM Tris-HCl pH=8.2. The polypeptide solutions were diluted to a final concentration of approximately 70 ng/mL using 50 mM Tris-HCl buffer pH=8.2. The ZEN substrate dilutions were preheated to 32° C. in a water bath.

100 μL portions of the respective ZEN substrate dilution were mixed with 0.2 μL polypeptide solution, and the absorption was measured for 5 minutes, whereupon each combination of polypeptide solution and ZEN substrate dilution was measured at least twice.

Taking into account the extinction coefficients of ZEN and HZEN, the reaction rate was calculated for each substance concentration on the basis of the slope in the absorption over time.

The designations "$K_M$ value" or "Michaelis-Menten constant" relate to a parameter for describing the enzymatic affinity of the units μM or mM, which are calculated with the help of the linear Hanes plots according to H. Bisswang (2002, Enzyme Kinetics, ISBN 3-527-30343-X, page 19), wherein the function "enzyme kinetics, single substrate" in the SigmaPlot 12.0 program is preferably used for this purpose. The designations "catalytic constant of the enzyme reaction" or "$k_{cat}$ value" relate to a parameter for describing the conversion rate of a polypeptide and/or enzyme, which is given in s$^{-1}$ and is preferably calculated with the help of the "enzyme kinetic, single substrate" function of the SigmaPlot 12.0 program. The "maximum enzyme rate" or "$v_{max}$ value" is given in units of μM/s or mM/s and is determined with the help of the linear Hanes plot by analogy with the $K_M$ value, wherein the function "enzyme kinetic, single substrate" of the SigmaPlot 12.0 program is preferably used for this.

The specific activity was calculated by means of $v_{max}$ and the enzyme concentration used according to the equation $$\text{Specific activity (U/mg)} = \frac{v_{max}\ (\mu M/s)60\ (s/min)}{\text{enzyme concentration (mg/L)}}$$

wherein one unit is defined as hydrolysis of 1 μmol ZEN per minute at 32° C. in 50 mM Tris-HCl buffer solution, pH=8.2.

The raw data for determination of the enzyme parameters $K_M$, $v_{max}$, $k_{cat}$ and the specific activity are given below for the polypeptide having the sequence ID no. 1. Table 3 shows the reaction rates at the respective ZEN substrate concentrations, while FIG. 2 shows the respective Michaelis-Menton graphs and Table 4 shows the corresponding enzyme kinetic parameters. The enzyme solution that was used had a concentration of 68 ng/L.

TABLE 3

Reaction rates of the polypeptide with sequence ID no. 1 at different ZEN concentrations.

| ZEN substrate dilution (μM) | Measurement 1 reaction rate (μM/s) | Measurement 2 reaction rate (μM/s) |
|---|---|---|
| 0.79 | 0.0073 | 0.0071 |
| 1.57 | 0.0087 | 0.0082 |
| 2.36 | 0.0095 | 0.0080 |
| 3.14 | 0.0101 | 0.0073 |
| 4.71 | 0.0103 | 0.0087 |
| 6.28 | 0.0096 | 0.0088 |
| 7.85 | 0.0084 | 6.0088 |
| 9.42 | 0.0111 | 0.0087 |
| 10.99 | 0.0093 | 0.0081 |
| 12.56 | 0.0100 | 0.0086 |
| 14.13 | 0.0089 | 0.0101 |
| 15.71 | 0.0089 | 0.0090 |
| 17.28 | 0.0100 | 0.0074 |
| 18.85 | 0.0100 | 0.0085 |

TABLE 4

Enzyme kinetics parameters of the polypeptide having sequence ID no. 1.

| | $v_{max}$ (μM/s) | | $K_M$ (μM) | | $k_{cat}$ (s$^{-1}$) | | Specific activity (U/mg) | |
|---|---|---|---|---|---|---|---|---|
| | Measurement | | | | | | | |
| | 1 | 2 | 1 | 2 | 1 | 2 | 1 | 2 |
| Value | 0.00993 | 0.008756 | 0.2172 | 0.1898 | 5.44 | 4.79 | 8.76 | 7.73 |
| Average | 0.009343 | | 0.2035 | | 5.12 | | 8.25 | |

The specific activities of the polypeptides tested are 8.25 U/mg for sequence ID no. 1, 10.56 U/mg for sequence ID no. 2, 8.36 U/mg for sequence ID no. 3, 8.33 U/mg for sequence ID no. 4, 8.56 U/mg for sequence ID no. 5, 9.95 U/mg for sequence ID no. 6, 3.83 U/mg for sequence ID no. 7, 2.57 U/mg for sequence ID no. 8, 4.87 U/mg for sequence ID no. 9, 5.12 U/mg for sequence ID no. 10, 3.88 U/mg for sequence ID no. 11, 2.78 U/mg for sequence ID no. 12, 6.43 U/mg for sequence ID no. 13, 3.33 U/mg for sequence ID no. 14 and 7.76 U/mg for sequence ID no. 15.

The specific activities of the polypeptide variants tested are listed in Table 5 and Table 6.

TABLE 5

Specific activity of functional variants of the polypeptides having sequence ID no. 1; conserved amino acid sequence segments, in which the mutation(s) is/are located, and sequence identity of the functional variants for the parental sequence having sequence ID no. 1. The position of the mutations is given in relation to the amino acid sequence having sequence ID no. 1. The sequence identity was determined by means of BLAST, as described in Example 2.

| n | Mutation(s) | Mutation(s) in range | Identity with SEQ ID No. 1 | Specific activity (U/mg) |
|---|---|---|---|---|
| ZH1-A-001 | N25D | A | 99.7% | 8.10 |
| ZH1-A-002 | F27Y | A | 99.7% | 7.93 |
| ZH1-A-003 | F27H | A | 99.7% | 7.78 |
| ZH1-A-004 | R35K | A | 99.7% | 8.98 |
| ZH1-A-005 | R35Q | A | 99.7% | 8.56 |
| ZH1-A-006 | N25D/S29P/V42I/V43T | A | 98.8% | 7.84 |
| ZH1-A-007 | I26V/R31A/F32Y/F46Y | A | 98.8% | 8.61 |
| ZH1-A-S02 | N25D/I26V/F27Y/S29P/R31A/F32Y/R35K/V37A/V42I/V43T/F46Y | A | 96.6% | 8.73 |
| ZH1-A-S03 | N25D/I26V/F27H/S29P/R31A/F32Y/R35Q/V42I/V43T/F46Y | A | 97.0% | 8.52 |
| ZH1-B-001 | D53G | B | 99.7% | 8.10 |
| ZH1-B-002 | N54M | B | 99.7% | 8.41 |
| ZH1-B-003 | N54R | B | 99.7% | 8.33 |
| ZH1-B-004 | S69G | B | 99.7% | 8.06 |
| ZH1-B-005 | P72E | B | 99.7% | 8.65 |
| ZH1-B-006 | P72R | B | 99.7% | 8.78 |
| ZH1-B-S02 | N54M/L57V/L60I/S69G/P72E/V73A | B | 98.2% | 8.51 |
| ZH1-B-S03 | D53G/N54R/L57V/L60I/P72E/V73A | B | 98.2% | 8.56 |
| ZH1-B-S04 | N54R/L57V/L60I/P72E/V73A | B | 98.5% | 8.96 |
| ZH1-B-S14 | N54R/L58V/L59P/L60V/T64G/P72R/G75P/L77P | B | 97.6% | 8.68 |
| ZH1-C-001 | N80H | C | 99.7% | 8.24 |
| ZH1-C-002 | N80D | C | 99.7% | 8.48 |
| ZH1-C-003 | F84Y | C | 99.7% | 8.65 |
| ZH1-C-S06 | N80H/F84Y | C | 99.4% | 8.88 |
| ZH1-C-S10 | N80H/F84H | C | 99.4% | 8.32 |
| ZH1-C-S14 | E79R/N80D | C | 99.4% | 8.45 |
| ZH1-D-001 | T95S | D | 99.7% | 8.53 |
| ZH1-D-002 | R99K | D | 99.7% | 8.25 |

TABLE 5-continued

Specific activity of functional variants of the polypeptides having sequence ID no. 1; conserved amino acid sequence segments, in which the mutation(s) is/are located, and sequence identity of the functional variants for the parental sequence having sequence ID no. 1. The position of the mutations is given in relation to the amino acid sequence having sequence ID no. 1. The sequence identity was determined by means of BLAST, as described in Example 2.

| n | Mutation(s) | Mutation(s) in range | Identity with SEQ ID No. 1 | Specific activity (U/mg) |
|---|---|---|---|---|
| ZH1-D-003 | V123I | D | 99.7% | 8.17 |
| ZH1-D-004 | A125G | D | 99.7% | 8.36 |
| ZH1-D-005 | G126A | D | 99.7% | 8.41 |
| ZH1-D-006 | G130A | D | 99.7% | 8.69 |
| ZH1-D-007 | G130V | D | 99.7% | 8.54 |
| ZH1-D-008 | G131A | D | 99.7% | 8.71 |
| ZH1-D-009 | N127D | D | 99.7% | 8.29 |
| ZH1-D-010 | N127Q | D | 99.7% | 8.34 |
| ZH1-D-011 | A141S | D | 99.7% | 8.67 |
| ZH1-D-012 | F106W | D | 99.7% | 7.84 |
| ZH1-D-013 | I118V | D | 99.7% | 8.37 |
| ZH1-D-014 | I118V/V123L | D | 99.4% | 8.55 |
| ZH1-D-015 | I118V/K119R/L132V | D | 99.1% | 8.86 |
| ZH1-D-016 | W96Q/F106W/L116G/V122A | D | 98.8% | 8.65 |
| ZH1-D-017 | Q91R/N105D/K119G/A141S/M142K | D | 98.5% | 8.46 |
| ZH1-D-S02 | T95S/T97A/R99K/I118V/V123I/L132V/A141S | D | 97.7% | 8.66 |
| ZH1-D-S03 | T95S/R99K/I118V/K119R/L132V/A141S | D | 98.2% | 9.32 |
| ZH1-D-S04 | T95S/R99K/I118V/L132V/A141S | D | 98.5% | 9.15 |
| ZH1-D-S05 | T95S/R99K/I114M/I118V/K119R/L132V/A141S | D | 97.7% | 8.84 |
| ZH1-D-S07 | R99G/A115D/K119G/P121T/V123I/A125S/L132V/L133V/S138A/Y140F/A141S/M142L | D | 96.3% | 8.79 |
| ZH1-D-S08 | R93K/W96Q/R99G/D104N/N105L/F106M/A115S/V123I/A125S/G144N | D | 97.0% | 8.86 |
| ZH1-D-S09 | R99G/S102N/D104N/N105T/F106W/L110V/V111E/A115D/K119G/V122T/V123L/L132V/L133I/S138A/M142K | D | 95.4% | 8.99 |
| ZH1-D-S10 | W96R/S102T/F106I/I114L/A115S/L116G/K119G/V122A/V123F/A125S/A134S/Y140F/M142E | D | 96.0% | 9.12 |
| ZH1-D-S11 | W96R/R99G/S102T/F106V/I114L/A115D/L116G/K119G/V122A/V123F/A125S/N127L/L133A/A134S/Y140F/M142K | D | 95.1% | 8.54 |
| ZH1-D-S12 | S94T/R99G/S102T/N105I/L110V/A115D/K119G/P121E/V122T/V123L/V124I/L133I/A134G/S138A/Y140F/M142K | D | 95.1% | 8.69 |
| ZH1-D-S13 | R93Q/R99G/N105T/R112K/A115D/L116I/A125S/N127L/L132V/L133V/A134S/Y140F/M142K | D | 96.0% | 8.47 |
| ZH1-D-S14 | Q91R/W96Q/N105D/I114L/I118V/K119R/V122A/L132V/L137S | D | 97.3% | 8.55 |
| ZH1-E-001 | Y165C | E | 99.7% | 8.46 |
| ZH1-E-002 | Y165H | E | 99.7% | 8.33 |
| ZH1-E-003 | P163T | E | 99.7% | 7.95 |
| ZH1-E-004 | A154P/Y165C | E | 99.4% | 8.13 |
| ZH1-E-S02 | P163T/A164T/Y165C/V169I/L170R | E | 98.5% | 8.83 |
| ZH1-E-S05 | A154P/Y165H/L170R | E | 99.1% | 9.65 |
| ZH1-F-001 | Y180F | F | 99.7% | 8.35 |
| ZH1-F-002 | D182T | F | 99.7% | 8.41 |
| ZH1-F-003 | D182K | F | 99.7% | 8.19 |
| ZH1-F-004 | Y180F/R181V/I190V | F | 99.1% | 8.56 |
| ZH1-F-S04 | Y180F/D182T/F183Y/I190V/G191S | F | 98.5% | 8.56 |
| ZH1-F-S06 | Y180F/D182T/F183Y/I190V | F | 98.8% | 8.64 |
| ZH1-F-S10 | E178A/R181V/D182K/F183Y | F | 98.8% | 7.55 |
| ZH1-H-001 | T236K | H | 99.7% | 8.09 |
| ZH1-H-002 | V237F | H | 99.7% | 8.11 |
| ZH1-H-003 | E234G | H | 99.7% | 8.54 |
| ZH1-H-S02 | F233W | H | 99.7% | 8.37 |
| ZH1-H-S03 | F233Y | H | 99.7% | 8.64 |
| ZH1-H-S04 | F233H | H | 99.7% | 8.36 |
| ZH1-H-S06 | A231V/F233Y | H | 99.4% | 8.54 |
| ZH1-H-S09 | F232W/F233A/E234T/G235D/L239A | H | 98.5% | 8.83 |
| ZH1-I-001 | H240N | I | 99.7% | 8.54 |
| ZH1-I-002 | H240S | I | 99.7% | 8.79 |
| ZH1-I-003 | D244E/R245Y | I | 99.4% | 8.42 |
| ZH1-I-S02 | D244E/R245Q/M246L | I | 99.1% | 8.36 |
| ZH1-I-S03 | H240N/D244E | I | 99.4% | 9.26 |
| ZH1-I-S06 | H240S/D244E | I | 99.4% | 9.02 |
| ZH1-I-S07 | L239Q/H240T/R245Y | I | 99.1% | 8.41 |
| ZH1-J-001 | Q249R | J | 99.7% | 8.36 |
| ZH1-J-002 | T252V | J | 99.7% | 7.94 |
| ZH1-J-S02 | I254V | J | 99.7% | 8.55 |
| ZH1-J-S03 | Q249R/K251N/I254V | J | 99.1% | 9.03 |
| ZH1-J-S07 | T252V/I254M | J | 99.4% | 7.81 |
| ZH1-J-S10 | T252V/I254V | J | 99.4% | 7.97 |
| ZH1-K-S05 | A260M | K | 99.7% | 8.64 |
| ZH1-K-S11 | A260F | K | 99.7% | 8.82 |
| ZH1-K-S13 | A260S | K | 99.7% | 9.01 |
| ZH1-L-001 | E266Y | L | 99.7% | 8.46 |
| ZH1-L-002 | E266D | L | 99.7% | 8.31 |
| ZH1-L-003 | T262G | L | 99.7% | 8.32 |
| ZH1-L-004 | T262D/E266D | L | 99.4% | 8.56 |
| ZH1-L-005 | T262G/I283T | L | 99.4% | 8.68 |
| ZH1-L-S02 | E266D/E269H | L | 99.4% | 8.59 |
| ZH1-L-S04 | I263T/E269N | L | 99.4% | 8.73 |
| ZH1-L-S06 | E269N | L | 99.7% | 8.69 |
| ZH1-L-S13 | E266Y/E269N | L | 99.4% | 8.33 |
| ZH1-M-001 | L274M | M | 99.7% | 8.29 |
| ZH1-M-002 | L274C | M | 99.7% | 8.37 |
| ZH1-M-S02 | L277E | M | 99.7% | 8.96 |
| ZH1-M-S07 | L274M/A279V | M | 99.4% | 8.23 |
| ZH1-M-S08 | L274T/L277F | M | 99.4% | 8.63 |
| ZH1-M-S11 | L274C/L277I | M | 99.4% | 8.51 |
| ZH1-N-001 | H297L | N | 99.7% | 8.27 |
| ZH1-N-002 | H298V/L302S | N | 99.4% | 9.03 |
| ZH1-N-S02 | H298V | N | 99.7% | 8.94 |
| ZH1-N-S09 | H298L/P299D | N | 99.4% | 8.37 |
| ZH1-O-001 | L307Q | O | 99.7% | 8.62 |
| ZH1-O-002 | F308S | O | 99.7% | 8.57 |
| ZH1-O-S02 | L307Q/A311P | O | 99.4% | 8.34 |
| ZH1-O-S03 | L307Q/F308S | O | 99.4% | 8.74 |
| ZH1-O-S06 | L307Q/F308S/D309A | O | 99.1% | 9.18 |
| ZH1-B/H-001 | D53G/N54R/L57V/L60I/P72E/V73A/F233V/E234G/V237F | B + H | 97.3% | 9.26 |

TABLE 5-continued

Specific activity of functional variants of the polypeptides having sequence ID no. 1; conserved amino acid sequence segments, in which the mutation(s) is/are located, and sequence identity of the functional variants for the parental sequence having sequence ID no. 1. The position of the mutations is given in relation to the amino acid sequence having sequence ID no. 1. The sequence identity was determined by means of BLAST, as described in Example 2.

| n | Mutation(s) | Mutation(s) in range | Identity with SEQ ID No. 1 | Specific activity (U/mg) |
|---|---|---|---|---|
| ZH1-C/D-001 | N80H/F84Y/T95S/R99K/I118V/K119R/L132V/A141S | C + D | 97.6% | 9.31 |
| ZH1-D/K-001 | T95S/T97A/R99K/I118V/V123I/L132V/A141S/A260M | D + K | 97.6% | 9.66 |
| ZH1-D/M-001 | T95S/T97A/R99K/I118V/V123I/L132V/A141S/L277E | D + M | 97.6% | 10.63 |
| ZH1-K/N-001 | A260M/H298V | K + N | 99.4% | 8.94 |
| ZH1-K/L-001 | A260M/T262D/E266D/E269H | K + L | 98.8% | 9.03 |
| ZH1-K/L-002 | A260M/T262G/I263T/E269N | K + L | 98.8% | 8.84 |
| ZH1-N/O-001 | Q296H/H298V/L307Q/A311P | N + O | 98.8% | 9.26 |
| ZH1-N/O-002 | Q296E/H298V/L302S/L307Q/F308S | N + O | 98.5% | 9.46 |
| ZH1-C/D/J-001 | N80H/F84Y/T95S/R99K/I118V/L132V/A141S/Q249R/K251N/I254V | C + D + J | 97.0% | 9.97 |
| ZH1-B/D/K-001 | D53G/N54R/L57V/L60I/P72E/V73A/T95S/R99K/I114M/I118V/K119R/L132V/A141S/A260M | B + D + K | 95.7% | 10.78 |
| ZH-J/K/L-001 | I254V/I256L/A260M/T262G/I263T/E269N | J + K + L | 98.2% | 9.11 |
| ZH1-J/K/LM-001 | I254V/I256L/A260M/T262D/E266D/E269H/L271V | J + K + L + M | 97.7% | 9.14 |
| ZH1-B/C/D/J-002 | E79R/N80D/D53G/N54R/L57V/L60I/P72E/V73A/W96R/R99G/S102T/F106V/I114L/A115D/L116G/K119G/V122A/V123F/A125S/N127L/L133A/A134S/Y140F/M142K/T252V/I254V | B + C + D + J | 92.1% | 11.31 |
| ZH1-DEL-001 | ΔP212 | — | 99.7% | 8.56 |
| ZH1-DEL-002 | ΔG5/ΔT6/ΔR7/ΔS8/ΔE9/ΔA10/ΔA11/ΔD12/ΔA13/ΔA14/ΔT15/ΔQ16/ΔA17/ΔR18/ΔQ19 | — | 95.4% | 8.37 |
| ZH1-DEL-003 | ΔN327/ΔD328 | — | 99.4% | 8.27 |
| ZH1-A/B/C-001 | N25D/I26V/F27Y/S29P/R31A/F32Y/R35K/V37A/V42I/V43T/F46Y/N54R/L58V/L59P/L60V/T64G/P72R/G75P/L77P/R99G/S102N/D104N/N105T/F106W/L110V/V111E/A115D/K119G/V122T/V123L/L132V/L133I/S138A/M142K | A + B + C | 89.6% | 9.54 |
| ZH1-DEL/B/C/D/J-001 | ΔG5/ΔT6/ΔR7/ΔS8/ΔE9/ΔA10/ΔA11/ΔD12/ΔA13/ΔA14/ΔT15/ΔQ16/ΔA17/ΔR18/ΔQ19/ΔP212/ΔN327/ΔD328/E79R/N80D/D53G/N54R/L57V/L60I/P72E/V73A/W96R/R99G/S102T/F106V/I114L/A115D/L116G/K119G/V122A/V123F/A125S/N127L/L133A/A134S/Y140F/M142K/T252V/I254V | B + C + D + J | 86.6% | 11.52 |
| ZH1-DEL/A/B/C/D/J-001 | ΔG5/ΔT6/ΔR7/ΔS8/ΔE9/ΔA10/ΔA11/ΔD12/ΔA13/ΔA14/ΔT15/ΔQ16/ΔA17/ΔR18/ΔQ19/ΔP212/ΔN327/ΔD328/N25D/I26V/F27Y/S29P/R31A/F32Y/R35K/V37A/V42I/V43T/F46Y/E79R/N80D/D53G/N54R/L57V/L60I/P72E/V73A/W96R/R99G/S102T/F106V/I114L/A115D/L116G/K119G/V122A/V123F/A125S/N127L/L133A/A134S/Y140F/M142K/T252V/I254V | A + B + C + D + J | 83.3% | 10.92 |
| ZH1-001 | L302S | — | 99.7% | 8.31 |

TABLE 6

Specific activities of functional variants of the polypeptide having sequence ID no. 2. The position of the mutation(s) is relative to the amino acid sequence with sequence ID no. 2. The sequence identity was determined by means of BLAST as described in example 2.

| Variant | Mutation(s) | Identity with SEQ ID No. 2 | Specific activity (U/mg) |
|---|---|---|---|
| ZH2-001 | D3D(GTRSEAADAATQARQL) | 93.6% | 10.15 |
| ZH2-002 | D8N/V9I/Y10F | 99.0% | 10.42 |
| ZH2-003 | M37N/E55P/A56V/V101I/S124A/F194FP/T146P/T147A/C148Y | 97.0% | 10.58 |
| ZH2-004 | S187P/S188A/P189K/M190A/A191M/R192Q/Y193L | 97.7% | 10.43 |
| ZH2-005 | A262E/R263H/R265Q/L266D/L267I/M268I/E269R | 97.7% | 10.68 |
| ZH2-008 | D3D(GTRSEAADAATQARQL)/M37N/E55P/A56V/V101I/S124A/F194FP/T146P/T147A/C148Y/S187P/S188A/P189K/M190A/A191M/R192Q/Y193L/A262E/R263H/R265Q/L266D/L267I/M268I/E269R | 86.1% | 10.71 |

Example 6: Degradation of ZEN and ZEN Derivatives in Contaminated Corn

To determine the capabilities of polypeptides to degrade naturally occurring ZEN and ZEN derivatives in a complex matrix and at a low pH, contaminated corn was mixed with different concentrations of one of the polypeptides having the sequence ID numbers 1 to 6 and the degradation of ZEN and ZEN derivatives was tracked.

The contaminated corn was ground and used in the degradation experiment wherein a batch would consist of 1 g ground contaminated corn, 8.9 mL 100 mM acetate buffer pH 4.0 and 0.1 mL polypeptide solution. Enriched and purified polypeptide solutions were prepared as described in example 5, diluting them to a concentration of 10 mU/mL, 100 mU/mL and/or 1000 mU/mL. Thus in absolute amounts 1 mU (=1 mU per gram corn), 10 mU (=10 mU per gram corn) and/or 100 mU (=100 mU per gram of corn) were used in the batch. Each degradation batch was carried out in 25 mL and incubated at 37° C. and 100 rpm with agitation. Before adding the enzyme and/or after 1 hour of incubation, a sample of 1 mL was taken, the polypeptide was heat inactivated at 99° C. for 10 minutes and the sample was stored at −20° C. After thawing the sample, the insoluble constituents were separated by centrifugation. Concentrations of ZEN and ZEN derivatives were measured by means of LC/MS/MS as described by M. Sulyok et al. (2007, Anal. Bioanal. Chem., 289, 1505-1523). The ZEN and ZEN derivative content in this corn was 238 ppb for ZEN, 15 ppb for α-ZEL, 23 ppb for β-ZEL, 32 ppb for Z14G and 81 ppb for Z14S. Table 7 shows the percentage reduction in the ZEN and ZEN derivative content in the degradation experiment.

TABLE 7

Reduction in ZEN and ZEN derivatives in percentage based on the starting content in the degradation experiment with different polypeptides and amounts of polypeptides.

| Polypeptide | Amount in the batch | ZEN | α-ZEL | β-ZEL | Z14G | Z14S |
|---|---|---|---|---|---|---|
| SEQ ID No. 1 | 0.1 mU | 83% | ≥80% | 70% | 78% | 80% |
|  | 1 mU | 96% | ≥80% | 76% | ≥80% | 92% |
|  | 10 mU | 97% | ≥80% | ≥85% | ≥80% | 94% |
| SEQ ID No. 2 | 0.1 mU | 87% | ≥80% | 73% | ≥80% | 84% |
|  | 1 mU | 97% | ≥80% | 78% | ≥80% | 90% |
|  | 10 mU | 99% | ≥80% | ≥85% | ≥80% | 96% |
| SEQ ID No. 3 | 0.1 mU | 79% | 79% | 67% | 73% | 75% |
|  | 1 mU | 85% | ≥80% | 72% | 79% | 82% |
|  | 10 mU | 92% | ≥80% | 78% | ≥80% | 88% |
| SEQ ID No. 4 | 0.1 mU | 82% | 78% | 65% | 76% | 80% |
|  | 1 mU | 89% | ≥80% | 73% | ≥80% | 86% |
|  | 10 mU | 93% | ≥80% | 82% | ≥80% | 91% |
| SEQ ID No. 5 | 0.1 mU | 79% | 76% | 66% | 78% | 80% |
|  | 1 mU | 83% | ≥80% | 73% | ≥80% | 81% |
|  | 10 mU | 91% | ≥80% | 79% | ≥80% | 86% |
| SEQ ID No. 6 | 0.1 mU | 93% | ≥80% | 75% | ≥80% | 90% |
|  | 1 mU | 95% | ≥80% | 82% | ≥80% | 92% |
|  | 10 mU | 98% | ≥80% | ≥85% | ≥80% | 96% |

Example 7: Additives Containing Polypeptide for Hydrolytic Cleavage of ZEN and/or ZEN Derivatives To prepare additives for hydrolytic cleavage of ZEN, fermentation supernatants of polypeptides expressed by *P. pastoris* and having the sequence ID numbers 1, 2, 6 and 13 were purified by microfiltration and ultrafiltration (exclusion limit: 10 kDa) under standard conditions and concentrated up to a dry substance concentration of approximately 9% by weight. Following that, these polypeptide-containing solutions were also processed further to form dry powders under standard conditions in a spray dryer (Mini B290 from Büchi). These four powders were subsequently designated as Z1, Z2, Z6 and Z13. Z1, Z2, Z6 and/or Z13 were additionally mixed with bentonite having an average grain size of approximately 1 µm in a ratio of 1% by weight of additives Z1, Z2, Z6 and/or Z13 and 99% by weight bentonite in an overhead agitator. The resulting additives are designated as additives Z1.B, Z2.B, Z6.B and Z13.B. In addition, Z1, Z2, Z6 and Z13 were mixed with bentonite and a vitamin trace element concentrate in a ratio of 0.1% by weight additive Z1, Z2, Z6 and/or Z13, 0.9% by weight vitamin trace elements concentrate and 99% by weight bentonite in an overhead agitator. The resulting additives were designated as additive Z1.BVS, Z2.BVS, Z6.BVS and Z13.BVS. 100 g of the additives Z1.BVS, Z2.BVS, Z6.BVS and Z13.BVS contained 200 mg iron sulfate, 50 mg copper sulfate, 130 mg zinc oxide, 130 mg manganese oxide, 2.55 mg calcium carbonate, 160 mg vitamin E, 6.5 mg vitamin K3, 6.5 mg vitamin B1, 14 mg vitamin B2, 15 mg vitamin B6, 0.15 mg vitamin B12, 150 mg nicotinic acid, 30 mg pantothenic acid and 5.3 mg folic acid.

The additives were extracted for 30 minutes in a 50 mM Tris-HCl buffer pH=8.2 and diluted further in the same buffer so that the final concentration of polypeptide was approximately 70 ng/mL.

Following that, the zearalenone-degrading effect of these solutions was determined as described in Example 5. The corresponding activities were 8.230 U/g for Z1, 9.310 U/g for Z2, 9.214 U/g for Z6, 83 U/g for Z1.B, 92 U/g for Z2.B, 90 U/g for Z2.C, 57 U/g for Z13.B, 8 U/g for Z1.BVS, 9 U/g for Z2.BVS, 9 U/g for Z6.BVS and 6 U/g for Z13.BVS.

The ability to degrade ZEN derivatives α-ZEL, β-ZEL, α-ZAL, β-ZAL, Z14G, Z14S and ZAN by the additives Z1, Z2, Z6, Z13, Z1.B, Z2.B, Z6.B, Z13.B, Z1.BVS, Z2.BVS, Z6.BVS and Z13.BVS was tested as described in Example 4, but instead of 100 µL of a cell lysate, 100 µL of a polypeptide solution with a polypeptide concentration of approximately 70 ng/mL was used. After incubating for 6 hours, only max. 15% of the starting amount was present as unhydrolyzed ZEN derivative.

Example 8: Optimum Temperature

To determine the temperature optimum of the polypeptides having SEQ ID numbers 1, 2, 5, 6, 7, 9, 11, 12 and 15, they were cloned with a C-terminal 6×His tag as described in example 1, expressed in *E. coli* and purified. In preliminary experiments, the concentration at which a complete conversion of ZEN could be ensured under the experimental conditions was determined (Teorell-Stenhagen buffer (Teorell and Stenhagen, A universal buffer for the pH range of 2.0 to 12.0. Biochem Ztschrft, 1938, 299:416-419), pH 7.5 with 0.1 mg/mL BSA at 30° C.) after an experimental time of 3 hours. The preparations were used in the concentrations thus determined in the degradation batches for determining the optimum temperature. The experiments were carried out in a PCR Cycler (Eppendorf) using the temperature gradient function at 20° C.±10° C., at 40° C.±10° C. and, if necessary, at 60° C.±10° C. (10 temperatures in the respective range; temperatures predefined by the PCR cycler). For the batches Teorell-Stenhagen buffer was mixed with the corresponding enzyme concentration and 0.1 mg/mL BSA plus 5 ppm ZEN at the respective optimum pH. Batches with 0.1 mg/mL BSA and 5 ppm ZEN without addition of an enzyme were used as negative controls. After 0 h, 0.5 h, 1 h, 2 h and 3 h incubation time, a sample was taken per incubation temperature, heat inactivated for 10 minutes at 99° C. and stored at −20° C. After thawing, the samples were transferred to HPLC vials. ZEN, HZEN and DHZEN were analyzed by HPLC-DAD. To do so the metabolites were separated chromatographically on a Zorbax SB-Aq C18 column with the dimensions 4.6 mm×150 mm and a particle size of 5 μm. A methanol-water mixture with 5 mM ammonium acetate was used as the mobile phase. The UV signal at 274 nm was recorded. The metabolites were quantified by including entrained standard series. The optimum temperatures were determined on the basis of the slopes determined for the degradation curves, where the optimum temperature was defined as the temperature at which the slope was the greatest. Table 8 shows the optimum temperatures.

TABLE 8

Optimum temperatures of the polypeptides.

| SEQ ID No. 1 | SEQ ID No. 2 | SEQ ID No. 5 | SEQ ID No. 6 | SEQ ID No. 7 | SEQ ID No. 9 | SEQ ID No. 11 | SEQ ID No. 12 | SEQ ID No.15 |
|---|---|---|---|---|---|---|---|---|
| 38° C. | 41° C. | 50° C. | 51° C. | 31° C. | 35° C. | 50° C. | 26° C. | 41° C. |

Example 9: Thermal Stability

To determine the thermal stability of polypeptides with the SEQ ID numbers 1, 2, 5, 6, 7, 9, 11, 12 and 15, they were cloned with a C-terminal 6×His tag as described in Example 1, expressed in *E. coli* and purified. They were then incubated in the PCR cycler with a gradient function at the respective optimum temperature ±10° C. After 0 min, 15 min, 30 min and 60 min, one sample was taken per batch and per temperature. These pre-incubated samples were then used in a degradation experiment in the Teorell-Stenhagen buffer at the respective optimum pH with 0.1 mg/mL BSA and 5 ppm ZEN. In preliminary experiments, the concentration at which a complete reaction of ZEN could be ensured after an experimental duration of 3 hours under the experimental conditions (Teorell-Stenhagen buffer, pH 7.5 with 0.1 mg/mL BSA at 30° C.) was determined for each polypeptide. The respective enzyme concentration thereby determined was used in the batches. The degradation batches were incubated at 30° C. Sampling was performed after 0 h, 0.5 h, 1 h, 2 h and 3 h incubation time. Next, the polypeptides were heat-inactivated for 10 minutes at 99° C. and the samples were stored at −20° C. After thawing the samples were transferred to HPLC vials and analyzed by HPLC-DAD, as described in Example 8.

Thermal stability is defined as the temperature at which the polypeptides have a 50% residual activity in comparison with the optimum temperature after 15 minutes of pre-incubation. As a measure of the activity, the slope in the degradation curves is used. The temperature stabilities are shown in Table 9.

Example 10: Optimum pH

To determine the optimum pH of the polypeptides having the SEQ ID numbers 1, 2, 5, 6, 7, 9, 11, 12 and 15, they were cloned with a C-terminal 6×His tag as described in Example 1, expressed in *E. coli* and purified. In preliminary experiments, the concentration at which a complete conversion of ZEN could be ensured after an experimental duration of 3 hours under the experimental conditions was determined for each polypeptide (Teorell-Stenhagen buffer, pH 7.5 with 0.1 mg/mL BSA at 30° C.). The respective enzyme concentration was used in the batches. The degradation batches were carried out in Stenhagen buffer at pH levels of 3.0, 4.0, 5.0, 5.5, 6.0, 6.5, 7.0, 7.5, 8.0, 8.5, 9.0, 9.5, 10.0, 11.0 and 12.0. For the degradation batches with 0.1 mg/mL BSA and 5 ppm ZEN, incubation was done at 30° C. Batches in Teorell-Stenhagen buffer were used as the negative controls at pH 3.0, pH 7.0 and pH 12.0 with 0.1 mg/mL BSA and 5 ppm ZEN. Sampling was performed after an incubation time of 0 h, 0.5 h, 1 h, 2 h and 3 h. Next the polypeptides were heat-inactivated for 10 minutes at 99° C. and the samples were stored at −20° C. After thawing, the samples were transferred to HPLC vials and analyzed by HPLC-DAD as described in Example 8. The optimum pH was determined on the basis of the slopes found for the degradation curves, wherein the pH at which the slope was the greatest was defined as the optimum pH. Table 10 shows the optimum pH levels.

TABLE 10

Optimum pH of the polypeptides.

| SEQ ID No. 1 | SEQ ID No. 2 | SEQ ID No. 5 | SEQ ID No. 6 | SEQ ID No. 7 | SEQ ID No. 9 | SEQ ID No. 11 | SEQ ID No. 12 | SEQ ID No. 15 |
|---|---|---|---|---|---|---|---|---|
| 8.2 | 8.5 | 7.0-8.0 | 7.0-7.5 | 7.5-8.5 | 7.0-7.5 | 8.0 | 7.0-7.5 | 7.5 |

Example 11: pH Stability at pH 5.0

To determine the pH stability, the polypeptides from Example 10 were incubated for one hour at 25° C. in Teorell-Stenhagen buffer at pH 5.0 and at the respective optimum pH. These pre-incubated samples were used in a degradation experiment in the same concentrations of the respective polypeptide as those used to determine the opti-

TABLE 9

Temperature stability of the polypeptides (50% residual activity after pre-incubation for 15 minutes).

| SEQ ID No. 1 | SEQ ID No. 2 | SEQ ID No. 5 | SEQ ID No. 6 | SEQ ID No. 7 | SEQ ID No. 9 | SEQ ID No. 11 | SEQ ID No. 12 | SEQ ID No. 15 |
|---|---|---|---|---|---|---|---|---|
| 38° C. | 34° C. | 54° C. | 61° C. | 28° C. | 44° C. | 55° C. | 40° C. | 49° C. | mum pH in 100 mM Tris-HCl buffer at the respective optimum pH with 0.1 mg/mL BSA and 5 pm ZEN in the batch. The batches were incubated at the respective optimum temperature. Sampling was performed after 0 h, 0.5 h, 1 h, 2 h and 3 h incubation time. Next the polypeptides were heat inactivated for 10 minutes at 99° C. and the samples were stored at −20° C. After thawing, the samples were transferred to HPLC vials and analyzed by means of HPLC-DAD as described in Example 8. The pH stability is defined as the percentage residual activity of the polypeptides at pH 5.0 relative to the activity at the respective optimum pH. The pH stabilities for 5.0 are shown in Table 11.

TABLE 11 pH stability of the polypeptides at pH 5.0.

| SEQ ID No. 1 | SEQ ID No. 2 | SEQ ID No. 5 | SEQ ID No. 6 | SEQ ID No. 7 | SEQ ID No. 9 | SEQ ID No. 11 | SEQ ID No. 12 | SEQ ID No. 15 |
|---|---|---|---|---|---|---|---|---|
| 3% | 17% | 79% | 80% | 100% | 22% | 87% | 98% | 19% |

Example 12: ZEN Degradation Experiment

The degradation of ZEN to HZEN and DHZEN was performed as an example for the polypeptides with sequence ID numbers 1, 2, 5, 6, 7, 9, 11, 12 and 15. The degradation batches were carried in Teorell-Stenhagen buffer pH 7.5 with 0.1 mg/mL BSA and 5 ppm ZEN. The degradation batches were incubated at 30° C. Sampling was performed after 0 h, 0.5 h, 1 h, 2 h and 3 h incubation time. Next the polypeptides were heat-inactivated for 10 minutes at 99° C. and the samples were stored at −20° C. After thawing, the samples were transferred to HPLC vails and analyzed by HPLC-DAD, as described in Example 8. The polypeptide concentration was selected so that complete degradation was achieved after approximately 3 hours. FIG. 3 shows the degradation kinetics, where the y axis shows the concentration of ZEN, HZEN and DHZEN in micromoles per liter (μmol/L) and the x axis shows the incubation time in hours (h).

*μM denotes micromolar and corresponds to the unit μmol/L

The invention claimed is:

1. A method for hydrolytic cleavage of zearalenone or at least one zearalenone derivative, wherein the zearalenone or at least one zearalenone derivative is/are hydrolyzed by a polypeptide having the amino acid sequence of SEQ ID NO: 1 or a functional variant thereof, wherein the sequence identity between the functional variant and the amino acid sequence is at least 70%,
   wherein the zearalenone derivative is selected from the group of α-ZEL ((2E,7R,11S)-7,15,17-trihydroxy-11-methyl-12-oxabicyclo[12.4.0]-octadeca-1(18),2,14,16-tetraen-13-one), β-ZEL (2E,7S,11S)-7,15,17-trihydroxy-11-methyl-12-oxabicyclo[12.4.0]octadeca-1(18),2,14,16-tetraen-13-one), α-ZAL ((7R,11S)-7,15,17-trihydroxy-11-methyl-12-oxabicyclo[12.4.0]octadeca-1(18),14,16-trien-13-one), β-ZAL ((7S,11S)-7,15,17-trihydroxy-11-methyl-12-oxabicyclo[12.4.0]octadeca-1(14),15,17-trien-13-one), Z14G ((2E,11S)-15-hydroxy-11-methyl-17-[(3R,4S,5S,6R)-3,4,5-trihydroxy-6-(hydroxymethyl)-tetrahydropyran-2-yl]oxy-12-oxabicyclo[12.4.0]octadeca 1(18)2,14,16-tetraene-7,13-dione), Z14S ([(2E,11S)-15-hydroxy-11-methyl-7,13-dioxo-12-oxabicyclo[12.4.0]octadeca-1(18),2,14,16-tetraen-17-yl] hydrogen sulfate) and ZAN ((11S)-15,17-dihydroxy-11-methyl-12-oxabicyclo-[12.4.0]octadeca-1(18),14,16-triene-7,13-dione), and
   wherein the polypeptide having the amino acid sequence of SEQ ID NO: 1 or the functional variant thereof has an α,β-hydrolase structure, which is suitable for oxygen-independent and cofactor-free hydrolytic cleavage of the ester group of zearalenone or at least one zearalenone derivative.

2. The method for hydrolytic cleavage of zearalenone or at least one zearalenone derivative, wherein the zearalenone or at least one zearalenone derivative is/are hydrolyzed by a polypeptide having the amino acid sequence of SEQ ID NO: 1 or a functional variant thereof, wherein the sequence identity between the functional variant and the amino acid sequence is at least 70%, wherein the polypeptide is used in an additive that hydrolytically cleaves zearalenone and/or at least one zearalenone derivative to yield feed products for pigs, poultry or aquaculture, for addition to foodstuffs or to distillers dried grain and solubles,
   wherein the zearalenone derivative is selected from the group of α-ZEL ((2E,7R,11S)-7,15,17-trihydroxy-11-methyl-12-oxabicyclo[12.4.0]-octadeca-1(18),2,14,16-tetraen-13-one), β-ZEL (2E,7S,11S)-7,15,17-trihydroxy-11-methyl-12-oxabicyclo[12.4.0]octadeca-1(18),2,14,16-tetraen-13-one), α-ZAL ((7R,11S)-7,15,17-trihydroxy-11-methyl-12-oxabicyclo[12.4.0]octadeca-1 (18),14,16-trien-13-one), β-ZAL ((7S,11S)-7,15,17-trihydroxy-11-methyl-12-oxabicyclo[12.4.0]octadeca-1(14),15,17-trien-13-one), Z14G ((2E,11S)-15-hydroxy-11-methyl-17-[(3R,4S,5S,6R)-3,4,5-trihydroxy-6-(hydroxymethyl)-tetrahydropyran-2-yl]oxy-12-oxabicyclo[12.4.0]octadeca 1(18)2,14,16-tetraene-7,13-dione), Z14S ([(2E,11S)-15-hydroxy-11-methyl-7,13-dioxo-12-oxabicyclo[12.4.0]octadeca-1(18),2,14,16-tetraen-17-yl]hydrogen sulfate) and ZAN ((11S)-15,17-dihydroxy-11-methyl-12-oxabicyclo-[12.4.0]octadeca-1(18),14,16-triene-7,13-dione); and
   wherein the polypeptide having the amino acid sequence of SEQ ID NO: 1 or the functional variant thereof has an α,β-hydrolase structure, which is suitable for oxygen-independent and cofactor-free hydrolytic cleavage of the ester group of zearalenone or at least one zearalenone derivative.

3. The method according to claim 2, wherein the polypeptide or the additive is mixed with a foodstuff or animal feed product contaminated with zearalenone or with at least one zearalenone derivative; the contaminated foodstuff or animal feed product is brought in contact with moisture, and the polypeptide or the additive hydrolyzes the zearalenone and/or at least one zearalenone derivative present in contaminated foodstuff or animal feed product.

4. The method according to claim 1, characterized in that at least 70%, or at least one zearalenone derivative selected from the group of α-ZEL ((2E,7R,11S)-7,15,17-trihydroxy-11-methyl-12-oxabicyclo[12.4.0]-octadeca-1(18),2,14,16-tetraen-13-one), β-ZEL (2E,7S,11S)-7,15,17-trihydroxy-11-methyl-12-oxabicyclo[12.4.0]octadeca-1(18),2,14,16-tetraen-13-one), α-ZAL ((7R,11S)-7,15,17-trihydroxy-11-methyl-12-oxabicyclo[12.4.0]octadeca-1(18),14,16-trien-13-one), β-ZAL ((7S,11S)-7,15,17-trihydroxy-11-methyl-12-oxabicyclo[12.4.0]octadeca-1(14),15,17-trien-13-one), Z14G ((2E,11S)-15-hydroxy-11-methyl-17-[(3R,4S,5S,6R)-3,4,5-trihydroxy-6-(hydroxymethyl)-tetrahydropyran-2-yl]oxy-12-oxabicyclo[12.4.0]octadeca 1(18)2,14,16-tetraene-7,13-dione), Z14S ([(2E,11S)-15-hydroxy-11-methyl-7,13-dioxo-12-oxabicyclo[12.4.0]octadeca-1(18),2,14,16-tetraen-17-yl] hydrogen sulfate) and ZAN ((11S)-15,17-dihydroxy-11-methyl-12-oxabicyclo-[12.4.0]octadeca-1(18),14,16-triene-7,13-dione) is/are hydrolyzed.

5. The method according to claim 4, characterized in that at least 80% of the zearalenone or at least one zearalenone derivative selected from the group of α-ZEL ((2E,7R,11S)-7,15,17-trihydroxy-11-methyl-12-oxabicyclo[12.4.0]-octadeca-1(18),2,14,16-tetraen-13-one), β-ZEL (2E,7S,11S)-7,15,17-trihydroxy-11-methyl-12-oxabicyclo[12.4.0]octadeca-1(18),2,14,16-tetraen-13-one), α-ZAL ((7R,11S)-7,15,17-trihydroxy-11-methyl-12-oxabicyclo[12.4.0]octadeca-1(18),14,16-trien-13-one), β-ZAL ((7S,11S)-7,15,17-trihydroxy-11-methyl-12-oxabicyclo[12.4.0]octadeca-1(14),15,17-trien-13-one), Z14G ((2E,11S)-15-hydroxy-11-methyl-17-[(3R,4S,5S,6R)-3,4,5-trihydroxy-6-(hydroxymethyl)-tetrahydropyran-2-yl]oxy-12-oxabicyclo[12.4.0]octadeca 1(18)2,14,16-tetraene-7,13-dione), Z14S ([(2E,11S)-15-hydroxy-11-methyl-7,13-dioxo-12-oxabicyclo[12.4.0]octadeca-1(18),2,14,16-tetraen-17-yl] hydrogen sulfate) and ZAN ((11S)-15,17-dihydroxy-11-methyl-12-oxabicyclo-[12.4.0]octadeca-1(18),14,16-triene-7,13-dione) is/are hydrolyzed.

6. The method according to claim 4, characterized in that at least 90% of the zearalenone or at least one zearalenone derivative selected from the group of α-ZEL ((2E,7R,11S)-7,15,17-trihydroxy-11-methyl-12-oxabicyclo[12.4.0]-octadeca-1(18),2,14,16-tetraen-13-one), β-ZEL (2E,7S,11S)-7,15,17-trihydroxy-11-methyl-12-oxabicyclo[12.4.0]octadeca-1(18),2,14,16-tetraen-13-one), α-ZAL ((7R,11S)-7,15,17-trihydroxy-11-methyl-12-oxabicyclo[12.4.0]octadeca-1(18),14,16-trien-13-one), β-ZAL ((7S,11S)-7,15,17-trihydroxy-11-methyl-12-oxabicyclo[12.4.0]octadeca-1(14),15,17-trien-13-one), Z14G ((2E,11S)-15-hydroxy-11-methyl-17-[(3R,4S,5S,6R)-3,4,5-trihydroxy-6-(hydroxymethyl)-tetrahydropyran-2-yl]oxy-12-oxabicyclo[12.4.0]octadeca 1(18)2,14,16-tetraene-7,13-dione), Z14S ([(2E,11S)-15-hydroxy-11-methyl-7,13-dioxo-12-oxabicyclo[12.4.0]octadeca-1(18),2,14,16-tetraen-17-yl] hydrogen sulfate) and ZAN ((11S)-15,17-dihydroxy-11-methyl-12-oxabicyclo-[12.4.0]octadeca-1(18),14,16-triene-7,13-dione) is/are hydrolyzed.

* * * * *